US006342655B1

(12) United States Patent
Boeshore et al.

(10) Patent No.: US 6,342,655 B1
(45) Date of Patent: Jan. 29, 2002

(54) PLANTS RESISTANT TO WT STRAINS OF CUCUMBER MOSAIC VIRUS

(75) Inventors: Maury L. Boeshore, Wauconda, IL (US); J. Russell McMaster, Kenosha, WI (US); David M. Tricoli, Davis, CA (US); John F. Reynolds, Davis, CA (US); Kim J. Carney, Davis, CA (US)

(73) Assignee: Seminis Vegetable Seeds, Inc., Oxnard, CA (US)

( * ) Notice: Subject to any disclaimer, the term of this patent is extended or adjusted under 35 U.S.C. 154(b) by 0 days.

(21) Appl. No.: 09/616,567

(22) Filed: Jul. 14, 2000

Related U.S. Application Data

(62) Division of application No. 08/875,233, filed as application No. PCT/US95/07234 on Jun. 7, 1995, now Pat. No. 6,127,601, which is a continuation of application No. 08/367,789, filed on Dec. 30, 1994, now abandoned.

(51) Int. Cl.$^7$ .................... C12N 15/40; C12N 15/82; C12N 15/84; C12N 5/04; A01H 5/00

(52) U.S. Cl. .................. 800/280; 435/69.1; 435/252.2; 435/252.3; 435/320.1; 435/414; 435/419; 435/430; 435/469; 435/475; 536/23.72; 536/24.1; 800/288; 800/294; 800/301; 800/307; 800/317

(58) Field of Search .................... 435/69.1, 252.3, 435/252.2, 320.1, 414, 419, 430, 469, 475; 536/23.72, 24.1; 800/280, 288, 294, 301, 307, 317

(56) References Cited

U.S. PATENT DOCUMENTS

| 5,349,128 A | 9/1994 | Quemada et al. |
| 5,623,066 A | 4/1997 | Quemada et al. |
| 5,633,434 A | 5/1997 | Schneider et al. |
| 5,739,082 A | 4/1998 | Donn |
| 5,792,926 A | 8/1998 | Schneider et al. |

FOREIGN PATENT DOCUMENTS

| EP | 0 412 912 A1 | 9/1990 |
| EP | 0480310 A2 | 4/1992 |
| WO | WO89/05858 | 6/1989 |
| WO | WO90/02184 | 3/1990 |
| WO | WO90/02185 | 3/1990 |
| WO | WO91/04332 | 4/1991 |

OTHER PUBLICATIONS

1979 Commonwealth Agriculture Bureau Association of Applied Biologists, Cucumber Mosaic Virus, *CMI AAB Descriptions of Plant Viruses* Jul. 1979, No. 213 (No. 1 revised).
An, Gynheung, "Development of Plant Promoter Expression Vectors and their Use for Analysis of Differential Activity of Nopaline Synthase Promoter in Transformed Tobacco Cells", *Plant Physiol.* 81:86–91 (1986).
Gould, Allan R, et al., "Cucumber Mosaic Virus RNA 3", *Eur. J. Biochem.*, 126:217–226 (Mar. 31, 1982).
Gonsalves, Dennis, et al., "Comparison of coat protein–mediated and genetically–derived resistance in cucumbers to infection by cucumber mosaic virus under filed conditions with natural challenge inoculations by vectors", *Biotechnology*, 10:1562–1570 (1992).
Quemada, Hector D., et al., "Expression of Coat Protein Gene from Cucumber Mosaic Virus Strain C. in Tobacco: Protection Against Infections by CMV Strains transmitted Mechanically or by Aphids", *Phytopathology* vol. 81(7):794–802 (1991).
Namba, Shigetou, et al., "Protection of Transgenic Plants Expressing the Coat Protein Gene of Watermelon Mosaic Virus II or Zucchini Yellow Mosaic Virus Against Six Potyviruses", *Phytopathology*, vol. 82, No. 9, pp. 940–946, 1992.
Fromm, Michael, et al., "Expression of genes transferred into monocot and dicot plant cells by electroporation", *Proc. Natl. Acad. Sci. USA*, vol. 82:5824–5828, Sep. 1985 Genetics.
Zaitlin, Milton, et al., "Specificity of Replicase–Mediated Resistance to Cucumber Mosaic Virus", *Virology* 201:200–205 (1994).
Gordon, Karl H.J., et al., "Highly PurifiedCucumber Mosaic Virus–induced RNA–Dependent RNA Polymerase Does Not Contain Any of the Full Length Translation Products of the Genomic RNSs", *Virology* 123:284–295 (1982).
Habii, N. et al., "Comparative Studies on Tomato Aspermy and Cucumber Mosaic Viruses", *Virology* 57:392–401 (1974).
Penden, K.W.C. et al., "Cucumber Mosaic Virus Contains a Functionally Divided Genome", *Virology* 53:487–492 (1973).
Bevan, Michael, et al., "Structure and transcription of the nopaline synthase gene region of I–DNA", *Nucleic Acids Research*, vol. No. 2, pp. 369–385, (1983).
Smith, C.J.S. et al., "Antisense RNA inhibition of polygalacturonase gene expression in transgenic tomatoes", *Nature* vol. 334, 25, pp. 724–726, (Aug. 1988).
Klein, T.M., et al., "High–velocity microprojectiles for delivering nucleic acids into living cells", *Nature*, 327(7):70–73, May 1987.
Alexander R. van der Krol, Peter E. Lenting, Jetty Veenstra, Ingrid M. van der Meer, Ronald E. Koes, Anton G.M. Gerats, Joseph N.M. Mol & Antoine R. Stuitje, *Nature* 333(30):866–869, Jun. 1988.
Paszkowski, Jerzy, et al., "Potykus, Direct gene transfer to plants", *IRL Press Limited*, Oxford, England, pp. 2717–2722.

(List continued on next page.)

*Primary Examiner*—David T. Fox
*Assistant Examiner*—Christopher E. Drabik
(74) *Attorney, Agent, or Firm*—Allan M. Kiang; Lisa V. Mueller

(57) ABSTRACT

CP genes of CMV strains V27, V33, V34, and A35 (CMV-V27, CMV-V33, CMV-V34, and CMV-A35 respectively) are prov

OTHER PUBLICATIONS

Tricoli, et al., "Transgenic Squash Plants Exhibit Coat Protein Mediated Protection under Field Conditions", *J. Cell Biochem. Suppl.* 16F, 222 (1992).

Tricoli, et al., "Asgrow Seed Company, Field trial results of transgenic squash and cantaloupe plants containing multiple virus resistance", *J. Cell Biochem.* Suppl. 18A, p. 91, Abstract X1–126 (1994).

Namba, Shigetou, et al., "Expression of the gene encoding the coat protein of cucumber mosaic virus (CMV) strain WL appears to provide protection to tobacco plants against infection by several different CMV strains", *Gene,* 107:181–188 (1991).

Slightom, Jerry, L., et al., "Custom polymerase–chain–reaction engineering of a plant expression vector", *Gene,* 251–255.

Hayakawa, Takaki, et al., "Nucleotide sequence analysis of cDNA encoding the coat protein of cucumber mosaic virus: genome organization and molecular features of the protein," *Gene,* 71:107–114 (1988).

Nakajiima, Midori, et al., "Protection against cucumber mosaic virus (CMV) strains 0 and Y and chrysanthemum mild mottle virus in transgenic tobacco plants expressing CMV–O coat protein", *Journal of General Virology,* 74:319–322 (1993).

Shintaku, Michael, "Coat protein gene sequences of two cucumber mosaic virus strains reveal a single amino acid change correlating with chlorosis induction", *Journal of General Virology,* 72:2587–2589 (1991).

Owen, Judith, et al., "Nucleotide sequence and evolutionary relationships of cucumber mosaic virus (CMV) strains: CMV RNA 3", *J. Gen. Virol.* 71:2243–2249 (1990).

Quemada, Hector, et al., "Nucleotide Sequences of the Coat Protein Genes and Ranking Regions of Cucumber Mosaic Virus Strains C and WL RNA3", *J. Gen. Virol.* 1065–1073 (1989).

Hayakawa, Takahiko et al., "Complete Nucleotide Sequence of RNA 3 from Cucumber Mosaic Virus (CMV) Strain 0: comparative Study of Nucleotide Sequences and Amino Acid Sequences among CMV Strains O, Q, D and Y", *J. Gen. Virol.* 70:499–504 (1989).

Clark, M.F. et al., "Characteristics of the Microplate Method of Enzyme–Linked immunosorbent Assay for the Detection of Plant Viruses", *J. Gen. Virol.* (1997) 34, 475–483.

Allmansberger, et al., "Genes for Gentamicin–(3)–N–acetyl–transferases III and IV. II. Nucleotide sequences of three AAC (3)–LH genes and Evolutionary Aspects", *Mol. Gen. Genet.* 198:514–520.

Kay, Robert, et al., "Hybrid pUC vectors for addition of new restriction enzyme sites to the ends of DNA fragments", *Nucleic Acids Research,* vol. 15, No. 6, 1987, p. 2778.

Carlberg, Carsten, et al., "Sequencing refractory GC rich regions in plasmid DNA", *Nucleic Acids Research,* vol. 15, No. 6, 1987, p. 2779.

Crossway, Anne, et al., "Integration of foreign DNA following microinjection of tobacco mesophyll protoplasts", *Mol. Gen. Genet.* (1986) 202:179–185.

EMBL ACC No. M98501 (13–8–1992).

DeBlas, C. et al., *J. Phytopathology,* 141:323–329 (1994).

Anderson et al., *Phytopathology,* 79:1284–1290 (1989).

GenBank Accession JO2059 (Aug. 2, 1993).

Cuzzo, et al., *Bio. Technology,* 6:549–557 (1988).

Nejidat, A., et al., *Physiologia Plantarum,* 80:662–668 (1990).

Section from unknown textbook, pp. 350–340, Date Unknown.

Nejidat A et al (1990) Physiologia Plantarum (80):662–668.*

Quemada et al, (1991) Phytopathology, (81):794–802.*

Wilson TMA (1993) PNAS (90) 3134–3141.*

* cited by examiner

FIG. 1A

```
  1  CCATGGACAAATCTGAATCAACCAGTGCTGGTCGTAACCGTCGGCGTCGTCCGCGTCGTG         60
        MetAspLysSerGluSerThrSerAlaGlyArgAsnArgArgArgArgProArgArgG
        M   D   K   S   E   S   T   S   A   G   R   N   R   R   R   R   P   R   R   R   G

61  GTTCCCGCTCCGCCTCCTCCTCGGATGCTAACTTTAGAGTCTTGTCGCAGCAGCTTT         120
        lySerArgSerAlaSerSerSerAspAlaAsnPheArgValLeuSerGlnGlnLeuS
        S   R   S   A   S   S   S   S   D   A   N   F   R   V   L   S   Q   Q   L   S

121  CGCGACTTAACAAGACGTTAGCAGCTGGTCGTCCAACTATTAACCACCCAACCTTTGTAG         180
        erArgLeuAsnLysThrLeuAlaAlaGlyArgProThrIleAsnHisProThrPheValG
        R   L   N   K   T   L   A   A   G   R   P   T   I   N   H   P   T   F   V   G

181  GGAGTGAACGCTGTAAACCTGGGTACACGTTCACATCTATTACCCTAAAGCCACCAAAAA         240
        lySerGluArgCysLysProGlyTyrThrPheThrSerIleThrLeuLysProProLysI
        S   E   R   C   K   P   G   Y   T   F   T   S   I   T   L   K   P   P   K   I

241  TAGACCGTGGGTCTTATTACGGTAAAAGGTTGTTATTACCTGATTCAGTCACGGAATATG         300
        leAspArgGlySerTyrTyrGlyLysArgLeuLeuLeuProAspSerValThrGluTyrA
        D   R   G   S   Y   Y   G   K   R   L   L   L   P   D   S   V   T   E   Y   D

301  ATAAGAAGCTTGTTTCGCGCATTCAAATTCGAGTTAATCCTTTGCCGAAATTTGATTCTA         360
        spLysLysLeuValSerArgIleGlnIleArgValAsnProLeuProLysPheAspSerT
        K   K   L   V   S   R   I   Q   I   R   V   N   P   L   P   K   F   D   S   T
```

FIG. 1B

```
361  CCGTGTGGGTAACAGTCCGTAAAGTTCCTGCCTCCTCGGACTTATCCGTTGCCGCCATCT  420
     hrValThrValArgLysValProAlaSerSerAspLeuSerValAlaAlaIleS
      V  W  V  T  V  R  K  V  P  A  S  S  D  L  S  V  A  A  I  S

421  CTGCTATGTTCGCGGACGGAGCCTCACCGGTACTGGTTTATCAGTATGCTGCATCTGGAG  480
     erAlaMetPheAlaAspGlyAlaSerProValLeuValTyrGlnTyrAlaAlaSerGlyV
      A  M  F  A  D  G  A  S  P  V  L  V  Y  Q  Y  A  A  S  G  V

481  TCCAAGCTAACAACAAATTGTTGTATGATCTTTCGGCATGCCGCTGATATAGGTGACA    540
     alGlnAlaAsnAsnLysLeuLeuTyrAspLeuSerAlaMetArgAlaAspIleGlyAspM
      Q  A  N  N  K  L  L  Y  D  L  S  A  M  R  A  D  I  G  D  M

541  TGAGAAAGTACGCCGTCCTCGTGTATTCAAAAGACGATGCGCTCGAGACGGACGAGCTAG  600
     etArgLysTyrAlaValLeuValTyrSerLysAspAspAlaLeuGluThrAspGluLeuV
      R  K  Y  A  V  L  V  Y  S  K  D  D  A  L  E  T  D  E  L  V

601  TACTTCATGTTGACATCGAGCACCAACGTATTCCCAGTCTGGGATGCCTCCCAGTCTGAT  660
     alLeuHisValAspIleGluHisGlnArgIleProThrSerGlyMetLeuProValEnd
      L  H  V  D  I  E  H  Q  R  I  P  T  S  G  M  L  P  V  *

661  TCCGTGTTCCCAGAACCCCTCCGATTTCTGTGGCGGAGCTGAGTTGGCAGTTCTGC      720
721  TATAAACTGTCTGAAGTCACTAAACGTTCACGGTGAACGGGTTGTCCATGG  772
```

FIG. 2A

```
1    CCATGGACAAATCTGAATCAACCAGTGCTGGTCGACGTCGTCGGCGTCGTG         60
     MetAspLysSerGluSerThrSerAlaGlyArgAsnArgArgArgProArgArgG
      M  D  K  S  E  S  T  S  A  G  R  N  R  R  R  P  R  R  G

61   GTTCCCGCTCCGTCCCGCCCCCTCCGCGGATGCCAACTTTAGAGTCTTGTCGCAGCAGTTT   120
     lySerArgSerAlaProSerSerAlaAsnPheArgValLeuSerGlnGlnLeuS
      S  R  S  A  P  S  S  A  D  A  N  F  R  V  L  S  Q  Q  L  S

121  CGCGACTTAATAAGACGTTGTCAGCTGGTCGTCCAACTATTAACCACCCAACCTTTGTAG    180
     erArgLeuAsnLysThrLeuSerAlaGlyArgProThrIleAsnHisProThrPheValG
      R  L  N  K  T  L  S  A  G  R  P  T  I  N  H  P  T  F  V  G

181  GGAGTGAGCGTTGTAAATCTGGTACACGTTCACATCTATTACCCTAAAGCGCCGAAAA      240
     lySerGluArgCysLysSerGlyTyrThrPheThrSerIleThrLeuLysProProLysI
      S  E  R  C  K  S  G  Y  T  F  T  S  I  T  L  K  P  P  K  I

241  TAGACCGTGGGTCTTATTATGGTAAAAGGTTGTTATTACCTGATTCAGTCACAGAATATG   300
     leAspArgGlySerTyrTyrGlyLysArgLeuLeuLeuProAspSerValThrGluTyrA
      D  R  G  S  Y  Y  G  K  R  L  L  L  P  D  S  V  T  E  Y  D

301  ATAAGAAACTTGTTCGCGATCCATTCAAATTCGAGTTAATCCCTTGCCGAAATTTGATTCTA   360
     spLysLysLeuValSerArgIleGlnIleArgValAsnProLeuProLysPheAspSerT
      K  K  L  V  S  R  I  Q  I  R  V  N  P  L  P  K  F  D  S  T

361  CCGTGTGGGTGACAGTCCGTAAAGTTCCTGCCTCCTCGGACTTATCCGTTGCCGCCATCT   420
     hrValTrpValThrValArgLysValProAlaSerSerAspLeuSerValAlaAlaIleS
      V  W  V  T  V  R  K  V  P  A  S  S  D  L  S  V  A  A  I  S
```

FIG. 2B

```
421  CTGCTATGTTTGCGGACGGAGCCTCACCGGTACTGGTTTATCAGTACGCTGCATCTGGAG    480
     erAlaMetPheAlaAspGlyAlaSerProValLeuValTyrGlnTyrAlaAlaSerGlyV
      A  M  F  A  D  G  A  S  P  V  L  V  Y  Q  Y  A  A  S  G  V

481  TCCAAGCTAACAACAAATTGTTGTATGATCTTTCGGCATGCGCCTGATATAGGCGACA     540
     alGlnAlaAsnAsnLysLeuLeuTyrAspLeuSerAlaMetArgAlaAspIleGlyAspM
      Q  A  N  N  K  L  L  Y  D  L  S  A  M  R  A  D  I  G  D  M

541  TGAGAAAGTACGCCGTCCTCGTGTATTCAAAAGACGATGCACTCGAGACGGACGAGCTAG   600
     etArgLysTyrAlaValLeuValTyrSerLysAspAspAlaLeuGluThrAspGluLeuV
      R  K  Y  A  V  L  V  Y  S  K  D  D  A  L  E  T  D  E  L  V

601  TACTTCATGTTGACGTCGAGCACCAACGCATTCCCACGTCTGGGGTGCTCCCAGTATAAT   660
     alLeuHisValAspValGluHisGlnArgIleProThrSerGlyValLeuProValEnd
      L  H  V  D  V  E  H  Q  R  I  P  T  S  G  V  L  P  V  *

661  TCTGTGCTTTCCAGAACCCTCCCTCCGATTTCTGTGGCGGGAGCTGAGTTGGCAGTTCTG   720

721  CTGTAAACTGTCTGAAGTCACTAAACGTTTTACGGTGAACGGGTTGTCCATGG    773
```

FIG. 3

```
  1  CCATGGACAAATCTGAATCAACCAGTGCTGGTCGTAACCGTCGACGTCGTTCCCGCTGCGTTCCCGCTCCTCCTCTTCGGATGCGTAACTTTAG  100
        MetAspLysSerGluSerThrSerAlaGlyThrSerAlaArgArgArgArgProArgArgSerAlaSerSerSerAspAlaAsnPheAr
        M  D  K  S  E  S  T  S  A  G  R  N  R  R  R  R  P  R  R  G  S  R  S  A  S  S  S  D  A  N  F  R

101  AGTCTTGTCGCAGCAGCTTCGGGACTTAACAAGACGTTAGCAGCTGGTCGTCCAACTATTAACCACCAACCTTTGTAGGAGTGAACGCTGTAGACCT  200
        gValLeuSerGlnGlnLeuSerArgLeuAsnLysThrLeuAlaAlaGlyArgProThrIleAsnHisProThrPheValGlySerGluArgCysArgPro
        V  L  S  Q  Q  L  S  R  L  N  K  T  L  A  A  G  R  P  T  I  N  H  P  T  F  V  G  S  E  R  C  R  P

201  GGGTACACGTTCACATCTATTACCTAAAGCCACCAAAAATAGACCCGGGTCTTACTACGGTAAAGGTTGTTACTACCTGATTCAGTCACGGAATATG  300
        GlyTyrThrPheThrSerIleThrLysProProLysIleAspArgGlySerTyrTyrGlyLysArgLeuLeuLeuProAspSerValThrGluTyrA
        G  Y  T  F  T  S  I  T  L  K  P  P  K  I  D  R  G  S  Y  Y  G  K  R  L  L  L  P  D  S  V  T  E  Y  D

301  ATAAGAAGCTTGTTTCGCGCATTCAAATTCGAGTTAATCCTTTGCCGAAATTGATTCTACCGTGGGTGACAGTTCCTGCCTCCTCGGA  400
        spLysLysLeuValSerArgIleGlnIleArgValAsnProLeuProLysPheAspSerThrValTrpValThrValArgLysValProAlaSerSerAs
        K  K  L  V  S  R  I  Q  I  R  V  N  P  L  P  K  F  D  S  T  V  W  V  T  V  R  K  V  P  A  S  S  D

401  CTTATCCGTTGCCGCCATCTCTGCTATGTTCGCGGACGGAGCCTCACCGGTACTGGTTTATCAGTATGCGCATCTGGAGTTCAAGCTAACAACAAATTG  500
        pLeuSerValAlaAlaIleSerAlaMetPheAlaAspGlyAlaSerProValLeuValTyrGlnTyrAlaAlaSerGlyValGlnAlaAsnAsnLysLeu
        L  S  V  A  A  I  S  A  M  F  A  D  G  A  S  P  V  L  V  Y  Q  Y  A  A  S  G  V  Q  A  N  N  K  L

501  TTGTATGATCTTTCGGCGATGCGCCTGATATAGGTGACATGAGAAAGTACGCCGTCCTCGTATTCAAAAGACGATGCACTCGAGACGACGAGCTAG  600
        LeuTyrAspLeuSerAlaMetArgAlaAspIleGlyAspMetArgLysTyrAlaValLeuValTyrSerLysAspAspAlaLeuGluThrAspGluLeuV
        L  Y  D  L  S  A  M  R  A  D  I  G  D  M  R  K  Y  A  V  L  V  Y  S  K  D  D  A  L  E  T  D  E  L  V

601  TACTTCATGTTGACATCGAGCACCAACGCCATTCCCACGTGCTGCGTCCCAGTTGATTCCGTGTTCCAGAACCCTCCGATTCTGTGGCGGGA  700
        alLeuHisValAspIleGluHisGlnArgIleProThrSerGlyValLeuProValEnd
        L  H  V  D  I  E  H  Q  R  I  P  T  S  G  V  L  P  V  *

701  GCTGAGTGGCAGTTCTGCTATAAACTGTCTGAAGTCACTAAACGTTTACGGTGAACGGTTGTGCCATGG  771
```

FIG. 4A

```
            RMM351              NcoI
         5' CGTAGAATTCAGTCG  AGCCATGGAC  3'
  V27cp   ..........         ..CCATGGAC  AAATCTGAAT  CAACCAGTGC  TGGTCGTAAC  CGTCGGCGTC
  V33cp   ..........         ..CCATGGAC  AAATCTGAAT  CAACCAGTGC  TGGTCGTAAC  CGTCGACGTC
 Cmvv34   ..........         ..CCATGGAC  AAATCTGAAT  CAACCAGTGC  TGGTCGTAAC  CGTCGACGTC
    Ccp   AATTGAGTCG         AGTCATGGAC  AAATCTGAAT  CAACCAGTGC  TGGTCGTAAC  CATCGACGTC
  Cmvwl   GTCTTAGTGT         GCCTATGGAC  CTCCCAATGC  CTCCCTCGGA  TAGTAGAACC  TCCCGGCGTC
                                                                                   420

421
  V27cp   GTCCGCGTCG  TGGTTCCCGC  TCCGCCTCCT  CCTCCTCGGA  TGCTAACTTT  AGAGTCTTGT
  V33cp   GTCCGCGTCG  TGGTTCCCGC  TCCGCCCCCT  CCTCCGCGGA  TGCCAACTTT  AGAGTCTTGT
 Cmvv34   GTCCGCGTCG  TGGTTCCCGC  TCCGCCTTCT  CCTCTTCGGA  TGCTAACTTT  AGAGTCTTGT
    Ccp   GTCCGCGTCG  TGGTTCCCGC  TCCGCCCCCG  CCTCCGCGGA  TGCTAACTTT  AGAGTCTTGT
  Cmvwl   GTCGCCCGCG  TAGAGGTTCT  CGGTCCCGCTT  CTGGTCGCGA  TGCAGGGTTG  CGTGCTTTGA
                                                                                   480

481
  V27cp   CGCAGCAGCT  TTCGCGACTT  AACAAGAGACGT  TAGCAGCTGG  TCGTCCAACT  ATTAACCACC
  V33cp   CGCAGCAGCT  TTCGCGACTT  AATAAGAGACGT  TGTCAGCTGG  TCGTCCAACT  ATTAACCACC
 Cmvv34   CGCAGCAGCT  TTCGCGACTT  AACAAGAGACGT  TAGCAGCTGG  TCGTCCAACT  ATTAACCACC
    Ccp   CGCAGCAGCT  TTCGCGACTT  AATAGAACCC   TCGCCATTGG  TCGTCCCACT  CTTAACCACC
  Cmvwl   CTCAGCAGAT  GCTGAAACTC  AATAGAACCC   TCGCCATTGG  TCGTCCCACT  CTTAACCACC
                                                                                   540

541
  V27cp   CAACCTTTGT  AGGGAGTGAA  CGCTGTAAAC  CTGGGTACAC  GTTCACATCT  ATTACCCTAA
  V33cp   CAACCTTTGT  AGGGAGTGAG  CGTTGTAAAT  CTGGGTACAC  GTTCACATCT  ATTACCCTAA
 Cmvv34   CAACCTTTGT  AGGGAGTGAA  CGCTGTAGAC  CTGGGTACAC  GTTCACATCT  ATTACCCTAA
    Ccp   CAACCTTTGT  AGGGAGTGAA  CGCTGTAAAC  CTGGGTACAC  GTTCACATCT  ATTACCCTAA
  Cmvwl   CAACCTTCGT  GGGTAGTGAA  AGCTGTAAAC  CCGGTTACAC  TTTCACATCT  ATTACCCTGA
                                                                                   600
```

FIG. 4B

```
        601
V27cp   AGCCACCAAA AATAGACCGT GGGTCTTATT ACGGTAAAAG GTTGTTATTA CCTGATTCAG
V33cp   AGCCGCCGAA AATAGACCGT GGGTCTTATT ATGGTAAAAG GTTGTTATTA CCTGATTCAG
Cmvv34  AGCCACCAAA AATAGACCGC GGGTCTTACT ACGGTAAAAG GTTGTTACTA CCTGATTCAG
Ccp     AGCCACCAAA AATAGACCGT GAGTCTTATT ACGGTAAAAG GTTGTTACTA CCTGATTCAG
Cmvwl   AACCGCCTGA AATTGAGAAA GGTTCATATT TTGGTAGAAG GTTGTCTTTG CCAGATTCAG
                                                                        660

661
V27cp   TCACGGAATA TGATAAGAAG CTTGTTTCGC GCATTCAAAT TCGAGTTAAT CCTTTGCCGA
V33cp   TCACAGAATA TGATAAGAAA CTTGTTTCGC GCATTCAAAT TCGAGTTAAT CCCTTGCCGA
Cmvv34  TCACGGAATA TGATAAGAAG CTTGTTTCGC GCATTCAAAT TCGAGTTAAT CCTTTGCCGA
Ccp     TCACGGAATA TGATAAGAAG CTTGTTTCGC GCATTCAAAT TCGAGTTAAT CCTTTGCCGA
Cmvwl   TCACGGACTA TGATAAGAAG CTTGTTTCGC GCATTCAAAT CAGGGTTAAT CCTTTGCCGA
                                                                        720

721
V27cp   AATTTGATTC TACCGTGTGG GTAACAGTCC GTAAAGTTCC TGCCTCCTCG GACTTATCCG
V33cp   AATTTGATTC TACCGTGTGG GTGACAGTCC GTAAAGTTCC TGCCTCCTCG GACTTATCCG
Cmvv34  AATTTGATTC TACCGTGTGG GTGACAGTTC GTAAAGTTCC TGCCTCCTCG GACTTATCCG
Ccp     AATTTGATTC TACCGTGTGG GTGACAGTCC GTAAAGTTCC TGCCTCCTCG GACTTATCCG
Cmvwl   AATTTGATTC TACCGTGTGG GTTACAGTTC GGAAAGTACC TTCATCATCC GATCTTTCCG
                                                                        780

781
V27cp   TTGCCGCCAT CTCTGCTATG TTCGCGGACG GAGCCTCACC GGTACTGGTT TATCAGTATG
V33cp   TTGCCGCCAT CTCTGCTATG TTTGCGGACG GAGCCTCACC GGTACTGGTT TATCAGTACG
Cmvv34  TTGCCGCCAT CTCTGCTATG TTCGCGGACG GAGCCTCACC GGTACTGGTT TATCAGTATG
Ccp     TTGCCGCCAT CTCTGCTATG TTCGCGGACG GAGCCTCACC GGTACTGGTT TATCAGTATG
Cmvwl   TCGCCGCCAT CTCTGCTATG TTTGGCGATG GTAATTCACC GGTTTTGGTT TATCAGTATG
                                                                        840
```

FIG. 4C

```
        841
V27cp   CTGCATCTGG AGTCCAAGCT AACAACAAAT TGTTGTATGA TCTTTCGGCG ATGCGCGCTG
V33cp   CTGCATCTGG AGTCCAAGCT AACAACAAAT TGTTGTATGA TCTTTCGGCG ATGCGCGCTG
Cmvv34  CTGCATCTGG AGTCCAAGCT AACAACAAAT TGTTGTATGA TCTTTCGGCG ATGCGCGCTG
Ccp     CCGCATCTGG AGTCCAAGCC AACAACAAAC TGTTGTTTGA TCTTTCGGCG ATGCGCGCTG
Cmvw1   CTGCGTCCGG AGTTCAGGCC AACAATAAGT TACTTTATGA CCTGTCCGAG ATGCGTGCTG
                                                                      900

901
V27cp   ATATAGGTGA CATGAGAAAG TACGCCCGTCC TCGTGTATTC AAAAGACGAT GCGCTCGAGA
V33cp   ATATAGGCGA CATGAGAAAG TACGCCCGTCC TCGTGTATTC AAAAGACGAT GCACTCGAGA
Cmvv34  ATATAGGTGA CATGAGAAAG TACGCCCGTCC TCGTGTATTC AAAAGACGAT GCACTCGAGA
Ccp     ATATAGGTGA CATGAGAAAG TACGCCCGTCC TCGTGTATTC AAAAGACGAT GCGCTCGAGA
Cmvw1   ATATCGGCGA CATGCGTAAG TACGCCGTCG TGGTTTACTC GAAAGACGAT AAACTAGAGA
                                                                      960

961
V27cp   CGGACGAGCT AGTACTTCAT GTTGACATCG AGCACCAACG TATTCCCACG TCTGGGATGC
V33cp   CGGACGAGCT AGTACTTCAT GTTGACGTCG AGCACCAACG CATTCCCACG TCTGGGGTGC
Cmvv34  CGGACGAGCT AGTACTTCAT GTTGACATCG AGCACCAACG CATTCCCACG TCTGGGGTGC
Ccp     CGGACGAGCT AGTACTTCAT GTTGACATCG AGCACCAACG CATTCCCACA TCTGGAGTGC
Cmvw1   AGGACGAGAT TGCACTTCAT GTCGACGTCG AGCATCAACG AATTCCTATC TCACGGATGC
                                                                     1020

1021
V27cp   TCC....... ..CAGTCTGA TTCCGTG.TT CCCAGAACCC T.CCCTCCGA TTTCTGTGGC
V33cp   TCC....... ..CAGTATAA TTCTGTGCTT TCCAGAACCC TCCCTCCGA  TTTCTGTGGC
Cmvv34  TCC....... ..CAGTTTGA TTCCGTG.TT .CCAGAACCC T.CCCTCCGA TTTCTGTGGC
Ccp     TCC....... ..CAGTCTGA TTCCGTG.TT CCCAGAACCC T.CCCTCCGA TCTCTGTGGC
Cmvw1   TCCCGACTTA GTCCGTGTGT TTACCGGGCT CCGAGAACGT TAAACTACAC TCTCAATCGC
                                                                     1080
```

FIG. 4D

```
          1081                                                              1140
V27cp     GGGAGCTGAG TTGGCAGTTC TGCTATAAAC TGTCTGAAGT CACTAAACGT .....TTCACG
V33cp     GGGAGCTGAG TTGGCAGTTC TGCTGTAAAC TGTCTGAAGT CACTAAACGT .....TTTACG
Cmvv34    GGGAGCTGAG TTGGCAGTTC TGCTATAAAC TGTCTGAAGT CACTAAACGT .....TTTACG
Ccp       GGGAGCTGAG TTGGCAGTTC TACTACAAAC TGTCTGGAGT CACTAAACGT .....TTTACG
Cmvw1     GAGTGCTGAC TTGGTAGTAT TGCTTCAAAC TGCCTGAAGT CCCTAAACGT GTTGTTGCGC 1141                                                              1200
V27cp     GTGAACGGGT TGTCCATGG
V33cp     GTGAACGGGT TGTCCATGG
Cmvv34    GTGAACGGGT TGTCCATGG
Ccp       GTGAACGGGT TGTCCATCCA GCTTACGGCT
Cmvw1     GGGAACGGG  TGTCCATCCA GCTTACGGCT
RMM352-->3'          CAGGTACCT CGAATGCCGAGCTCACCAG 5'
                     Nco I
```

FIG. 5A

```
                                                          *           *                     *50
         1
Cmvv34   MDKSESTSAG R.NRRRRPRR GSRSASSSSD ANFRVLSQQL SRLNKTLAAG
Cmvv27   MDKSESTSAG R.NRRRRPRR GSRSASSSSD ANFRVLSQQL SRLNKTLAAG
Cmvc     MDKSESTSAG R.NHRRRPRR GSRSAPSSAD ANFRVLSQQL SRLNKTLAAG
V33cp    MDKSESTSAG R.NRRRRPRR GSRSAPSSAD ANFRVLSQQL SRLNKTLSAG
Cmvq3    MDKSGSPNAS RTSRRRRPRR GSRSA.SGAD AGLRALTQQM LRLNKTLAIG
Cmvw1    MDKSGSPNAS RTSRRRRPRR GSRSA.SGAD AGLRALTQQM LKLNRTLAIG

**          *                                100
         51
Cmvv34   RPTINHPTFV GSERCRPGYT FTSITLKPPK IDRGSYYGKR LLLPDSVTEY
Cmvv27   RPTINHPTFV GSERCKPGYT FTSITLKPPK IDRGSYYGKR LLLPDSVTEY
Cmvc     RPTINHPTFV GSERCRPGYT FTSITLKPPK IDRESYYGKR LLLPDSVTEY
V33cp    RPTINHPTFV GSERCKSGYT FTSITLKPPK IDRGSYYGKR LLLPDSVTEY
Cmvq3    RPTLNHPTFV GSESCKPGYT FTSITLKPPE IEKGSYFGRR LSLPDSVTDY
Cmvw1    RPTLNHPTFV GSESCKPGYT FTSITLKPPE IEKGSYFGRR LSLPDSVTDY 150
         101
Cmvv34   DKKLVSRIQI RVNPLPKFDS TVWVTVRKVP ASSDLSVAAI SAMFADGASP
Cmvv27   DKKLVSRIQI RVNPLPKFDS TVWVTVRKVP ASSDLSVAAI SAMFADGASP
Cmvc     DKKLVSRIQI RVNPLPKFDS TVWVTVRKVP ASSDLSVAAI SAMFADGASP
V33cp    DKKLVSRIQI RVNPLPKFDS TVWVTVRKVP ASSDLSVAAI SAMFADGASP
Cmvq3    DKKLVSRIQI RINPLPKFDS TVWVTVRKVP SSSDLSVAAI SAMFGDGNSP
Cmvw1    DKKLVSRIQI RVNPLPKFDS TVWVTVRKVP SSSDLSVAAI SAMFGDGNSP
```

FIG. 5B

```
         151                    *                                              200
Cmvv34   VLVYQYAASG  VQANNKLLYD  LSAMRADIGD  MRKYAVLVYS  KDDALETDEL
Cmvv27   VLVYQYAASG  VQANNKLLYD  LSAMRADIGD  MRKYAVLVYS  KDDALETDEL
Cmvc     VLVYQYAASG  VQANNKLLED  LSAMRADIGD  MRKYAVLVYS  KDDALETDEL
V33cp    VLVYQYAASG  VQANNKLLYD  LSAMRADIGD  MRKYAVLVYS  KDDALETDEL
Cmvq3    VLVYQYAASG  VQANNKLLYD  LSEMRADIGD  MRKYAVLVYS  KDDKLEKDEI
Cmvw1    VLVYQYAASG  VQANNKLLYD  LSEMRADIGD  MRKYAVLVYS  KDDKLEKDEI 201        *                        *                                 250
Cmvv34   VLHVDIEHQR  IPTSGVLPV*
Cmvv27   VLHVDIEHQR  IPTSGMLPV*
Cmvc     VLHVDIEHQR  IPTSGVLPV*
V33cp    VLHVDVEHQR  IPTSGVLPV*
Cmvq3    VLHVDVEHQR  IPISRMLPT*
Cmvw1    ALHVDVEHQR  IPISRMLPT*
```

FIG. 8

```
CCATGGACAAATCTGAATCAACCAGTGCTGGTCGTGTAACCGTCGACGTCGTCCGCGTCGTG   60
 A  M  D  K  S  E  S  T  S  A  G  R  N  R  R  R  R  P  R  R
GTTCCCGCTCCGCCCCTCTCCGCGGATGCTAACTTGTTAGAGTCCTGTCTCGCAGCAGCTTT  120
 G  S  R  S  A  L  S  S  A  D  A  N  F  R  V  L  S  Q  Q  L
CGCGACTTAATAAGAGACGTTAGCAGCTGGTCGTCCAACTATTAACCACCCAACCTTGTAG  180
 S  R  L  N  K  T  L  A  A  G  R  P  T  I  N  H  P  T  F  V
GGAGTGAACGCTGTAGACCTGGGTACACGTTCACATCTATTACCCTAAAGCCACCAAAAA   240
 G  S  E  R  C  R  P  G  Y  T  F  T  S  I  T  L  K  P  P  K
TAGACCGTGGGTCTTATTACGGTAAAAGGTTGTTACTACCTGATTCAGTCACAGAATATG   300
 I  D  R  G  S  Y  Y  G  K  R  L  L  P  D  S  V  T  E  Y
ATAAGAAGCTTGTTTCGCGCATTCAAATTCGAGTTAATCCTTTGCCGAAATTTGATTCTA   360
 D  K  L  V  S  R  I  Q  I  R  V  N  P  L  P  K  F  D  S
CCGTGTGGGTGACAGTCCGTAAAGTTCCCTCCGGACTTATCCGTTGCCGCCATCT   420
 T  V  W  V  T  V  R  K  V  P  A  S  S  D  L  S  V  A  A  I
CTGCTATGTTCGCGGACGGAGCCTCACCGGTACTGGTTTATCAGTATGCCGCATCTGGAG   480
 S  A  M  F  A  D  G  A  S  P  V  L  V  Y  Q  Y  A  A  S  G
TCCAAGCCAACAACAAACTGTTGTATGATCTTTCGGCTGCCTGATGCGCTGATATAGGTGACA   540
 V  Q  A  N  N  K  L  L  Y  D  L  S  A  M  R  A  D  I  G  D
TGAGAAAGTACGCCGTCCTCCTCGTGTATTCAAAAGACGATTCCCACGTCCTGAGTGCTCCCAGCTAG   600
 M  R  K  Y  A  V  L  V  Y  S  K  D  D  A  L  E  T  D  E  L
TACTTCATGTTGACATCGAGCACCAACGCATTCCCACGTCTCCCAGTCTGTCCCAGTCTGAT   660
 V  L  H  V  D  I  E  H  Q  R  I  P  T  S  G  V  L  P  V  .
TCTGTGTTCCCAGAACCCTCCCGATCTCTGTGGCGGGAGCTGTCAGTTGGCAGTTCTGC   720
 F  C  V  P  R  T  L  P  P  I  S  V  A  G  A  E  L  A  V  L
TGTAAACTGTCTGAAGTCACTAAACGTTTTACGGTCAACGGGTTGTCCATGG   772
 L  .  T  V  .  S  H  .  T  F  F  Y  G  E  R  V  V  H  G
```

FIG. 9A

|   | | | | | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
|   | M | D | K | S | E | S | T | S | A | G | R | - | N | R | R | R | P | R | R | G | S | R | S | A | S | S | S | A | D | A | N | F | R | V | L | S | Q | Q | L | | Majority |
|   | | | | | | | | | 10 | | | | | | | | | 20 | | | | | | | | | 30 | | | | | | | | | 40 | | | |   |
| 1 | M | D | K | S | E | S | T | S | A | G | R | - | N | H | R | R | P | R | R | G | S | R | S | A | S | S | AP | A | D | A | N | F | R | V | L | S | Q | Q | L | | CMV C AA SEQ |
| 1 | M | D | K | S | E | S | T | S | A | G | R | - | N | R | R | R | P | R | R | G | S | R | S | A | L | S | S | A | D | A | N | F | R | V | L | S | Q | Q | L | | CMV CARNA5 AA SEQ |
| 1 | M | D | K | S | E | S | T | S | A | G | R | - | N | R | R | R | P | R | R | G | S | R | S | A | S | S | S | S | D | D | A | N | F | R | V | L | S | Q | Q | L | | CMV V27 AA SEQ |
| 1 | M | D | K | S | E | S | T | S | A | G | R | - | N | R | R | R | P | R | R | G | S | R | S | A | S | S | AP | A | D | A | N | F | R | V | L | S | Q | Q | L | | CMV V33 AA SEQ |
| 1 | M | D | K | S | E | S | T | S | A | G | R | - | N | R | R | R | P | R | R | G | S | R | S | A | S | S | S | A | D | A | N | F | R | V | L | S | Q | Q | L | | CMV V34 AA SEQ |
| 1 | M | D | K | S | G | PN | A | S | R | T S | R | R | R | R | R | P | R | R | G | S | R | S | A | - | S | G | A | D | A | G L | R | A | L | T | Q | Q | M | | | CMV WL AA SEQ |

|   | | | | | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
|   | S | R | L | N | K | T | L | A | A | G | R | P | T | I | N | H | P | T | F | V | G | S | E | R | C | K | P | G | Y | T | F | T | S | I | T | L | K | P | P | K | | Majority |
|   | | | | | | | | | 50 | | | | | | | | | 60 | | | | | | | | | 70 | | | | | | | | | 80 | | | |   |
| 40 | S | R | L | N | K | T | L | A | A | G | R | P | T | I | N | H | P | T | F | V | G | S | E | R | C | R | P | G | Y | T | F | T | S | I | T | L | K | P | P | K | | CMV C AA SEQ |
| 40 | S | R | L | N | K | T | L | A | A | G | R | P | T | I | N | H | P | T | F | V | G | S | E | R | C | R | P | G | Y | T | F | T | S | I | T | L | K | P | P | K | | CMV CARNA5 AA SEQ |
| 40 | S | R | L | N | K | T | L | A | A | G | R | P | T | I | N | H | P | T | F | V | G | S | E | R | C | K | P | G | Y | T | F | T | S | I | T | L | K | P | P | K | | CMV V27 AA SEQ |
| 40 | S | R | L | N | K | T | L | S | A | G | R | P | T | I | N | H | P | T | F | V | G | S | E | R | C | K | S G | G | Y | T | F | T | S | I | T | L | K | P | P | K | | CMV V33 AA SEQ |
| 40 | S | R | L | N | K | T | L | A | A | G | R | P | T | I | N | H | P | T | F | V | G | S | E | R | C | K | P | G | Y | T | F | T | S | I | T | L | K | P | P | K | | CMV V34 AA SEQ |
| 40 | L K | K | L | N | R T | T | L | A | I | G | R | P | T | I | L | P | T | F | V | G | S | E | S | C | K | P | G | Y | T | F | T | S | I | T | L | K | P | P | E | | | CMV WL AA SEQ |

|   | | | | | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
|   | I | D | R | G | S | Y | Y | G | K | R | L | L | L | P | D | S | V | T | E | Y | D | K | K | L | V | S | R | I | Q | I | R | V | N | P | L | P | K | F | D | S | | Majority |
|   | | | | | | | | | 90 | | | | | | | | | 100 | | | | | | | | | 110 | | | | | | | | | 120 | | | |   |
| 80 | I | D | R | G | S | Y | Y | G | K | R | L | L | L | P | D | S | V | T | E | Y | D | K | K | L | V | S | R | I | Q | I | R | V | N | P | L | P | K | F | D | S | | CMV C AA SEQ |
| 80 | I | D | R | G | S | Y | Y | G | K | R | L | L | L | P | D | S | V | T | E | Y | D | K | K | K | L | V | S | R | I | Q | I | R | V | N | P | L | P | K | F | D | S | | CMV CARNA5 AA SEQ |
| 80 | I | D | R | G | S | Y | Y | G | K | R | L | L | L | P | D | S | V | T | E | Y | D | K | K | L | V | S | R | I | Q | I | R | V | N | P | L | P | K | F | D | S | | CMV V27 AA SEQ |
| 80 | I | D | R | G | S | Y | Y | G | K | R | L | L | L | P | D | S | V | T | E | Y | D | K | K | L | V | S | R | I | Q | I | R | V | N | P | L | P | K | F | D | S | | CMV V33 AA SEQ |
| 80 | I | D | R | G | S | Y | Y | G | K | R | L | L | L | P | D | S | V | T | E | Y | D | K | K | L | V | S | R | I | Q | I | R | V | N | P | L | P | K | F | D | S | | CMV V34 AA SEQ |
| 80 | I E | K | G | S | Y | F | G | R R | R | L | S L | L | P | D | S | V | T | D | Y | D | K | K | L | V | S | R | I | Q | I | R | V | N | P | L | P | K | F | D | S | | | CMV WL AA SEQ |

FIG. 9B

```
      T V W V T V R K V P A S S D L S V A A I S A M F A D G A S P V L V Y Q Y A A S G    Majority
                    130                 140                 150                 160
120   T V V V T V R K K V P A S S D L S V A A I S A M F A D G A S P V L V Y Q Y A A S G    CMV C AA SEQ
120   T V V V T V R K V V P A S S D L S V A A I S A M F A D G A S P V L V Y Q Y A A S G    CMV CARNA5 AA SEQ
120   T T V W T V R R K V P A S S D L S V A A I S A M F A D G A S P V L V Y Q Y A A S G    CMV V27 AA SEQ
120   T T V V T V R K K V P A S S D L S V A A I S A M F A D G A S P V L V Y Q Y A A S G    CMV V33 AA SEQ
120   T T V V T V R K K V P A S S D L S V A A I S A M F A D G A S P V L V Y Q Y A A S G    CMV V34 AA SEQ
120   T T V W T V R K V P [S] S S D L S V A A I S A M F [G] D G [N] S P V L V Y Q Y A A S G    CMV WL AA SEQ V Q A N N K L L Y D L S A M R A D I G D M R K K Y A V L V Y S K D D A L E T D E L    Majority
                    170                 180                 190                 200
160   V Q A N N K L L Y D L S A M R A D I G D M R K K Y A V L V Y S K D D A L E T D E L    CMV C AA SEQ
160   V V A N N K L L Y D L S A M R A D I G D M R K K Y A V L V Y S K D D A L E T D E L    CMV CARNA5 AA SEQ
160   V Q Q N N K L L Y D L S A M R A D I G D M R K K Y A V L V Y S K D D A L E T D E L    CMV V27 AA SEQ
160   V V A N N K L L Y D L S A M R A D I G D M R K K Y A V L V Y S K D D A L E T D E L    CMV V33 AA SEQ
160   V V A N N K L L Y D L S A M R A D I G D M R K K Y A V L V Y S K D D A L E T D E L    CMV V34 AA SEQ
160   V Q A N N K L L Y D L S [E] M R A D I G D M R K K Y A V L V Y S K D D [K] L E [K] D E [I]    CMV WL AA SEQ V L H V D I E H Q R I P T S G V L P V -                                              Majority
                    210                 220
200   V L H V D I E H Q R I P T S G V L P V                                                CMV C AA SEQ
200   V L H V D I E H Q R I P T S G V L P V                                                CMV CARNA5 AA SEQ
200   V L H V D I E H Q R I P T S G V L P V                                                CMV V27 AA SEQ
200   V L H H D I E H Q R I P T S G [M] L P V                                              CMV V33 AA SEQ
200   V L H V D [V] E H Q R I P T S G V L P V                                              CMV V34 AA SEQ
200   L [A] H V D [V] E H Q R I P [S] R M L P [T]                                          CMV WL AA SEQ
```

FIG. 10A

```
        X X X X X X X X X X X X X X X X X X X X    Majority
                    330              340
                     |                |
  1     . . . . . . . . . . . . . . . . . . . .    carna5 cp cpexp33.seq
321     T A G A G A G T G T G T G C T G T G         New ccp.seq15
  1     . . . . . . . . . . . . . . . . . . . .    New cmvv34.seq5
247     . . . . . . . . T G A G T C G T G T G       New cmvw1.seq1
  1     . . . . . . . . . . . . . . . . . . . .    New v27cp.seq5
  1     . . . . . . . . . . . . . . . . . . . .    New v33cp.seq8

X X X X X X X X X X X X X X X X X X X X    Majority
                    350              360
                     |                |
  1     . . . . . . . . . . . . . . . . . . . .    carna5 cp cpexp33.seq
341     T T T T C T C T T T T G T G T C G T A G     New ccp.seq15
  1     . . . . . . . . . . . . . . . . . . . .    New cmvv34.seq5
258     T T T T G T A T T T T G C G T C T T A G     New cmvw1.seq1
  1     . . . . . . . . . . . . . . . . . . . .    New v27cp.seq5
  1     . . . . . . . . . . . . . . . . . . . .    New v33cp.seq8

X X X X X X X X X X X X C C A T G G A C    Majority
                    370              380
                     |                |
  1     . . . . . . . . . . . .[C C A T G G A C]   carna5 cp cpexp33.seq
361     A A T T G A G T C G A G[T]C A T G G A C    New ccp.seq15
  1     . . . . . . . . . . . .[C C A T G G A C]   New cmvv34.seq5
278     . . . T G T G C . . . . C[T]A T G G A C    New cmvw1.seq1
  1     . . . . . . . . . . . .[C C A T G G A C]   New v27cp.seq5
  1     . . . . . . . . . . . .[C C A T G G A C]   New v33cp.seq8

A A A T C T G A A T C A A C C A G T G C    Majority
                    390              400
                     |                |
  9    [A A A T C T G A A T C A A C C A G T G C]   carna5 cp cpexp33.seq
381   [A A A T C T G A A T C A A C C A G T G C]    New ccp.seq15
  9    [A A A T C T G A A T C A A C C A G T G C]   New cmvv34.seq5
291   [A A A T C T G[G]A T C[T C]C C A[A]T G C]    New cmvw1.seq1
  9    [A A A T C T G A A T C A A C C A G T G C]   New v27cp.seq5
  9    [A A A T C T G A A T C A A C C A G T G C]   New v33cp.seq8
```

FIG. 10B

```
     T G G T C G T A A C C G T C G A C G T C   Majority
                     410                 420

29  T G G T C G T A A C C G T C G A C G T C   carna5 cp cpexp33.seq
401  T G G T C G T A A C C A T C G A C G T C   New ccp.seq15
 29  T G G T C G T A A C C G T C G A C G T C   New cmvv34.seq5
311  T A G T A G A A C T C C C G G C G T C     New cmvw1.seq1
 29  T G G T C G T A A C C G T C G G C G T C   New v27cp.seq5
 29  T G G T C G T A A C C G T C G A C G T C   New v33cp.seq8

G T C X X X C G C G T C G T G G T T C C   Majority
                     430                 440

49  G T C . . . C G C G T C G T G G T T C C   carna5 cp cpexp33.seq
421  G T C . . . C G C G T C G T G G T T C C   New ccp.seq15
 49  G T C . . . C G C G T C G T G G T T C C   New cmvv34.seq5
331  G T C G C C C G C G T A G A G G T T C T   New cmvw1.seq1
 49  G T C . . . C G C G T C G T G G T T C C   New v27cp.seq5
 49  G T C . . . C G C G T C G T G G T T C C   New v33cp.seq8

C G C T C C G C C C C C T C C T C C G C   Majority
                     450                 460

66  C G C T C C G C C C T C T C C T C C G C   carna5 cp cpexp33.seq
438  C G C T C C G C C C C C T C C T C C G C   New ccp.seq15
 66  C G C T C C G C T T C C T C C T C T T C   New cmvv34.seq5
351  C G G T C C G C T . . . T C T G G T G C   New cmvw1.seq1
 66  C G C T C C G C C T C T T C C T C C T C   New v27cp.seq5
 66  C G C T C C G C C C C C T C C T C C G C   New v33cp.seq8

G G A T G C T A A C T T T A G A G T C T   Majority
                     470                 480

86  G G A T G C T A A C T T T A G A G T C C   carna5 cp cpexp33.seq
458  G G A T G C T A A C T T T A G A G T C T   New ccp.seq15
 86  G G A T G C T A A C T T T A G A G T C T   New cmvv34.seq5
368  G G A T G C A G G G T T G C G T G C T T   New cmvw1.seq1
 86  G G A T G C T A A C T T T A G A G T C T   New v27cp.seq5
 86  G G A T G C C A A C T T T A G A G T C T   New v33cp.seq8
```

FIG. 10C

```
      T G T C G C A G C A G C T T T C G C G A    Majority
                      490                500
106   T G T C G C A G C A G C T T T C G C G A    carna5 cp cpexp33.seq
478   T G T C G C A G C A G C T T T C G C G A    New ccp.seq15
106   T G T C G C A G C A G C T T T C G C G A    New cmvv34.seq5
388   T G A C T C A G C A G A T G C T G A A A    New cmvwl.seq1
106   T G T C G C A G C A G C T T T C G C G A    New v27cp.seq5
106   T G T C G C A G C A G C T T T C G C G A    New v33cp.seq8

C T T A A T A A G A C G T T A G C A G C    Majority
                      510                520
126   C T T A A T A A G A C G T T A G C A G C    carna5 cp cpexp33.seq
498   C T T A A T A A G A C G T T A G C A G C    New ccp.seq15
126   C T T A A C A A G A C G T T A G C A G C    New cmvv34.seq5
408   C T C A A T A G A A C C T C G C C A T      New cmvwl.seq1
126   C T T A A C A A G A C G T T A G C A G C    New v27cp.seq5
126   C T T A A T A A G A C G T T G T C A G C    New v33cp.seq8

T G G T C G T C C A A C T A T T A A C C    Majority
                      530                540
146   T G G T C G T C C A A C T A T T A A C C    carna5 cp cpexp33.seq
518   T G G T C G T C C A A C T A T T A A C C    New ccp.seq15
146   T G G T C G T C C A A C T A T T A A C C    New cmvv34.seq5
428   T G G T C G T C C C A C T C T T A A C C    New cmvwl.seq1
146   T G G T C G T C C A A C T A T T A A C C    New v27cp.seq5
146   T G G T C G T C C A A C T A T T A A C C    New v33cp.seq8

A C C A A C C T T T G T A G G G A G T      Majority
                      550                560
166   A C C A A C C T T T G T A G G G A G T      carna5 cp cpexp33.seq
538   A C C A A C C T T T G T A G G G A G T      New ccp.seq15
166   A C C A A C C T T T G T A G G G A G T      New cmvv34.seq5
448   A C C A A C C T T C G T G G G T A G T      New cmvwl.seq1
166   A C C A A C C T T T G T A G G G A G T      New v27cp.seq5
166   A C C A A C C T T T G T A G G G A G T      New v33cp.seq8
```

FIG. 10D

```
            G A A C G C T G T A G A C C T G G G T A    Majority
                           570                 580
186         G A A C G C T G T A G A C C T G G G T A    carna5 cp cpexp33.seq
558         G A A C G C T G T A G A C C T G G G T A    New ccp.seq15
186         G A A C G C T G T A G A C C T G G G T A    New cmvv34.seq5
468         G A A[A]G C T G T A[A]A C C[C]G G[T]T A    New cmvw1.seq1
186         G A A C G C T G T A[A]A C C T G G G T A    New v27cp.seq5
186         G A[G]C[G]T T G T A[A]A[T]C T G G G T A    New v33cp.seq8

C A C G T T C A C A T C T A T T A C C C    Majority
                           590                 600
206         C A C G T T C A C A T C T A T T A C C C    carna5 cp cpexp33.seq
578         C A C G T T C A C A T C T A T T A C C C    New ccp.seq15
206         C A C G T T C A C A T C T A T T A C C C    New cmvv34.seq5
488         C A C[T]T T C A C A T C T A T T A C C C    New cmvw1.seq1
206         C A C G T T C A C A T C T A T T A C C C    New v27cp.seq5
206         C A C G T T C A C A T C T A T T A C C C    New v33cp.seq8

T A A A G C C A C C A A A A A T A G A C    Majority
                           610                 620
226         T A A A G C C A C C A A A A A T A G A C    carna5 cp cpexp33.seq
598         T A A A G C C A C C A A A A A T A G A C    New ccp.seq15
226         T A A A G C C A C C A A A A A T A G A C    New cmvv34.seq5
508         T[G]A A[A]C C[G]C C[T G]A A A T[T]G A[G]   New cmvw1.seq1
226         T A A A G C C A C C A A A A A T A G A C    New v27cp.seq5
226         T A A A G C C[G]C C[G]A A A A T A G A C    New v33cp.seq8

C G T G G G T C T T A T T A C G G T A A    Majority
                           630                 640
246         C G T G G G T C T T A T T A C G G T A A    carna5 cp cpexp33.seq
618         C G T G[A]G T C T T A T T A C G G T A A    New ccp.seq15
246         C G[C]G G G T C T T A[C]T A C G G T A A    New cmvv34.seq5
528         A A A G G[T]T C[A]T A T T[T T]G G T A[G]   New cmvw1.seq1
246         C G T G G G T C T T A T T A C G G T A A    New v27cp.seq5
246         C G T G G G T C T T A T T A[T]G G T A A    New v33cp.seq8
```

FIG. 10E

```
        A A G G T T G T T A T T A C C T G A T T    Majority
                         650              660
266    |A A G G T T G T T A|C|T A C C T G A T T|   carna5 cp cpexp33.seq
638    |A A G G T T G T T A|C|T A C C T G A T T|   New ccp.seq15
266    |A A G G T T G T T A|C|T A C C T G A T T|   New cmvv34.seq5
548    |A A G G T T G T|C T|T T|G|C C|A|G A T T|   New cmvw1.seq1
266    |A A G G T T G T T A T T A C C T G A T T|   New v27cp.seq5
266    |A A G G T T G T T A T T A C C T G A T T|   New v33cp.seq8

C A G T C A C G G A A T A T G A T A A G    Majority
                         670              680
286    |C A G T C A C|A|G A A T A T G A T A A G|   carna5 cp cpexp33.seq
568    |C A G T C A C G G A A T A T G A T A A G|   New ccp.seq15
286    |C A G T C A C G G A A T A T G A T A A G|   New cmvv34.seq5
568    |C A G T C A C G G A|C|T A T G A T A A G|   New cmvw1.seq1
286    |C A G T C A C G G A A T A T G A T A A G|   New v27cp.seq5
286    |C A G T C A C|A|G A A T A T G A T A A G|   New v33cp.seq8

A A G C T T G T T T C G C G C A T T C A    Majority
                         690              700
306    |A A G C T T G T T T C G C G C A T T C A|   carna5 cp cpexp33.seq
678    |A A G C T T G T T T C G C G C A T T C A|   New ccp.seq15
306    |A A G C T T G T T T C G C G C A T T C A|   New cmvv34.seq5
588    |A A G C T T G T T T C G C G C A T T C A|   New cmvw1.seq1
306    |A A G C T T G T T T C G C G C A T T C A|   New v27cp.seq5
306    |A A|A|C T T G T T T C G C G C A T T C A|   New v33cp.seq8

A A T T C G A G T T A A T C C T T T G C    Majority
                         710              720
326    |A A T T C G A G T T A A T C C T T T G C|   carna5 cp cpexp33.seq
698    |A A T T C G A G T T A A T C C T T T G C|   New ccp.seq15
326    |A A T T C G A G T T A A T C C T T T G C|   New cmvv34.seq5
608    |A A T|C A|G|G|T T A A T C C T T T G C|     New cmvw1.seq1
326    |A A T T C G A G T T A A T C C T T T G C|   New v27cp.seq5
326    |A A T T C G A G T T A A T C C|C|T T G C|   New v33cp.seq8
```

FIG. 10F

```
      C G A A A T T T G A T T C T A C C G T G    Majority
                      730                 740

346   C G A A A T T T G A T T C T A C C G T G    carna5 cp cpexp33.seq
718   C G A A A T T T G A T T C T A C C G T G    New ccp.seq15
346   C G A A A T T T G A T T C T A C C G T G    New cmvv34.seq5
628   C G A A A T T T G A T T C T A C C G T G    New cmvw1.seq1
346   C G A A A T T T G A T T C T A C C G T G    New v27cp.seq5
346   C G A A A T T T G A T T C T A C C G T G    New v33cp.seq8

T G G G T G A C A G T C C G T A A A G T    Majority
                      750                 760

266   T G G G T G A C A G T C C G T A A A G T    carna5 cp cpexp33.seq
738   T G G G T G A C A G T C C G T A A A G T    New ccp.seq15
366   T G G G T G A C A G T T C G T A A A G T    New cmvv34.seq5
648   T G G G T A C A G T T C G G A A A G T      New cmvw1.seq1
366   T G G G T A A C A G T C C G T A A A G T    New v27cp.seq5
366   T G G G T G A C A G T C C G T A A A G T    New v33cp.seq8

T C C T G C C T C C T C G G A C T T A T    Majority
                      770                 780

386   T C C T G C C T C C T C G G A C T T A T    carna5 cp cpexp33.seq
758   T C C T G C C T C C T C G G A C T T A T    New ccp.seq15
386   T C C T G C C T C C T C G G A C T T A T    New cmvv34.seq5
668   A C C T T C A T C A T C C G A T C T T T    New cmvw1.seq1
386   T C C T G C C T C C T C G G A C T T A T    New v27cp.seq5
386   T C C T G C C T C C T C G G A C T T A T    New v33cp.seq8

C C G T T G C C G C C A T C T C T G C T    Majority
                      790                 800

406   C C G T T G C C G C C A T C T C T G C T    carna5 cp cpexp33.seq
778   C C G T T G C C G C C A T C T C T G C T    New ccp.seq15
406   C C G T T G C C G C C A T C T C T G C T    New cmvv34.seq5
688   C C G T C G C C G C C A T C T C T G C T    New cmvw1.seq1
406   C C G T T G C C G C C A T C T C T G C T    New v27cp.seq5
406   C C G T T G C C G C C A T C T C T G C T    New v33cp.seq8
```

FIG. 10G

```
        A T G T T C G C G G A C G G A G C C T C   Majority
                        810                 820

426    |A T G T T C G C G G A C G G A G C C T C|  carna5 cp cpexp33.seq
798    |A T G T T C G C G G A C G G A G C C T C|  New ccp.seq15
426    |A T G T T C G C G G A C G G A G C C T C|  New cmvv34.seq5
708    |A T G T T[T]G[C]G A[T]G G[T A A T]T C|    New cmvwl.seq1
426    |A T G T T C G C G G A C G G A G C C T C|  New v27cp.seq5
426    |A T G T T[T]G C G G A C G G A G C C T C|  New v33cp.seq8

A C C G G T A C T G G T T T A T C A G T   Majority
                        830                 840

446    |A C C G G T A C T G G T T T A T C A G T|  carna5 cp cpexp33.seq
818    |A C C G G T A C T G G T T T A T C A G T|  New ccp.seq15
446    |A C C G G T A C T G G T T T A T C A G T|  New cmvv34.seq5
728    |A C C G G T[T T]T G G T T T A T C A G T|  New cmvwl.seq1
446    |A C C G G T A C T G G T T T A T C A G T|  New v27cp.seq5
446    |A C C G G T A C T G G T T T A T C A G T|  New v33cp.seq8

A T G C T G C A T C T G G A G T C C A A   Majority
                        850                 860

466    |A T G[C]C G C A T C T G G A G T C C A A|  carna5 cp cpexp33.seq
838    |A T G[C]C G C A T C T G G A G T C C A A|  New ccp.seq15
466    |A T G C T G C A T C T G G A G T[T]C A A|  New cmvv34.seq5
748    |A T G C T G C[G]T C[C]G G A G T[T]C A[G]| New cmvwl.seq1
466    |A T G C T G C A T C T G G A G T C C A A|  New v27cp.seq5
466    |A[C]G C T G C A T C T G G A G T C C A A|  New v33cp.seq8

G C T A A C A A C A A A T T G T T G T A   Majority
                        870                 880

486    |G C[C]A A C A A C A A A[C]T G T T G T A|  carna5 cp cpexp33.seq
858    |G C[C]A A C A A C A A A[C]T G T T G T[T]| New ccp.seq15
486    |G C T A A C A A C A A A T T G T T G T A|  New cmvv34.seq5
768    |G C[C]A A C A A T A A G T T[A C]T[T]T A|  New cmvwl.seq1
486    |G C T A A C A A C A A A T T G T T G T A|  New v27cp.seq5
486    |G C T A A C A A C A A A T T G T T G T A|  New v33cp.seq8
```

FIG. 10H

```
    T G A T C T T T C G G C G A T G C G C G    Majority
                   890             900
506 |T G A T C T T T C G G C G A T G C G C G|  carna5 cp cpexp33.seq
878 |T G A T C T T T C G G C G A T G C G C G|  New ccp.seq15
506 |T G A T C T T T C G G C G A T G C G C G|  New cmvv34.seq5
788 |T G A[C]C T[G]T C[C]G[A]G A T G C G[T]G|  New cmvw1.seq1
506 |T G A T C T T T C G G C G A T G C G C G|  New v27cp.seq5
506 |T G A T C T T T C G G C G A T G C G C G|  New v33cp.seq8

C T G A T A T A G G T G A C A T G A G A    Majority
                   910             920
526 |C T G A T A T A G G T G A C A T G A G A|  carna5 cp cpexp33.seq
898 |C T G A T A T A G G T G A C A T G A G A|  New ccp.seq15
526 |C T G A T A T A G G T G A C A T G A G A|  New cmvv34.seq5
808 |C T G A T A T[C]G G[C]G A C A T G[C]G[T]|  New cmvw1.seq1
526 |C T G A T A T A G G T G A C A T G A G A|  New v27cp.seq5
526 |C T G A T A T A G G[C]G A C A T G A G A|  New v33cp.seq8

A A G T A C G C C G T C C T C G T G T A    Majority
                   930             940
546 |A A G T A C G C C G T C C T C G T G T A|  carna5 cp cpexp33.seq
918 |A A G T A C G C C G T C C T C G T G T A|  New ccp.seq15
546 |A A G T A C G C C G T C C T C G T G T A|  New cmvv34.seq5
828 |A A G T A C G C C G T C C T[G]G T[T]T A|  New cmvw1.seq1
546 |A A G T A C G C C G T C C T C G T G T A|  New v27cp.seq5
546 |A A G T A C G C C G T C C T C G T G T A|  New v33cp.seq8

T T C A A A A G A C G A T G C G C T C G    Majority
                   950             960
566 |T T C A A A A G A C G A T G C G C T C G|  carna5 cp cpexp33.seq
938 |T T C A A A A G A C G A T G C G C T C G|  New ccp.seq15
566 |T T C A A A A G A C G A T G C[A]C T C G|  New cmvv34.seq5
848 |[C]T C[G]A A A G A C G A T[A A A]C T[A]G|  New cmvw1.seq1
566 |T T C A A A A G A C G A T G C G C T C G|  New v27cp.seq5
566 |T T C A A A A G A C G A T G C[A]C T C G|  New v33cp.seq8
```

FIG. 10I

```
            A G A C G G A C G A G C T A G T A C T T   Majority
                          970               980

586     | A G A C G G A C G A G C T A G T A C T T |  carna5 cp cpexp33.seq
958     | A G A C G G A C G A G C T A G T A C T T |  New ccp.seq15
586     | A G A C G G A C G A G C T A G T A C T T |  New cmvv34.seq5
868     | A G A[A]G G A C G A G[A]T[T]G[C]A C T T |  New cmvw1.seq1
586     | A G A C G G A C G A G C T A G T A C T T |  New v27cp.seq5
586     | A G A C G G A C G A G C T A G T A C T T |  New v33cp.seq8

C A T G T T G A C A T C G A G C A C C A   Majority
                          990               1000

606     | C A T G T T G A C A T C G A G C A C C A |  carna5 cp cpexp33.seq
978     | C A T G T T G A C A T C G A G C A C C A |  New ccp.seq15
906     | C A T G T T G A C A T C G A G C A C C A |  New cmvv34.seq5
888     | C A T G T[C]G A C[G]T C G A G C A[T]C A |  New cmvw1.seq1
606     | C A T G T T G A C A T C G A G C A C C A |  New v27cp.seq5
606     | C A T G T T G A C[G]T C G A G C A C C A |  New v33cp.seq8

A C G C A T T C C C A C G T C T G G G G   Majority
                          1010              1020

626     | A C G C A T T C C C A C G T C T G G[A]G |  carna5 cp cpexp33.seq
998     | A C G C A T T C C C A C[A]T C T G G A G |  New ccp.seq15
626     | A C G C A T T C C C A C G T C T G G G G |  New cmvv34.seq5
908     | A C G[A]A T T C C[T]A[T]C[T]C[A C]G G[A]|  New cmvw1.seq1
626     | A C G[T]A T T C C C A C G T C T G G G A |  New v27cp.seq5
626     | A C G C A T T C C C A C G T C T G G G G |  New v33cp.seq8

T G C T C C C A G T C T G A T T C X T G   Majority
                          1030              1040

646     | T G C T C C C A G T C T G A T T C|.[T]G |  carna5 cp cpexp33.seq
1018    | T G C T C C C A G T C T G A T T C|.[C]G |  New ccp.seq15
646     | T G C T C C C A G T[T]T G A T T C|.[C]G |  New cmvv34.seq5
928     | T G C[T]C C C[G A C T]A G T[C]C|G[T]G |  New cmvw1.seq1
646     | T G C T C C C A G T C T G A T T C|.[C]G |  New v27cp.seq5
646     | T G C T C C C A G T[A]T[A]A T T C|.[T]G |  New v33cp.seq8
```

FIG. 10J

```
            T G X T T C C C X X X X X X X X A G A A    Majority
                            |                    |
                           1050                 1060
 665   |T G . T T C C C . . . . . . . . A G A A|   carna5 cp cpexp33.seq
1037   |T G . T T C C C . . . . . . . . A G A A|   New ccp.seq15
 665   |T G . T T C C . . . . . . . . . A G A A|   New cmvv34.seq5
 948   |T G T T T A C C G G C G T C C G A G A A|   New cmvw1.seq1
 665   |T G . T T C C C . . . . . . . . A G A A|   New v27cp.seq5
 665   |T G C T T T C C . . . . . . . . A G A A|   New v33cp.seq8

C C C T C C X C T C C G A T T T C T G T    Majority
                            |                    |
                           1070                 1080
 676   |C C C T C C . C T C C G A T C T C T G T|   carna5 cp cpexp33.seq
1048   |C C C T C C . C T C C G A T C T C T G T|   New ccp.seq15
 675   |C C C T C C . C T C C G A T T T C T G T|   New cmvv34.seq5
 968   |C G T A A A C T A C A C T C T C A A T|     New cmvw1.seq1
 676   |C C C T C C . C T C C G A T T T C T G T|   New v27cp.seq5
 677   |C C C T C C . C T C C G A T T T C T G T|   New v33cp.seq8

G G C G G G A G C T G A G T T G G C A G    Majority
                            |                    |
                           1090                 1100
 695   |G G C G G G A G C T G A G T T G G C A G|   carna5 cp cpexp33.seq
1067   |G G C G G G A G C T G A G T T G G C A G|   New ccp.seq15
 694   |G G C G G G A G C T G A G T T G G C A G|   New cmvv34.seq5
 988   |C G C G A G T G C T G A C T T G G T A G|   New cmvw1.seq1
 695   |G G C G G G A G C T G A G T T G G C A G|   New v27cp.seq5
 696   |G G C G G G A G C T G A G T T G G C A G|   New v33cp.seq8

T T C T G C T A T A A A C T G T C T G A    Majority
                            |                    |
                           1110                 1120
 715   |T T C T G C T G T A A A C T G T C T G A|   carna5 cp cpexp33.seq
1087   |T T C T A C T A C A A A C T G T C T G G|   New ccp.seq15
 714   |T T C T G C T A T A A A C T G T C T G A|   New cmvv34.seq5
1008   |T A T T G C T T C A A A C T G C C T G A|   New cmvw1.seq1
 715   |T T C T G C T A T A A A C T G T C T G A|   New v27cp.seq5
 716   |T T C T G C T G T A A A C T G T C T G A|   New v33cp.seq8
```

FIG. 10K

```
      A G T C A C T A A A C G T T T T A X X X    Majority
                    1130            1140

735  |A G T C A C T A A A C G T T T T A|. . .   carna5 cp cpexp33.seq
1107  |A G T C A C T A A A C G T T T T A|. . .   New ccp.seq15
 734  |A G T C A C T A A A C G T T T T A|. . .   New cmvv34.seq5
1028  |A G T C[C]C T A A A C G T[G]T T[G]T T G   New cmvw1.seq1
 735  |A G T C A C T A A A C G T T T[C]A|. . .   New v27cp.seq5
 736  |A G T C A C T A A A C G T T T T A|. . .   New v33cp.seq8

X X C G G T G A A C G G G T T G T C C A   Majority
                    1150            1160

752  . .|C G G T G A A C G G G T T G T C C A|  carna5 cp cpexp33.seq
1124  . .|C G G T G A A C G G G T T G T C C A|  New ccp.seq15
 751  . .|C G G T G A A C G G G T T G T C C A|  New cmvv34.seq5
1048  G G|C G G[G]G A A C G G G T[.]G T C C A|  New cmvw1.seq1
 752  . .|C G G T G A A C G G G T T G T C C A|  New v27cp.seq5
 736  . .|C G G T G A A C G G G T T G T C C A|  New v33cp.seq8

T X X X X X X X X X X X X X X X X X X X   Majority
                    1170            1180

770  |T|. . . . . . . . . G G . . . . . . . .   carna5 cp cpexp33.seq
1142  |T|C C A G C T T A C G G C T A A A A T G   New ccp.seq15
 769  |T|. . . . . . . . . . . . . . . . . . .   New cmvv34.seq5
1067  |T|C C A G C T T A C G G C T A A A A T G   New cmvw1.seq1
 770  |T|. . . . . . . . . . . . . . . . . . .   New v27cp.seq5
 771  |T|. . . . . . . . . . . . . . . . . . .   New v33cp.seq8

X X X X X X X X X X X X X X X X X X X X   Majority
                    1190            1200

772   . . . . . . . . . . . . . . . . . . . .   carna5 cp cpexp33.seq
1162   G T C A . G T C G T G G A G A A A T C C   New ccp.seq15
 770   . . . . . . . . . . . . . . . . . . . .   New cmvv34.seq5
1087   G T C G T G T C T T T C A . . . . . . C   New cmvw1.seq1
 771   . . . . . . . . . . . . . . . . . . . .   New v27cp.seq5
 772   . . . . . . . . . . . . . . . . . . . .   New v33cp.seq8
```

PLANTS RESISTANT TO WT STRAINS OF CUCUMBER MOSAIC VIRUS

This application is a divisional of U.S. Ser. No. 08/875,233, filed Sep. 29, 1997, now U.S. Pat. No. 6,127,601, which is a 371 of PCT/US95/07234 filed Jun. 7, 1995, which is a continuation of U.S. Ser. No. 08/367,789, filed Dec. 30, 1994, now abandoned.

BACKGROUND OF THE INVENTION

1. Field of the Invention

This invention relates to coat protein (CP) genes derived from WT strains of cucumber mosaic virus (CMV). More specifically, the invention relates to the genetic engineering of plants and to a method for conferring viral resistance to a plant using an expression cassette encoding CP genes of WT strains of CMV.

2. Description of the Prior Art

Many agriculturally important crops are susceptible to infection by plant viruses, particularly CMV, which can seriously damage a crop, reduce its economic value to the grower, and increase its cost to the consumer. Attempts to control or prevent infection of a crop by a plant virus such as CMV have been made, yet viral pathogens continue to be a significant problem in agriculture.

Scientists have recently developed means to produce virus resistant plants using genetic engineering techniques. Such an approach is advantageous in that the genetic material which provides the protection is incorporated into the genome of the plant itself and can be passed on to its progeny. A host plant is resistant if it possesses the ability to suppress or retard the multiplication of a virus, or the development of pathogenic symptoms. "Resistant" is the opposite of "susceptible," and may be divided into: (1) high, (2) moderate, or (3) low resistance, depending upon its effectiveness. Essentially, a resistant plant shows reduced or no symptom expression, and virus multiplication within it is reduced or negligible. Several different types of host resistance to viruses are recognized. The host may be resistant to: (1) establishment of infection, (2) virus multiplication, or (3) viral movement.

CMV is a single-stranded (+) ribonucleic acid (RNA) plant virus that has a functionally divided genome. The virus genome contains four RNA species designated RNAs 1–4. RNAs 3 and 4 encode the coat protein (CP) which is a protein that surrounds the viral RNA and protects the viral RNA from being degraded. Only RNAs 1–3 are required for infectivity because the CP, which is encoded by RNA 4, is also encoded by RNA 3.

Several strains of CMV have been classified using serology, host range, peptide mapping, nucleic acid hybridization, and sequencing analyses. These CMV strains can be divided into two groups, which are designated "WT" (also known as subgroup I) and "S" (also known as subgroup II). The S group consists of at least three members. The WT group is known to contain at least 17 members.

Expression of the CP genes from tobacco mosaic virus, alfalfa mosaic virus, CMV, and potato virus X, among others, in transgenic plants has resulted in plants which are resistant to infection by the respective virus. Heterologous protection can also occur. For example, the expression of CP genes from watermelon mosaic virus-2 (WMV-2) or zucchini yellow mosaic virus (ZYMV) in transgenic tobacco plants has been shown to confer protection against six other potyviruses: bean yellow mosaic virus, potato virus Y, pea mosaic virus, clover yellow vein virus, pepper mottle virus, and tobacco etch virus. However, expression of a preselected CP gene does not reliably confer heterologous protection to a plant. For example, transgenic squash plants containing the CMV-C CP gene, a WT virus, which have been shown to be resistant to the CMV-C strain are not protected to the same degree against several other, highly virulent WT strains of CMV.

Thus, a need exists for plants resistant to WT strains of CMV.

SUMMARY OF THE INVENTION

This invention provides: an isolated and purified deoxyribonucleic acid (DNA) molecule that encodes the CP for the V27 strain of CMV (CMV-V27), and a chimeric expression cassette comprising this DNA molecule; an isolated and purified DNA molecule that encodes the CP for the V33 strain of CMV (CMV-V33), and a chimeric expression cassette comprising this DNA molecule; and an isolated and purified DNA molecule that encodes the CP for the V34 strain of CMV (CMV-V34), and a chimeric expression cassette comprising this DNA molecule; and an isolated and purified DNA molecule that encodes the CP for the A35 strain of CMV (CMV-A35), and a chimeric expression cassette comprising the DNA molecule. Another embodiment of the invention is exemplified by the insertion of multiple virus gene expression cassettes into one purified DNA molecule, e.g., a plasmid. Each of these cassettes also includes a promoter which functions in plant cells to cause the production of an RNA molecule, and at least one polyadenylation signal comprising 3' nontranslated DNA which functions in plant cells to cause the termination of transcription and the addition of polyadenylated ribonucleotides to the 3' end of the transcribed messenger RNA (mRNA) sequences, wherein the promoter is operably linked to the DNA molecule, and the DNA molecule is operably linked to the polyadenylation signal. Preferably, these cassettes include the promoter of the 35S gene of cauliflower mosaic virus (CaMV-355 gene) and the polyadenylation signal of the CaMV-35S gene (CaMV-35S).

Also provided are bacterial cells, and transformed plant cells, containing the chimeric expression cassettes comprising the CP genes derived from the CMV-V27, CMV-V33, CMV-V34, or CMV-A35 strains, and preferably the 35S promoter and the polyadenylation signal of the CaMV-35S gene. Plants are also provided, wherein the plants comprise a plurality of transformed cells containing the chimeric CP gene expression cassettes derived from the CMV-V27, CMV-V33, CMV-V34, or CMV-A35 stains, and preferably the promoter and the polyadenylation signal of the CaMV gene. Transformed plants of this invention include tobacco, beets, corn, cucumber, peppers, potatoes, melons, soybean, squash, and tomatoes. Especially preferred are members of the Cucurbitaceae (e.g., squash and cucumber,) and Solanaceae (e.g., peppers and tomatoes) family.

Another aspect of the present invention is a method of preparing a CMV-resistant plant, such as a dicot, comprising: transforming plant cells with a chimeric expression cassette comprising a promoter functional in plant cells operably linked to a DNA molecule that encodes a CP of a WT strain of CMV, e.g., V27, V33, V34, or A35; regenerating the plant cells to provide a differentiated plant; and identifying a transformed plant that expresses the CMV CP at a level sufficient to render the plant resistant to infection by the specific strains of CMV disclosed herein.

As used herein, with respect to a DNA molecule or "gene," the phrase "isolated and purified" is defined to mean that the molecule is either extracted from its context in the viral genome by chemical means and purified and/or modified to the extent that it can be introduced into the present vectors in the appropriate orientation, i.e., sense or antisense. As used herein, the term "chimeric" refers to the linkage of two or more DNA molecules which are derived from different sources, strains or species (e.g., from bacteria and plants), or the linkage of two or more DNA molecules, which are derived from the same species and which are linked in a way that does not occur in the native genome. As used herein, "expression" is defined to mean transcription or transcription followed by translation of a particular DNA molecule.

BRIEF DESCRIPTION OF THE DRAWINGS

FIG. 1A. The nucleotide sequence of the CP gene of CMV-V27 from nucleotide position 1 to 360. The deduced amino acid sequence of the encoded open reading frame is shown below the nucleotide sequence.

FIG. 1B. The nucleotide sequence of the CP gene of CMV-V27 from nucleotide position 361 to 772. The deduced amino acid sequence of the encoded open reading frame is shown below the nucleotide sequence.

FIG. 2A. The nucleotide sequence of the CP gene of CMV-V33 from nucleotide position 1 to 420. The deduced amino acid sequence of the encoded open reading frame is shown below the nucleotide sequence.

FIG. 2B. The nucleotide sequence of the CP gene of CMV-V33 from nucleotide position 421 to 773. The deduced amino acid sequence of the encoded open reading frame is shown below the nucleotide sequence.

FIG. 3. The nucleotide sequence of the CP gene of CMV-V34 from nucleotide position 1 to 771. The deduced amino acid sequence of the encoded open reading frame is shown below the nucleotide sequence.

FIG. 4A. The alignment of the nucleotide sequences of the CP genes from five CMV strains from nucleotide position 1 to 600. Ccp and Cmvw1 are described in Quemada et al. (J. Gen. Virol., 70:1065 (1989)). Alignments were obtained with the use of the UWGCG Pileup program. The dots represent either the lack of sequence information at the 5' end of the CP gene or gaps in homology in sequences relative to others in the alignment. The position of primer RMM351 is shown.

FIG. 4B. The alignment of the nucleotide sequences of the CP genes from five CMV strains described in FIG. 4A from nucleotide position 601 to 840.

FIG. 4C. The alignment of the nucleotide sequences of the CP genes from five CMV strains described in FIG. 4A from nucleotide position 841 to 1080.

FIG. 4D. The alignment of the nucleotide sequences of the CP genes from five CMV strains from nucleotide position 1081 to 1170 alignment. The position of primer RMM352 is shown.

FIG. 5A. The alignment of the sequences of amino acid 1–150 deduced from the nucleotide sequences of CMV strains V27, V33, V34, CMV-C (shown in FIG. 4) and CMV strain Cmvq3 (Quemada et al., J. Gen. Virol., 70:1065 (1989)). Alignments were performed by the UWGCG Pileup program. Differences among the WT virus strains are underlined and highlighted with asterisks. The dots represent gaps in homology in sequences relative to others in the alignment.

FIG. 5B. The alignment of the sequences of amino acid 151–219 deduced from the nucleotide sequences of CMV strains as described in FIG. 5A.

(FIG. 6A, continued.) Insertion of a CMV-V27 CP expression cassette BamHI fragment into the BglII site of pEPG204 and pEPG205 to produce pEPG239 and pEPG240, respectively.

(FIG. 7A, continued.) Insertion of a CMV-V33 CP expression cassette BamHI fragment into the BglII site of pEPG204 and pEPG205 to produce pEPG196 and pEPG197, respectively.

FIG. 8. The nucleotide sequence of the CP gene of CMV-A35. The deduced amino acid sequence of the encoded open reading frame is shown below the nucleotide sequence.

FIG. 9A. The alignment of the amino acid sequences deduced from the nucleotide sequences of the six CMV strains shown in FIG. 10A for amino acid 1–120. Differences among the "C" type viruses are enclosed in boxes. The dashes represent gaps in homology in sequences relative to others in the alignment.

FIG. 9B. The alignment of the amino acid sequences deduced from the nucleotide sequences of the six CMV strains shown in FIG. 10 for amino acid 121 to 220.

FIG. 10A. The alignment of the nucleotide sequences of the CP genes from 6 CMV strains from nucleotide position 321–400 of a consensus sequence. The dots represent either the lack of sequence information at the 5' end of the CP gene or gaps in homology in sequences relative to others in the alignment.

FIG. 10B. The alignment of the nucleotide sequences of the CP genes of CMV strains described in FIG. 10A from nucleotide position 401 to 480.

FIG. 10C. The alignment of the nucleotide sequences of the CP genes of CMV strains described in FIG. 10A from nucleotide position 481 to 560.

FIG. 10D. The alignment of the nucleotide sequences of the CP genes of CMV strains described in FIG. 10A from nucleotide position 561 to 640.

FIG. 10E. The alignment of the nucleotide sequences of the CP genes of CMV strains described in FIG. 10A from nucleotide position 641 to 720.

FIG. 10F. The alignment of the nucleotide sequences of the CP genes of CMV strains described in FIG. 10A from nucleotide position 721 to 800.

FIG. 10G. The alignment of the nucleotide sequences of the CP genes of CMV strains described in FIG. 10A from nucleotide position 801 to 880.

FIG. 10H. The alignment of the nucleotide sequences of the CP genes of CMV strains described in FIG. 10A from nucleotide position 881 to 960.

FIG. 10I. The alignment of the nucleotide sequences of the CP genes of CMV strains described in FIG. 10A from nucleotide position 961 to 1040.

FIG. 10J. The alignment of the nucleotide sequences of the CP genes of CMV strains described in FIG. 10A from nucleotide position 1041 to 1120.

FIG. 10K. The alignment of the nucleotide sequences of the CP genes of CMV strains described in FIG. 10A from nucleotide position 1121 to 1200. The dots represent gaps in homology in sequences relative to others in the alignment.

DETAILED DESCRIPTION OF THE INVENTION

Figure 6A:
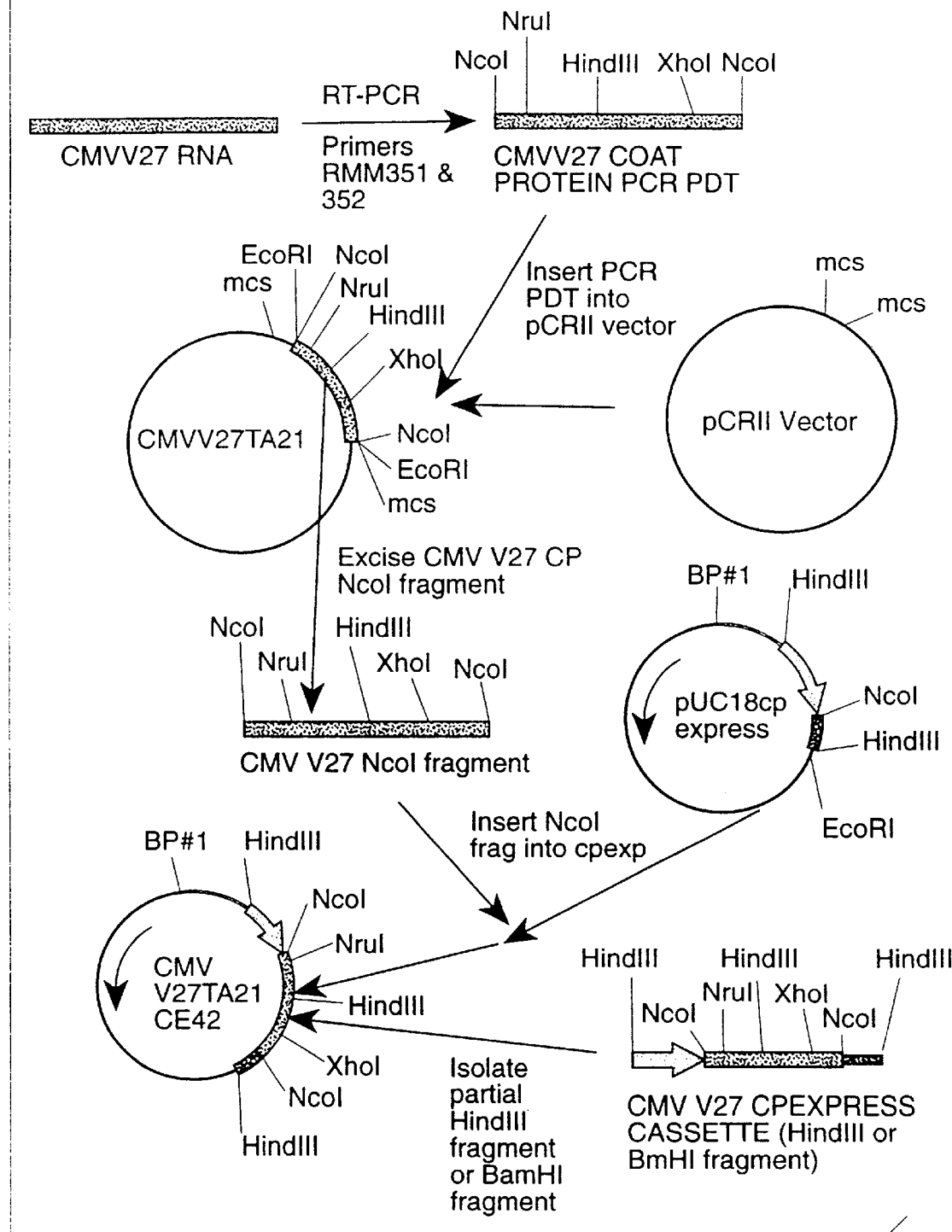
FIG. 6A. Assembly of CMV-V27 CP expression cassette. Polymerase chain reaction (PCR) products of CMV-V27 were installed into pCRII and subsequently inserted into pUC18cpexpress by routine methods. The bolded lines and arrows which are a part of the circle represent CaMV-35S sequences.

The genome of CMV contains four RNA species designated RNA 1, 2, 3 and 4; 3389 nucleotides (nt), 3035 nt, 2193 nt, and 1027 nt, respectively (Peden et al., Virol., 53:487 (1973); Gould et al., Eur. J. Biochem., 126:217 (1982); Rezaian et al., Eur. J. Biochem., 143:227 (1984); Rezaian et al., Eur. J. Biochem. 150:331 (1985)). Only RNA 1, 2 and 3 are required for infectivity (Peden et al., Virol., 53:487 (1973)) because the CP, which is encoded by RNA 4, is also encoded by RNA 3. Translation of CMV RNA yield a 95 kiloDalton (kD) polypeptide from RNA 1, a 94 kD polypeptide from RNA 2 (Gordon et al., Virol., 123:284 (1983)), and two polypeptides from RNA 3: its 5' end encodes a 35 kD polypeptide, and its 3' end encodes a 24.5 kD polypeptide (Gould et al., Eur. J. Biochem., 126:217 (1982)). The 24.5 kD polypeptide is identical to that encoded by RNA 4 and is the CP.

Several strains of CMV have been classified using serology, host range, peptide mapping, nucleic acid hybridization, and sequencing. These CMV strains include two groups, WT and S. CMV WT strains include CMV-C, CMV-V27, CMV-V33, CMV-V34, CMV-M, CMV-O, CMV-Y, and CMV-A35 while S strains include CMV-Q, CMV-WL, and CMV-LS (Zaitlin et al., Virol., 201:200 (1994)). Protection against a strain in one group does not necessarily provide protection against all strains in that group. For example, transgenic squash plants protected with CP genes from the CMV-C are not protected against the CMV strains V27, V33, V34, or A35. In addition, Zaitlin et al. (Virol., 201:200 (1994)) report that tobacco plants transgenic for a CMV-FNY replicase gene show protection against challenge from WT strains but show no protection against challenge from S strain challenges. Thus, the present invention is directed to providing plants with resistance to WT strains of CMV, e.g., V27, V33, V34, or A35.

To practice the present invention, a viral gene must be isolated from the viral genome and inserted into a vector. Thus, the present invention provides isolated and purified DNA molecules that encode the CP of the V27, V33, or V34 strains of CMV. As used herein, a DNA molecule that encodes a CP gene includes nucleotides of the coding strand, also referred to as the "sense" strand, as well as nucleotides of the noncoding strand, complementary strand, also referred to as the "antisense" strand, either alone or in their base-paired configuration. Thus, a DNA molecule that encodes the CP of the V27 strain of CMV, for example, includes the DNA molecule having the nucleotide sequence of FIG. 1, a DNA molecule complementary to the nucleotide sequence of FIG. 1, as well as a DNA molecule which also encodes a CMV CP and its complement which hybridizes with a CMV-V27-specific DNA probe in hybridization buffer with 6×SSC, 5× Denhardt's reagent, 0.5% SDS and 100 micrograms per milliliter ($\mu$g/ml) denatured, fragmented salmon sperm DNA and remains bound when washed at 68° C. in 0.1×SSC and 0.5% SDS (Sambrook et al., MOLECULAR CLONING: A LABORATORY MANUAL, 2nd ed. (1989)). Moreover, the DNA molecules of the present invention can include non-CMV CP nucleotides that do not interfere with expression of the CMV CP gene. Preferably, the isolated and purified DNA molecules of the present invention comprise a single coding region for the CP. Thus, preferably the DNA molecules of the present invention are those consisting essentially of DNA that encodes the CP.

These CMV genes are used to produce the CPs, which are believed to confer resistance to viruses. Another molecular strategy to provide virus resistance in transgenic plants is based on antisense RNA. As is well known, a cell manufactures protein by transcribing the DNA of the gene encoding that protein to produce RNA, which is then processed to mRNA (e.g., by the removal of introns) and finally translated by ribosomes into protein. This process may be inhibited in the cell by the presence of antisense RNA. The term antisense RNA means an RNA sequence which is complementary to a sequence of bases in the mRNA in question in the sense that each base (or the majority of bases) in the antisense sequence (read in the 31 to 5' sense) is capable of pairing with the corresponding base (G with C, A with U) in the mRNA sequence read in the 5' to 3' sense. It is believed that this inhibition takes place by formation of a complex between the two complementary strands of RNA, thus preventing the formation of protein. How this works is uncertain: the complex may interfere with further transcription, processing, transport or translation, or degrade the mRNA, or have more than one of these effects. This antisense RNA may be produced in the cell by transformation of the cell with an appropriate DNA construct arranged to transcribe the non-template strand (as opposed to the template strand) of the relevant gene (or of a DNA sequence showing substantial homology therewith).

The use of antisense RNA to downregulate the expression of specific plant genes is well known. Reduction of gene expression has led to a change in the phenotype of the plant: either at the level of gross visible phenotypic difference, e.g., lack of anthocyanin production in flower petals of petunia leading to colorless instead of colored petals (van der Krol et al., Nature, 333:866–869 (1988)); or at a more subtle biochemical level, e.g., change in the amount of polygalacturonase and reduction in depolymerization of pectin during tomato fruit ripening (Smith et al., Nature, 334:724–726 (1988)).

Another more recently described method of inhibiting gene expression in transgenic plants is the use of sense RNA transcribed from an exogenous template to downregulate the expression of specific plant genes (Jorgensen, Keystone Symposium "Improved Crop and Plant Products through Biotechnology", Abstract X1-022 (1994)). Thus, both antisense and sense RNA have been proven to be useful in achieving downregulation of gene expression in plants, which are encompassed by the present invention.

The CMV CP gene does not contain the signals necessary for its expression once transferred and integrated into a plant genome. Accordingly, a vector must be constructed to provide the regulatory sequences such that they will be functional upon inserting a desired gene. When the expression vector/insert construct is assembled, it is used to transform plant cells which are then used to regenerate plants. These transgenic plants carry the viral gene in the expression vector/insert construct. The gene is expressed in the plant and increased resistance to viral infection is conferred thereby.

Several different methods exist to isolate a viral gene. To do so, one having ordinary skill in the art can use information about the genomic organization of cucumoviruses to locate and isolate the CP gene. The CP gene is located near the 3' end of RNA 3. Using methods well known in the art, a quantity of virus is grown and harvested. The viral RNA is then separated by gel electrophoresis. A cDNA library is created using the viral RNA, by methods known to the art. The viral RNA is incubated with primers that hybridize to the viral RNA and reverse transcriptase, and a complementary DNA molecule is produced. A DNA complement of the complementary DNA molecule is produced and that sequence represents a DNA copy (cDNA) of the original viral RNA molecule. The DNA complement can be produced in a manner that results in a single double stranded cDNA or PCR can be used to amplify the DNA encoding the cDNA with the use of oligomer primers specific for viral sequences. These primers can include novel restriction sites used in subsequent cloning steps. Thus, a double stranded DNA molecule is generated which contains the sequence information of the viral RNA. These DNA molecules can be cloned in *E. coli* plasmid vectors after the additions of restriction enzyme linker molecules by DNA ligase. The various fragments are inserted into cloning vectors, such as well-characterized plasmids, which are then used to transform *E. coli* and create a cDNA library.

CMV CP genes from previously isolated strains can be used as hybridization probes to screen the cDNA library to determine if any of the transformed bacteria contain DNA fragments with sequences coding for a CMV CP. Alternatively, plasmids which harbor CMV CP sequences can be determined by restriction enzyme digestion of plasmids in bacterial transformants. The cDNA inserts in any bacterial colonies which contain this region can be sequenced. The CP gene is present in its entirety in colonies which have sequences that extend 5' to the sequence which encodes the ATG start codon and sequences that extend 3' of the stop codon.

Alternatively, cDNA fragments can be inserted in the sense orientation into expression vectors. Antibodies against the CP can be used to screen the cDNA expression library and the gene can be isolated from colonies which express the protein.

In the present invention, the DNA molecules encoding the CP genes of the CMV strains V27, V33, V34, and A35 have been determined and the genes have been inserted into expression cassettes. These expression cassettes can be individually placed into a vector that can be transmitted into plants, preferably a binary vector. Alternatively, two or more of the CMV CP genes can each be present in an expression cassette which can be placed into the same binary vector, or any of the CMV CP expression cassettes of the present invention can be placed into a binary vector with one or more viral gene expression cassettes. The expression vectors contain the necessary genetic regulatory sequences for expression of an inserted gene. The CP gene is inserted such that those regulatory sequences are functional and the genes can be expressed when incorporated into a plant genome. For example, vectors of the present invention can contain combinations of expression cassettes that include DNA from a heterologous CMV CP gene (i.e., one from another CMV isolate), papaya ringspot virus (PRV) CP gene, a ZYMV CP gene, and a WMV-2 CP gene.

Moreover, when combinations of viral gene expression cassettes are placed in the same binary plasmid, and that multigene cassette containing plasmid transformed into a plant, the viral genes all preferably exhibit substantially the same degrees of efficacy when present in transgenic plants. For example, if one examines numerous transgenic lines containing two different intact viral gene cassettes, the transgenic line will be immune to infection by both viruses. Similarly, if a line exhibits a delay in symptom development to one virus, it will also exhibit a delay in symptom development to the second virus. Finally, if a line is susceptible to one of the viruses it will be susceptible to the other. This phenomenon is unexpected. If there were not a correlation between the efficacy of each gene in these multiple gene constructs this approach as a tool in plant breeding would probably be prohibitively difficult to use. Even with single gene constructs, one must test numerous transgenic plant lines to find one that displays the appropriate level of efficacy. The probability of finding a line with useful levels of expression can range from 10–50% (depending on the species involved). For further information refer to Applicants' International Patent Application No. PCT/US95/06261 entitled "Transgenic Plants Expressing DNA Constructs Containing a Plurality of Genes to Impart Virus Resistance" filed on Jun. 7, 1995, incorporated by reference herein.

In order to express the viral gene, the necessary genetic regulatory sequences must be provided. In the present invention, the CP genes are inserted into vectors which contain cloning sites for insertion 3' of the initiation codon and 5' of the poly(A) signal. The promoter is 5' of the initiation codon such that when genes are inserted at the cloning site, a functional unit is formed in which the inserted genes are expressed under the control of the various genetic regulatory sequences.

The segment of DNA referred to as the promoter is responsible for the regulation of the transcription of DNA into mRNA. A number of promoters which function in plant cells are known in the art and can be employed in the practice of the present invention. These promoters can be obtained from a variety of sources such as plants or plant viruses, and can include, but are not limited to, promoters isolated from the caulimovirus group such as the CaMV-35S promoter (CaMV-35S), the enhanced CaMV-35S promoter (enh-CaMV-35S), the figwort mosaic virus full-length transcript promoter (FMV-35S), and the promoter isolated from the chlorophyll a/b binding protein. Other useful promoters include promoters which are capable of expressing the cucumovirus proteins in an inducible manner or in a tissue-specific manner in certain cell types in which the infection is known to occur. For example, the inducible promoters from phenylalanine ammonia lyase, chalcone synthase, hydroxyproline rich glycoprotein, extensin, pathogenesis-related proteins (e.g. PR-1a), and wound-inducible protease inhibitor from potato may be useful.

Preferred promoters for use in the present CP-containing cassettes include the constitutive promoters from CaMV, the tumor-inducing (Ti) genes nopaline synthase (NOS) (Bevan et al., Nucleic Acids Res., 11:369 (1983)) and octopine synthase (Depicker et al., J. Mol. Appl. Genet., 1:561

(1982)), and the bean storage protein gene phaseolin. The poly(A) addition signals from these genes are also suitable for use in the present cassettes. The particular promoter selected is preferably capable of causing sufficient expression of the DNA coding sequences to which it is operably linked, to result in the production of amounts of the proteins or RNA effective to provide viral resistance, but not so much as to be detrimental to the cell in which they are expressed. The promoters selected should be capable of functioning in tissues including, but not limited to, epidermal, vascular, and mesophyll tissues. The actual choice of the promoter is not critical, as long as it has sufficient transcriptional activity to accomplish the expression of the preselected proteins or their respective RNAs and subsequent conferral of viral resistance to the plants.

The nontranslated leader sequence can be derived from any suitable source and can be specifically modified to increase the translation of the mRNA. The 5' nontranslated region can be obtained from the promoter selected to express the gene, an unrelated promoter, the native leader sequence of the gene or coding region to be expressed, viral RNAs, suitable eucaryotic genes, or a synthetic gene sequence. The present invention is not limited to the constructs presented in the following examples.

The termination region or 3' nontranslated region which is employed is one which will cause the termination of transcription and the addition of polyadenylated ribonucleotides to the 3' end of the transcribed mRNA sequence. The termination region can be native with the promoter region, native with the gene, or can be derived from another source, and preferably include a terminator and a sequence coding for polyadenylation. Suitable 3' nontranslated regions of the chimeric plant gene include but are not limited to: (1) the 3' transcribed, nontranslated regions containing the polyadenylation signal of Agrobacterium Ti plasmid genes, such as the NOS gene; and (2) plant genes like the soybean 7S storage protein genes.

Preferably, the expression cassettes of the present invention are engineered to contain a constitutive promoter 5' to its translation initiation codon (ATG) and a poly(A) addition signal (AATAAA) 3' to its translation termination codon. Several promoters which function in plants are available, however, the preferred promoter is the 35S constitutive promoters from CaMV. The poly (A) signal can be obtained from the CaMV-35S gene or from any number of well characterized plant genes, i.e., NOS, octopine synthase, and the bean storage protein gene phaseolin. The constructions are similar to that used for the expression of the CMV-C CP in PCT patent application PCT/US88/04321, published on Jun. 29, 1989 as WO 89/05858, claiming the benefit of U.S. Ser. No. 135,591, filed Dec. 21, 1987, entitled "Cucumber Mosaic Virus Coat Protein Gene", and the CMV WL CP in PCT patent application PCT/US89/03288, published on Mar. 8, 1990 as WO 90/02185, claiming the benefit of U.S. Ser. No. 234,404, filed Aug. 19, 1988, entitled "Cucumber Mosaic Virus Coat Protein Gene."

Selectable marker genes can be incorporated into the present expression cassettes and used to select for those cells or plants which have become transformed. The marker gene employed may express resistance to an antibiotic, such as kanamycin, gentamycin, G418, hygromycin, streptomycin, spectinomycin, tetracycline, chloramphenicol, and the like. Other markers could be employed in addition to or in the alternative, such as, for example, a gene coding for herbicide tolerance such as tolerance to glyphosate, sulfonylurea, phosphinothricin, or bromoxynil. Additional means of selection could include resistance to methotrexate, heavy metals, complementation providing prototrophy to an auxotrophic host, and the like.

The particular marker employed will be one which will allow for the selection of transformed cells as opposed to those cells which are not transformed. Depending on the number of different host species one or more markers can be employed, where different conditions of selection would be useful to select the different host, and would be known to those of skill in the art. A screenable marker such as the β-glucuronidase gene can be used in place of, or with, a selectable marker. Cells transformed with this gene can be identified by the production of a blue product on treatment with 5-bromo-4-chloro-3-indoyl-β-D-glucuronide.

In developing the present expression construct, i.e., expression cassette, the various components of the expression construct such as the DNA molecules, linkers, or fragments thereof will normally be inserted into a convenient cloning vector, such as a plasmid or phage, which is capable of replication in a bacterial host, such as E. coli. Numerous cloning vectors exist that have been described in the literature. After each cloning, the cloning vector can be isolated and subjected to further manipulation, such as restriction, insertion of new fragments, ligation, deletion, resection, insertion, in vitro mutagenesis, addition of polylinker fragments, and the like, in order to provide a vector which will meet a particular need.

For Agrobacterium-mediated transformation, the expression cassette will be included in a vector, and flanked by fragments of the Agrobacterium Ti or root-inducing (Ri) plasmid, representing the right and, optionally the left, borders of the Ti or Ri plasmid transferred DNA (T-DNA). This facilitates integration of the present chimeric DNA sequences into the genome of the host plant cell. This vector will also contain sequences that facilitate replication of the plasmid in Agrobacterium cells, as well as in E. coli cells.

All DNA manipulations are typically carried out in E. coli cells, and the final plasmid bearing the cucumovirus expression cassette is moved into Agrobacterium cells by direct DNA transformation, conjugation, and the like. These Agrobacterium cells will contain a second plasmid, also derived from Ti or Ri plasmids. This second plasmid will carry all the vir genes required for transfer of the foreign DNA into plant cells. Suitable plant transformation cloning vectors include those derived from a Ti plasmid of *Agrobacterium tumefaciens*, as generally disclosed in Glassman et al. (U.S. Pat. No. 5,258,300), or *Agrobacterium rhizogenes*.

A variety of techniques are available for the introduction of the genetic material into or transformation of the plant cell host. However, the particular manner of introduction of the plant vector into the host is not critical to the practice of the present invention, and any method which provides for efficient transformation can be employed. In addition to transformation using plant transformation vectors derived from the Ti or Ri plasmids of Agrobacterium, alternative methods could be used to insert the DNA constructs of the present invention into plant cells. Such methods may include, for example, the use of liposomes, electroporation (Fromm et al., Proc. Natl. Acad. Sci. USA, 82:824 (1984)), chemicals that increase the free uptake of DNA (Paszkowski et al., EMBO J., 3:2717 (1984)), DNA delivery via microprojectile bombardment (Klein et al., Nature, 327:70 (1987)), microinjection (Crossway et al., Mol. Gen. Genet., 202:179 (1985)), and transformation using viruses or pollen.

The choice of plant tissue source or cultured plant cells for transformation will depend on the nature of the host plant and the transformation protocol. Useful tissue sources include callus, suspension culture cells, protoplasts, leaf segments, stem segments, tassels, pollen, embryos, hypocotyls, tuber segments, meristematic regions, and the like. The tissue source is regenerable, in that it will retain the ability to regenerate whole, fertile plants following transformation.

The transformation is carried out under conditions directed to the plant tissue of choice. The plant cells or tissue are exposed to the DNA carrying the present viral gene expression cassette(s) for an effective period of time. This can range from a less-than-one-second pulse of electricity for electroporation, to a two-to-three day co-cultivation in the presence of plasmid-bearing Agrobacterium cells. Buffers and media used will also vary with the plant tissue source and transformation protocol. Many transformation protocols employ a feeder layer of suspended culture cells (tobacco or Black Mexican Sweet Corn, for example) on the surface of solid media plates, separated by a sterile filter paper disk from the plant cells or tissues being transformed.

Following treatment with DNA, the plant cells or tissue may be cultivated for varying lengths of time prior to selection, or may be immediately exposed to a selective agent such as those described hereinabove. Protocols involving exposure to Agrobacterium will also include an agent inhibitory to the growth of the Agrobacterium cells. Commonly used compounds are antibiotics such as cefotaxime and carbenicillin. The media used in the selection may be formulated to maintain transformed callus or suspension culture cells in an undifferentiated state, or to allow production of shoots from callus, leaf or stem segments, tuber disks, and the like.

Cells or callus observed to be growing in the presence of normally inhibitory concentrations of the selective agents are presumed to be transformed and may be subcultured several additional times on the same medium to remove nonresistant sections. The cells or calli can then be assayed for the presence of the viral gene cassette, or can be subjected to known plant regeneration protocols. In protocols involving the direct production of shoots, those shoots appearing on the selective media are presumed to be transformed and can be excised and rooted, either on selective medium suitable for the production of roots, or by simply dipping the excised shoot in an Ri compound and directly planting it in vermiculite.

In order to produce transgenic plants exhibiting viral resistance, the viral genes must be taken up into the plant cell and stably integrated within the plant genome. Plant cells and tissues selected for their resistance to an inhibitory agent are presumed to have acquired the selectable marker gene encoding this resistance during the transformation treatment. Since the marker gene is commonly linked to the viral genes, it can be assumed that the viral genes have similarly been acquired. Southern blot hybridization analysis using a probe specific to the viral genes can then be used to confirm that the foreign genes have been taken up and integrated into the genome of the plant cell. This technique may also give some indication of the number of copies of the gene that have been incorporated. Successful transcription of the foreign gene into mRNA can likewise be assayed using Northern blot hybridization analysis of total cellular RNA and/or cellular RNA that has been enriched in a polyadenylated region. mRNA molecules encompassed within the scope of the invention are those which contain viral specific sequences derived from the viral genes present in the transformed vector which are of the same polarity as that of the viral genomic RNA such that they are capable of base pairing with viral specific RNA of the opposite polarity to that of viral genomic RNA under conditions described in Chapter 7 of Sambrook et al. (1989). Moreover, mRNA molecules encompassed within the scope of the invention are those which contain viral specific sequences derived from the viral genes present in the transformed vector which are of the opposite polarity as that of the viral genomic RNA such that they are capable of base pairing with viral genomic RNA under conditions described in Chapter 7 in Sambrook et al. (1989).

The presence of a viral gene can also be detected by immunological assays, such as the double-antibody sandwich assays described by Namba et al., Gene, 107:181 (1991) as modified by Clark et al., J. Gen. Virol., 34:475 (1979). See also, Namba et al., Phytopathology, 82:940 (1992). Cucumovirus resistance can also be assayed via infectivity studies as generally disclosed by Namba et al., ibid., wherein plants are scored as symptomatic when any inoculated leaf shows vein clearing, mosaic or necrotic symptoms.

Seed from plants regenerated from tissue culture is grown in the field and self-pollinated to generate true breeding plants. The progeny from these plants become true breeding lines which are evaluated for viral resistance in the field under a range of environmental conditions. The commercial value of viral-resistant plants is greatest if many different hybrid combinations with resistance are available for sale. The farmer typically grows more than one kind of hybrid based on such differences as maturity, color or other agronomic traits. Additionally, hybrids adapted to one part of a country are not adapted to another part because of differences in such traits as maturity, disease and insect tolerance. Because of this, it is necessary to breed viral resistance into a large number of parental lines so that many hybrid combinations can be produced.

The invention will be further described by reference to the following detailed examples. Enzymes were obtained from commercial sources and were used according to the vendor's recommendations or other variations known in the art. Other reagents, buffers, etc., were obtained from commercial sources, such as Sigma Chemical Co., St. Louis, Mo., unless otherwise specified.

Most of the recombinant DNA methods employed in practicing the present invention are standard procedures, well known to those skilled in the art, and described in detail in, for example, in European Patent Application Publication Number 223,452, published Nov. 29, 1986, which is incorporated herein by reference. General references containing such standard techniques include the following: R. Wu, ed., METHODS IN ENZYMOLOGY, Vol. 68 (1979); J. H. Miller, EXPERIMENTS IN MOLECULAR GENETICS (1972); J. Sambrook et al., MOLECULAR CLONING: A LABORATORY MANUAL, 2nd ed. (1989); and D. M. Glover, ed., DNA CLONING VOL. II (1982).

Figure 6B:
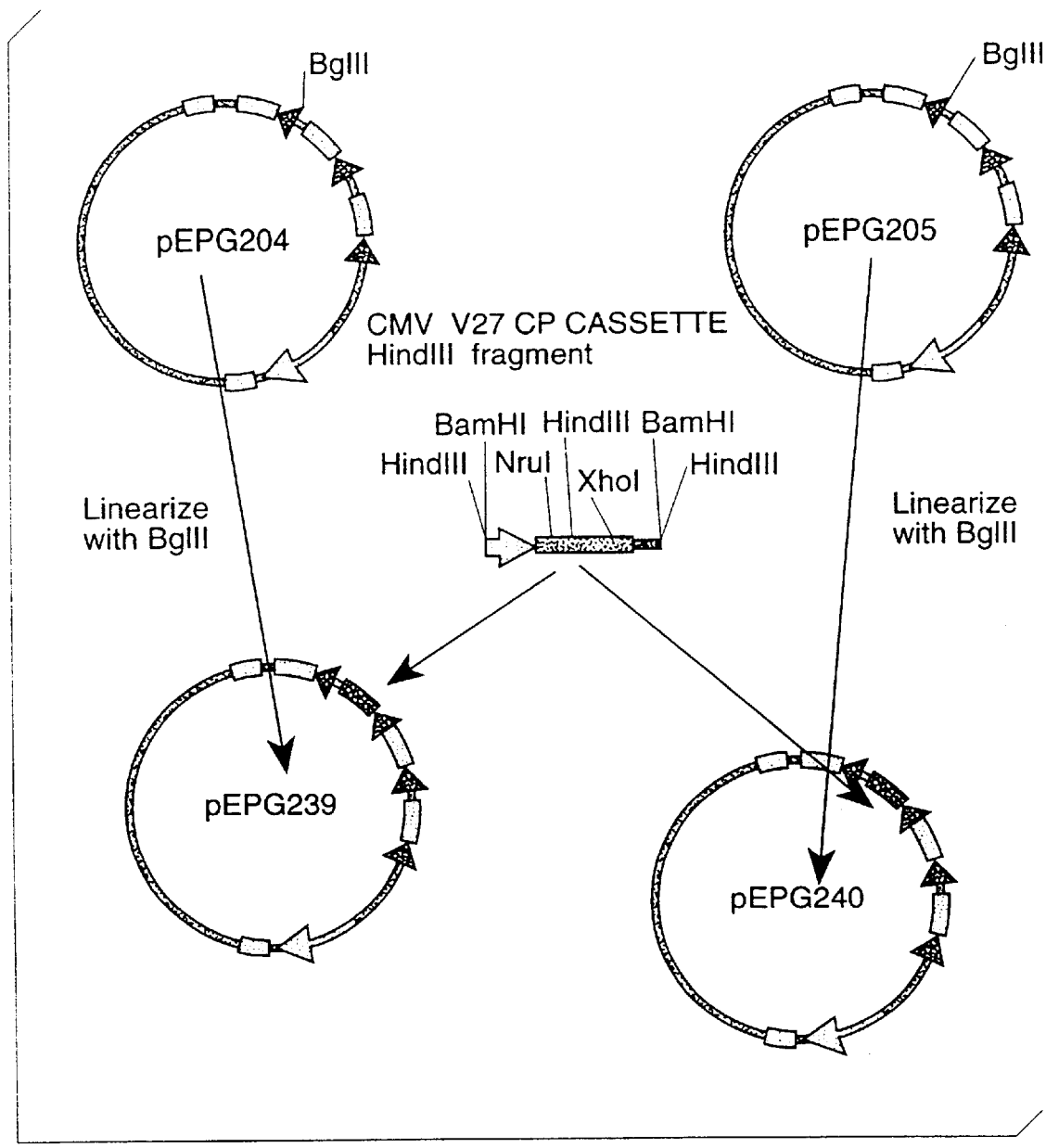
FIG. 6B.
Figure 6C:
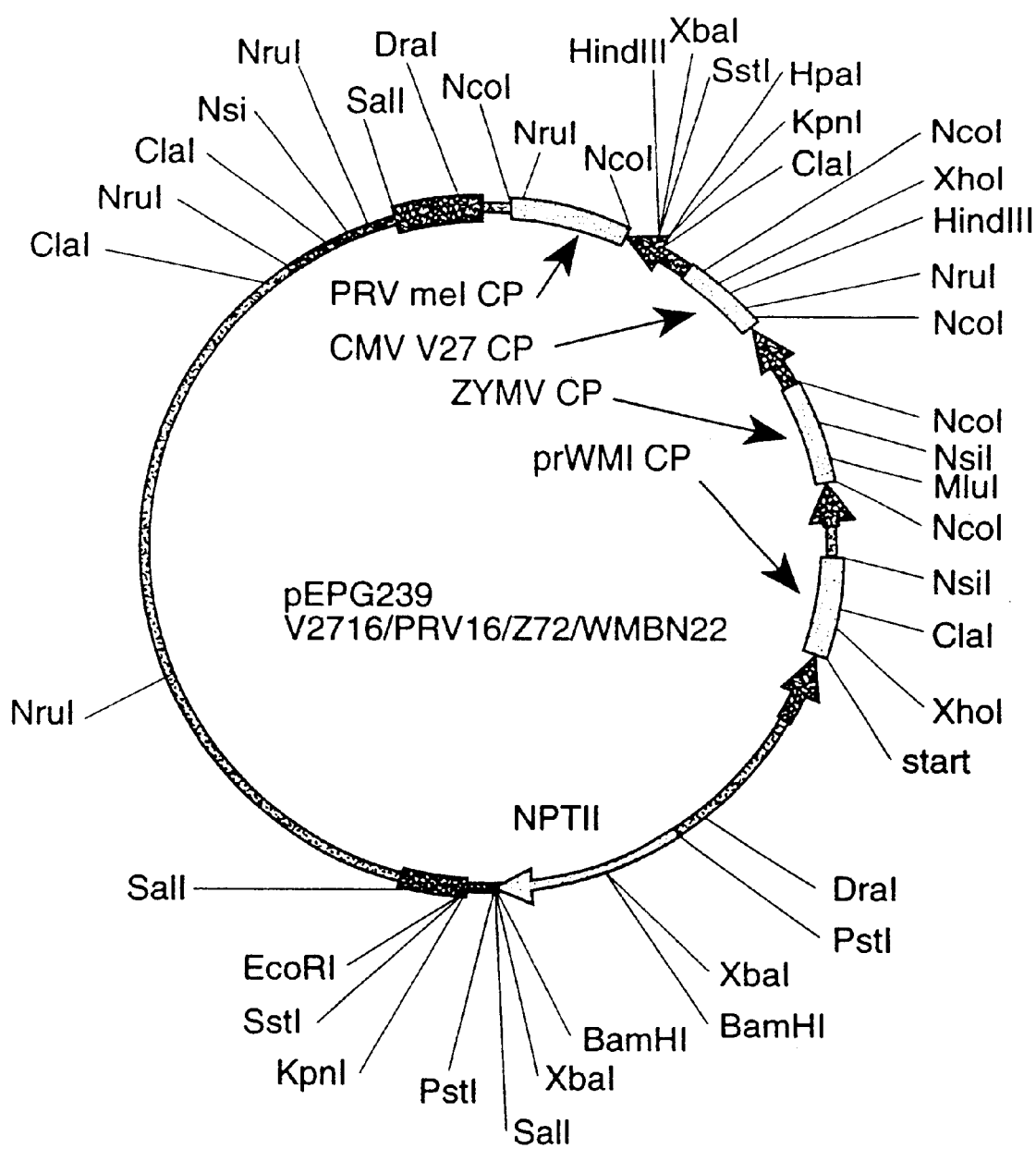
FIG. 6C. Restriction map of pEPG239. This binary plasmid includes the CP expression cassettes for PRV (melon, long), CMV-V27, ZYMV, and WMV-2. For further information on PRV CP genes, refer to Applicants' International Patent Application No. PCT/US95/07272 entitled "Papaya Ringspot Virus Coat Protein Gene" filed on Jun. 7, 1995, incorporated by reference herein. For further information on ZYMV and WMV-2 CP genes, refer to Applicants' International Patent Application No. PCT/US89/03094 filed on Jul. 20, 1989 entitled "Potyvirus Coat Protein Genes and Plants Transformed Therewith", incorporated by reference herein.
Figure 6D:
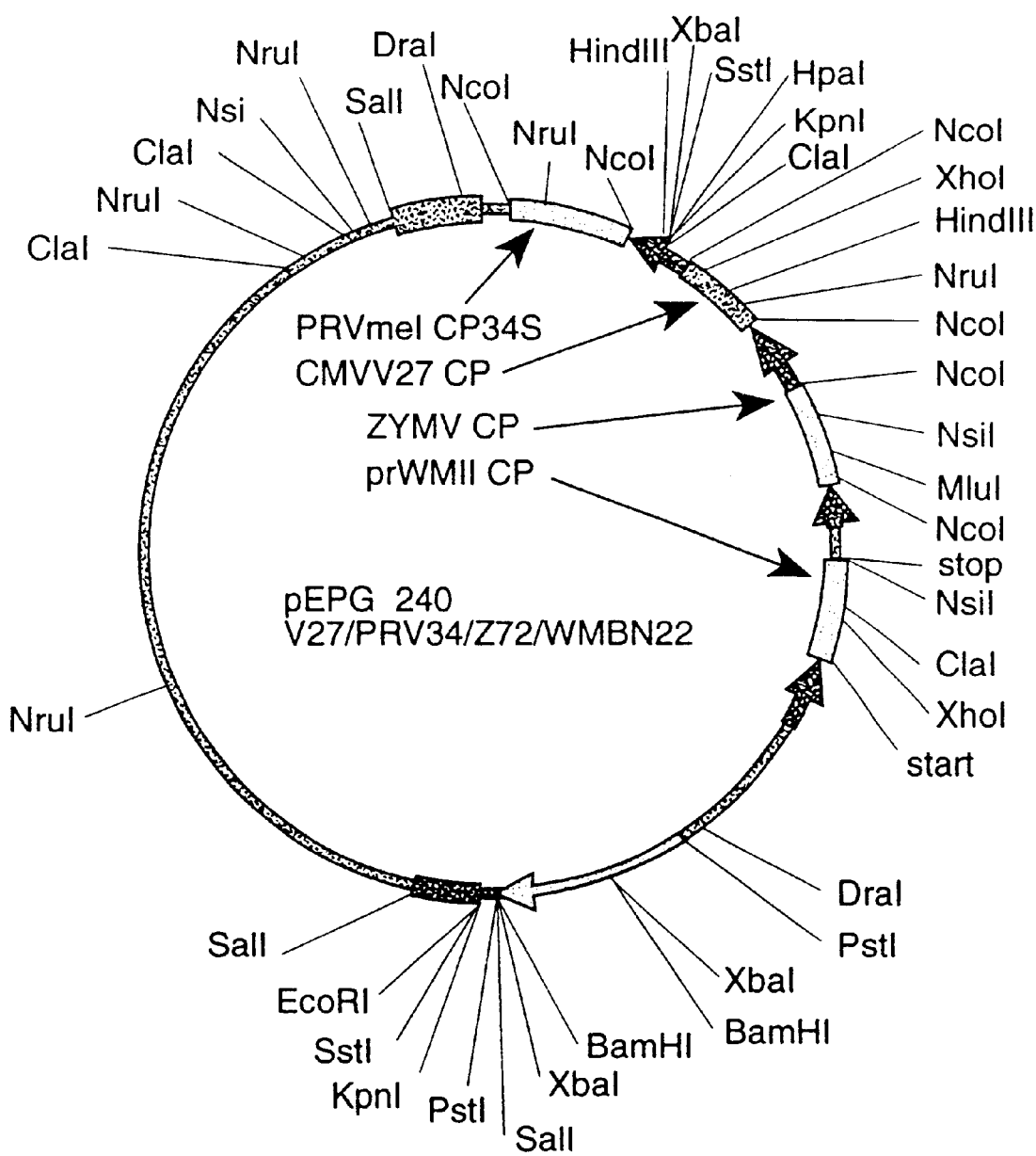
FIG. 6D. Restriction map of pEPG240. This binary plasmid includes the CP expression cassettes for PRV (melon, short), CMV-V27, ZYMV, and WMV-2.
Figure 7A:
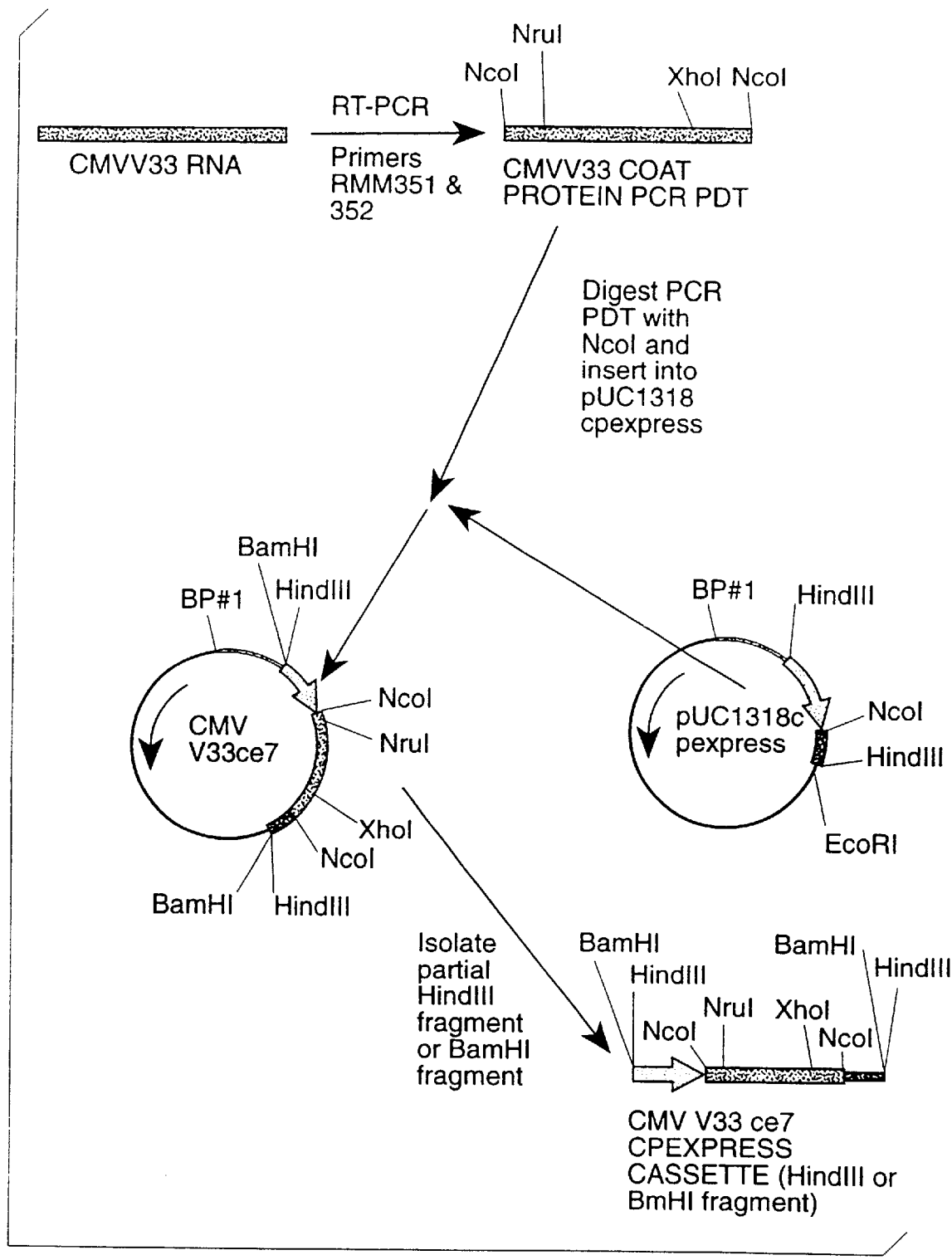
FIG. 7A. Assembly of CMV-V33 CP expression cassette. PCR products of CMV-V33 were installed into pUC1318cpexpress by routine methods.
Figure 7B:
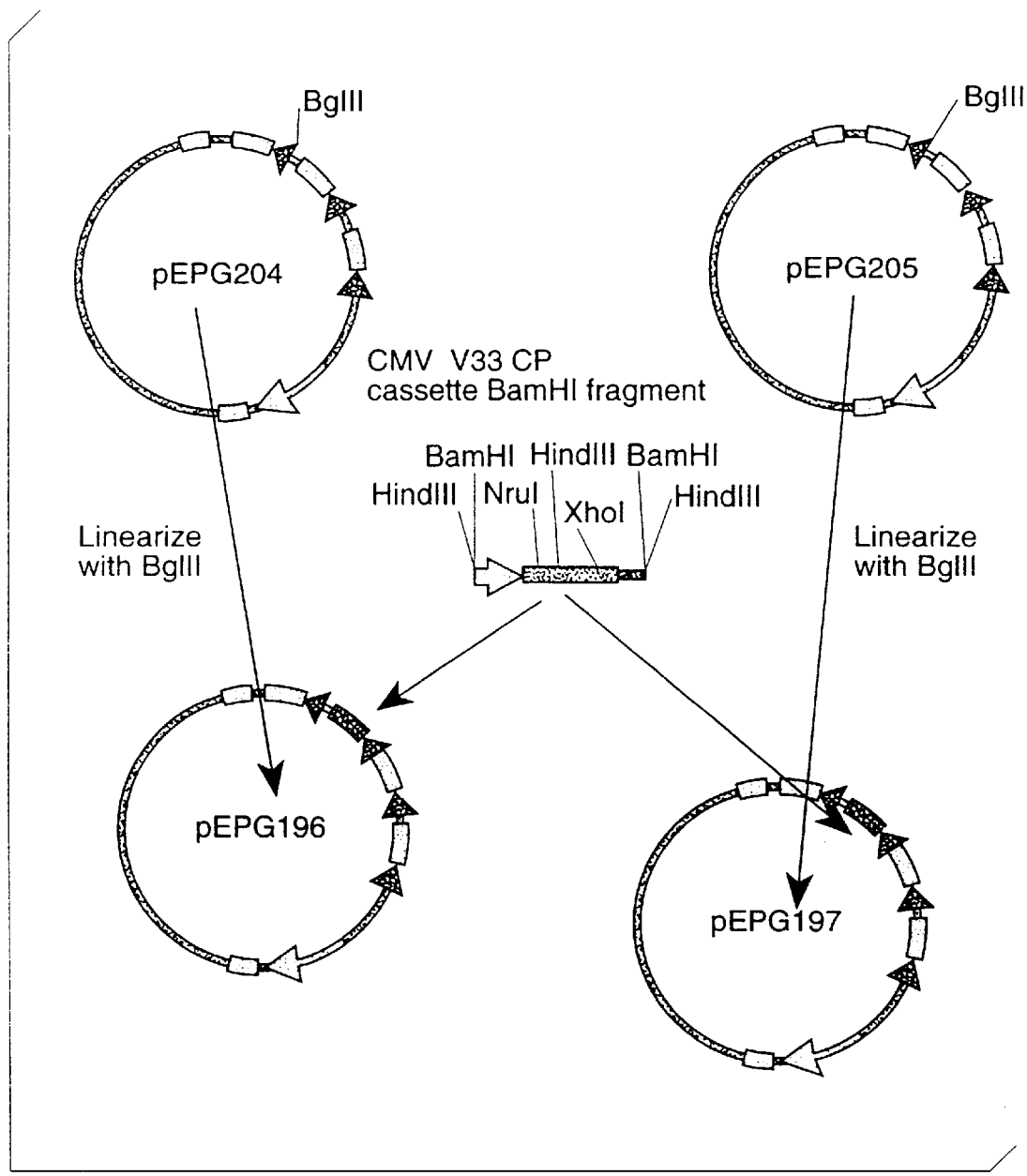
FIG. 7B.
Figure 7C:
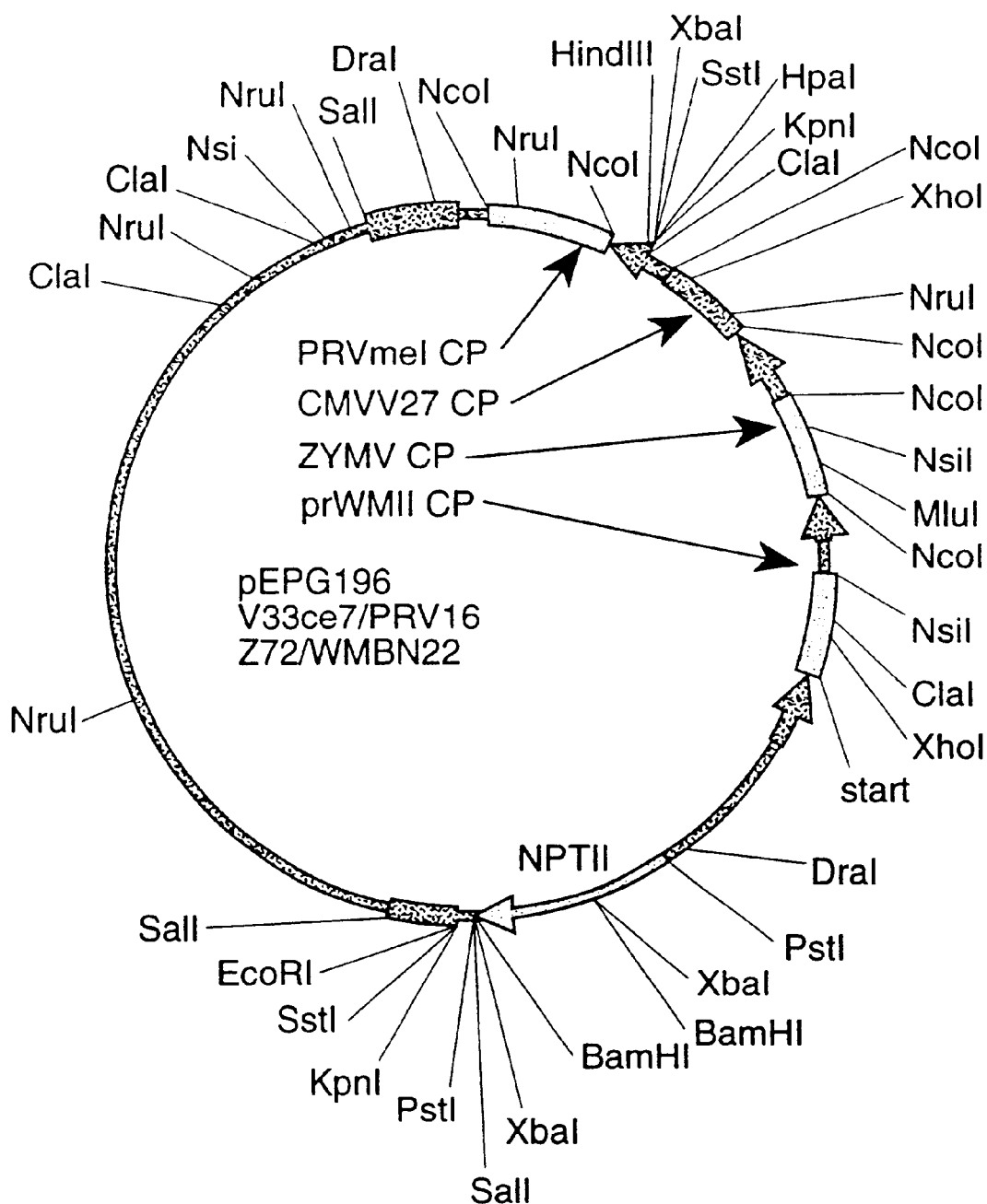
FIG. 7C. Restriction map of pEPG196. This binary plasmid includes the CP expression cassettes for PRV (melon, long), CMV-V33, ZYMV, and WMV-2. Arrows indicate CaMV-35S promoter fragments.
Figure 7D:
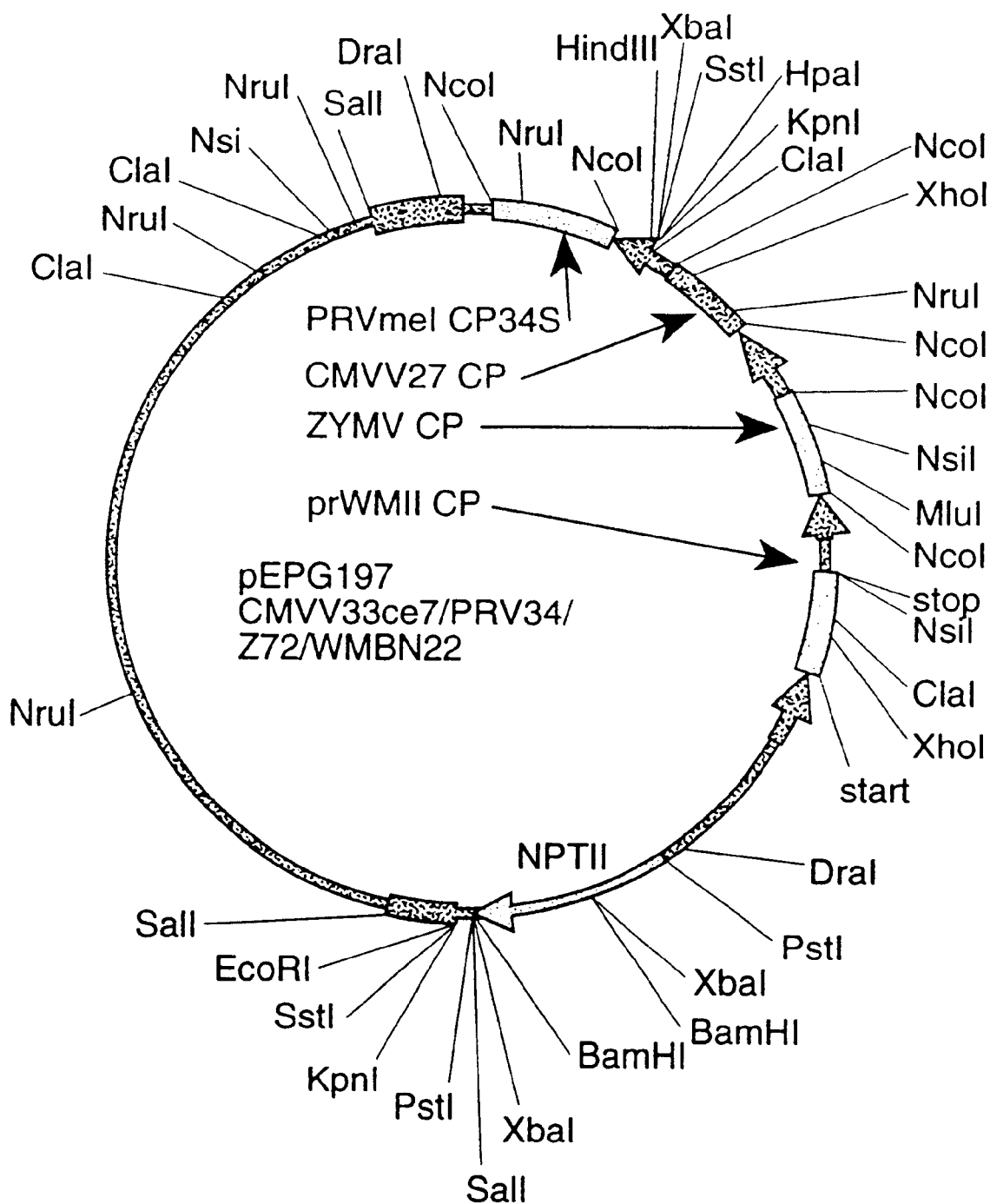
FIG. 7D. Restriction map of pEPG197. This binary plasmid includes the CP expression cassettes for PRV (melon, short), CMV-V33, ZYMV, and WMV-2.

FIGS. 6 and 7 are presented to illustrate the constructions of this invention.

EXAMPLE 1

A. Isolation of CMV RNAs

Zucchini squash plants (20-day old) were inoculated with CMV strains V27, V33, or V34; after 7–10 days, infected leaves were harvested and CMV virus particles were isolated. The procedure used was based on protocols from Lot et al., Annals of Phytopathology, 4:25 (1972), Francki et al., CMI/AAB DESCRIPTIONS OF PLANT VIRUSES, (July, 1979), and Habili and Francki, Virology, 57:292 (1974). Approximately 100 grams (g) of fresh leaves were extracted in an equal weight per volume (w/v) of 0.5 molar (M) Na-citrate (pH 6.5) containing 5 millimolars (mM) EDTA and 100 milliliters (ml) of chloroform. After centrifugation of the extract at 12,000×G for 10 minutes, polyethyleneglycol ("PEG", Sigma Chemical Co. PEG-8000, average molecular weight, Research Grade) was added to the supernatant to a final concentration of 10% and the suspension was stirred for 30–40 minutes at 0–4° C. This suspension was centrifuged at 12,000×G for 10 minutes, and the pellet was resuspended in 40–50 ml of 5 mM Na-borate buffer (pH 9.0) containing 0.5 M EDTA. TRITON X-100 was then added to the virus particle suspension to a final concentration of 2% and stirred on ice for 30 minutes. This suspension was then centrifuged at 19,000×G for 15 minutes, and the supernatant was collected and subsequently centrifuged at 105,000×G for 2 hours. The virus pellet was collected and resuspended in about 2 ml of 5 mM Na-borate buffer (pH 9.0) containing 0.5 mM EDTA. The resuspended virus preparation was applied onto a step sucrose gradient consisting of 5 layers: 5%, 10%, 15%, 20%, and 25% sucrose dissolved in 2.0 mM Na-phosphate buffer (pH 7.5). Gradients were centrifuged at 37,000 rpm in a Sorvall TH641 swinging bucket rotor for 45 minutes. After centrifugation, the virus band was harvested, the virus preparation was dialyzed against Na-borate buffer, and LiCl was added (2 M final concentration) to lyse the virions and to precipitate viral RNA. CMV RNA was dissolved and reprecipitated with ethanol and dissolved in water. By agarose gel electrophoresis, the expected four RNA species were observed.

B. Cloning CMV Coat Protein Genes (a) CMV-V27

The first cDNA strand of CMV-V27 was synthesized with the use of Perkin-Elmer RT-PCR kit reagents and the primer RMM352 (shown in FIG. 4); immediately in the same reaction tube, a PCR was carried out with the use of oligonucleotide primers RMM351 and RMM352 (shown in FIG. 4), following the manufacturer's protocol. The ATG translation start is included in the NcoI site present in primer RMM351. Individual PCR product molecules were cloned using the TA Cloning™ kit (Invitrogen Corp., San Diego, Calif.) into pCRII (included in the TA Cloning™ kit as a linearized plasmid with single 3' dT overhangs at the ends of the molecule). Three clones were isolated for further study: CMVV27TA21, CMVV27TA23, and CMVV27TA26. With the use of a kit (Sequenase 2 purchased from USB, Cleveland, Ohio), the CMV-V27 insert in clone CMVV27TA21 was sequenced.

CMV-V27 was compared to 11 different CMV isolates: Cmvbaul, Cmvq3, Cmvw1, Cmvtrk7, Cmvfc, Cmvi17f, Cmvc, Cmvpr50, Cmw27, Cmvp6, Cmvo, Cmvm, and Cmvy. CMV-V27 CP is similar to CMV-Y in that it contains a serine at position 29 while other strains have an alanine at this position. However, CMV-Y contains a leucine at position 18 while CMV-V27 contains a proline at position 18. In addition, CMV-V27 has a methionine at position 206, no other CMV-C group viruses have a methionine at this position (Baulcombe, D., "Mutational analysis of CMV RNA3: Effects on RNA3 accumulation, RNA4 synthesis and plant infection." Unpublished Direct Submission. Submitted (Jun. 19, 1992) David Baulcombe, The Sainsbury Laboratory, Norwich Research Park, Colney Lane, Norwich, NR2 7UH, United Kingdom; Hayakawa et al., Gene, 71:107 (1988); Hayakawa et al., J. Gen. Virol. 70:499 (1989); Owen et al., J. Gen. Virol., 71:2243 (1990); Pappu et al., "The nucleotide and the deduced amino acid sequences of CP genes of three Puerto Rican isolates of CMV." Unpublished (1992). This sequence is included in the Genebank sequence data base; Salanki et al., "Complete nucleotide sequence of RNA 3 from CMV strain Trk 7. " Unpublished (1993). This sequence is included in the GeneBank data base; Shintaku, J. Gen. Virol. 72:2587 (1991)).

(b) CMV-V33

CMV-V33 was purified and viral RNA extracted from a virion preparation as described above; subsequently single stranded cDNA was synthesized using Perkin-Elmer RT-PCR kit reagents and oligomer primer RMM352. The CP gene of strain V33 was amplified using PCR as described above for V27 with the use of oligomer primers RMM351 and RMM352 (FIG. 4). The V33 CP gene PCR product was digested with NcoI and directly cloned into the expression cassette cpexpress installed into pUC1318 (see Kay and McPherson, Nucleic Acids Research, 15:2779 (1987) for pUC1318; Slightom, Gene, 100:251 (1991) for cpexpress; pUC1318cpexpress is the cpexpress described in Slightom, however it is installed into the HindIII site of the modified pUC plasmid pUC1318 described in detail in Kay and McPherson), rather than into the intermediate vector PCRII. By colony hybridization with a CMV CP probe, a number of clones were identified for further analysis: V33cel, V33ce2, V33ce7, and V33ce9. The CMV-V33 insert in clone V33ce7 was sequenced with the use of a kit (Sequenase 2 purchased from USB, Cleveland, Ohio).

CMV-V33 was compared to 11 different CMV isolates: Cmvbaul, Cmvq3, Cmvw1, Cmvtrk7, Cmvfc, Cmvi17f, Cmvc, Cmvpr50, Cmvv27, Cmvp6, Cmvo, Cmvm, and Cmvy. CMV-V33 has a serine at position 67 while all other CMV strains compared included a proline at this position. At position 196, both CMV-V33 and CMV-Y have a valine residue; all other members of the CMV-C group contains isoleucine at this position. However, at position 184, CMV-V33 has an alanine residue while CMV-Y has a threonine residue. Therefore, CMV-V33 CP is unique (Baulcombe, D., "Mutational analysis of CMV RNA3: Effects on RNA3 accumulation, RNA4 synthesis and plant infection." Unpublished Direct Submission. Submitted (Jun. 19, 1992) David Baulcombe, The Sainsbury Laboratory, Norwich Research Park, Colney Lane, Norwich, NR2 7UH, United Kingdom; Hayakawa et al., Gene, 71:107 (1988); Hayakawa et al., J. Gen. Virol. 70:499 (1989); Owen et al., J. Gen. Virol., 71:2243 (1990); Pappu et al., "The nucleotide and the deduced amino acid sequences of coat protein genes of three Puerto Rican isolates of cucumber mosaic virus." Unpublished (1992). This sequence is included in the GeneBank sequence data base; Salanki et al., "Complete nucleotide sequence of RNA 3 from cucumber mosaic virus strain Trk 7." Unpublished (1993). This sequence is included in the GeneBank data base; Shintaku, J. Gen. Virol. 72:2587 (1991)).

(c) CMV-V34

CMV-V34 RNA was prepared as described above. Subsequently, the first cDNA strand was synthesized using CMV-V34 template in a reaction that included the following: approximately 2 µg CMV-V34 RNA, 1× buffer for Superscript Reverse Transcriptase (supplied by BRLGIBCO, Grand Island, N.Y.), 2 mM dNTPs, oligomer primer RMM352 (37.5 µg/ml), 1.5 microliters (µl) RNasin, and 1µl Superscript Reverse Transcriptase (BRL-GIBCO) in a 20-µl reaction. After this reaction was allowed to proceed for 30 minutes, an aliquot of the first strand reaction was used as a template in a PCR to amplify the CMV-V34 CP gene. The CMV-V34 CP gene PCR product was cloned into the pCRII vector included in the TA Cloning™ Kit supplied by Invitrogen Corp. Two clones were isolated for further study: TA17V34 and TA112V34. The CMV-V34 insert of clone TA17V34 was sequenced with the use of a kit (Sequenase 2 purchased from USB, Cleveland, Ohio). Comparative sequence analysis of the CMV-V34 CP gene with other CMV CP genes (Cmvbaul, Cmvq3, Cmvw1, Cmvtrk7, Cmvfc, Cmvi17f, Cmvc, Cmvpr50, Cmvv27, Cmvp6, Cmvo, Cmvm, and Cmvy showed that the CMV-V34 CP gene is unique (Baulcombe, D. Mutational analysis of CMV RNA3: Effects on RNA3 accumulation, RNA4 synthesis and plant infection. Unpublished Direct Submission. Submitted (Jun. 19, 1992) David Baulcombe, The Sainsbury Laboratory, Norwich Research Park, Colney Lane, Norwich, NR2 7UH, United Kingdom; Hayakawa et al., Gene, 71:107 (1988); Hayakawa et al., J. Gen. Virol. 70:499 (1989); Owen et al., J. Gen. Virol., 71:2243 (1990); Pappu et al., (1992) "The nucleotide and the deduced amino acid sequences of coat protein genes of three Puerto Rican isolates of cucumber mosaic virus." Unpublished. This sequence is included in the GeneBank sequence data base; Salanki et al., "Complete nucleotide sequence of RNA 3 from cucumber mosaic virus strain Trk 7." Unpublished (1993) This sequence is included in the GeneBank data base; Shintaku, J. Gen. Virol. 72:2587 (1991)).

C. Engineering CMV CP Genes (a) CMV-V27

The NcoI fragment in CMVV27TA21 that harbors CMV-V27 CP coding sequences was excised from CMVV27TA21 and inserted into the plant expression cassette cpexpress in pUC18 to give CMVV27TA21ce42. The resulting expression cassette was isolated as a partial HindIII fragment and inserted into the binary vector pGA482G [The parent binary plasmid was pGA482, constructed by An (Plant Physiol., 81:86 (1986)). This binary vector contains the T-DNA border sequences from pTiT37, the selectable marker gene NOS-NPTII (which contains the plant-expressible nopaline gene promoter fused to the bacterial NPTII gene obtained from Tn5), a multiple cloning region, and the cohesive ends of phage lambda (An, Plant Physiol., 81:86 (1986))] to yield pEPG191 and pEPG192. Subsequently, a PRV CP expression cassette was installed to obtain a binary vector that included both CMV-V27 CP and PRV CP expression cassettes.

Alternatively, the CMV-V27 CP NcoI fragment obtained from CMVV27TA21 was installed into pUC1318cp express (see Kay et al., Nucleic Acids Research, 15:2779 (1987) for pUC1318; Slightom, Gene 100:251 (1991) for cpexpress; pUC1318cpexpress is the cpexpress described in Slightom, however it is installed into the HindIII site of the modified pUC plasmid pUC 1318 described in detail in Kay et al.) to give the plasmid CMVV27TA21CE13 (similar to CMVV27TA21ce42). The plasmid pUC1318 provided additional sites (e.g., BamHI and XbaI) with which the cassette could be inserted into the binary vector pGA482G. Subsequently, the bacteria-derived gentamicin-(3)-N-acetyl-transferase gene (Allmansberger et al., Mol. Gen. Genet., 198:514 (1985)) was installed into a SalI site outside of the T-DNA region, adjacent to the left border ($B_L$)). The BamHI fragment harboring the CMV-V27 CP expression cassette was isolated and inserted into the BglII site of the binary plasmid pEPG205 (PRV34/Z72/WMBN22) to give pEPG240 (CMVV27/PRV34/Z72/WMBN22). The BamHI fragment was also installed into the BglII site of the binary plasmid pEPG204 (PRV16/Z72/WMBN22) to yield pEPG239 (CMVV2716/PRV16/Z72/WMBN22) (Table 1). For further information on PRV CP genes, refer to Applicants' International Patent Application No. PCT/US95/07272 entitled "Papaya Ringspot Virus Coat Protein Gene" filed on Jun. 7, 1995, incorporated by reference herein. For further information on ZYMV and WMV-2 CP genes, refer to Applicants' International Patent Application No. PCT/US89/03094 filed on Jul. 20, 1989 entitled "Potyvirus Coat Protein Genes and Plants Transformed Therewith", incorporated by reference herein.

TABLE 1

| Binary | Parental Plasmid | Site | CMVcp Cassette | pEPG# |
|---|---|---|---|---|
| pGA482G | pGA482G | HindIII | CMVV27cpexpress | 191 or 192 |
| pPRBN | pEPG204 (P16sZW) | BglII | CMVV27cpexpress | 239 |
| pPRBN | pEPG204 (P16sZW) | BglII | CMVV27cpexpress | 240 |
| pPRBN | pEPG106 (ZW) | HindIII | CMVV27cpexpress | 243 |
| pGA482G | pGA482G | HindIII | CMVV33ce7 | 198 |
| pPRBN | pEPG106 (ZW) | HindIII | CMVV33ce7 | 244 |
| pPRBN | pEPG204 (P16sZW) | BglII | CMVV27ce7 | 196 |
| pPRBN | pEPG205 (P34sZW) | BglII | CMVV27ce7 | 197 |
| pGA482G | pGA482G | HindIII | 17V34cpexp113 | 190 |

(b) CMV-V33

Subsequently, both HindIII and BamHI fragments were excised from clone V33ce7; these fragments carried the complete expression cassette for CMV-V33 CP gene. The BamHI fragment (V33 CP expression cassette) was inserted into the BglII site of pEPG204 (PRV16/ZY72/WMBN22) to obtain pEPG196. The BamHI fragment was also inserted into the BglII site of pEPG205 (PRV34/ZY72/WMBN22) to obtain pEPG197 (V3329/PRV34/ZY72/WMBN22). The HindIII fragment harboring the V33 CP cassette was installed into pGA482G to obtain pEPG198 (Table 1).

(c) CMV-V34

An NcoI fragment excised from clone TA17V34 was installed into the NcoI site of pUC1318 cpexpress. A resulting plasmid that includes the CMV-V34 coding NcoI fragment inserted in the sense orientation is 17V34/cpexp113. A partial HindIII fragment from the plasmid 17V34/cpexp113 was isolated and installed into pGA482G to yield pEPG190 (Table 1).

(d) Agrobacterium Strains

The binary plasmids described here, such as pPRBN (for further information on these plasmids, refer to Applicants' International Patent Application No. PCT/US95/06261 entitled "Transgenic Plants Expressing DNA Constructs Containing a Plurality of Genes to Impart Virus Resistance" filed on Jun. 7, 1995, incorporated by reference herein) or their derivatives, can be transferred into Agrobacterium strains A208, C58, LBA4404, C58Z707, A4RS, A4RS (pRi278b), Mog301 and others. Strains A208, C58, LBA4404, and A4RS are available from ATCC, 12301 Parklawn Drive, Rockville, Md. A4RS (pRi278b) was obtained from Dr. F. Casse-Delbart, C.N.R.A., Route de Saint Cyr, F78000, Versailles, France. C58Z707 was obtained from Dr. A. G. Hepburn, University of Illinois, Urbana, Ill. Mog301 was obtained from Mogen NV, Leiden, Netherlands.

D. Transfer of CMV Coat Protein Genes to Tobacco

In order to test whether the CMV CP gene constructs described herein confer protection against CMV challenge with homologous strains, some of the binary plasmids listed above (e.g., pEPG197, pEPG198, pEPG239, and pEPG240) have been used to insert these novel CMV CP genes into *Nicotiana tobacum*. Agrobacterium-mediated transfer of the plant expressible CMV CP genes described herein was done using the methods described in PCT published application WO 89/05859, entitled "Agrobacterium Mediated Transformation of Germinating Plant Seeds."

Five $R_1$ progeny lines of *Nicotiana t.* transformed with the binary plasmid pEPG239 and five $R_1$ progeny lines of *Nicotiana t.* transformed with the binary plasmid EPG240 have been obtained. These binary plasmids include the CP gene of CMV-V27. The ten $R_0$ parental plants of these lines were assayed for NPTII protein expression by ELISA. They each expressed NPTII protein by ELISA. Furthermore, these ten lines were assayed for both the NPTII and CMV-V27 CP genes by PCR analysis. PCR analysis detected both genes in all ten $R_0$ plants.

The binary plasmid pEPG198 was used to obtain 11 $R_0$ transgenic *Nicotiana t.* plants. By PCR analysis, the CMV-V33 CP gene was detected in nine of the eleven $R_0$ plants tested.

E. Cloning and Engineering CMV-A35 PC Gene 20-day-old zucchini squash plants in the greenhouse were inoculated with CMV-A35; after 7–10 days infected leaves were harvested. Total RNA was isolated from these infected plants by the use of Tri-Reagent and the instructions provided with the reagent (Molecular Research Center, Inc., Cincinnati, Ohio.). Single-stranded cDNA was synthesized using total RNA template. The reaction included 1× first Strand cDNA Synthesis Buffer (GIBCO-BRL), 1 mM dNTP's (Pharmacia), 2 $\mu$l oligonucleotide primer RMM352 (150 $\mu$g/ml),2 $\mu$l RNasin (Promega), and 1 $\mu$l RTase Superscript II (GIBCO-BRL) in a 20 $\mu$l reaction volume. The CMV-A35 CP gene was PCR amplified with the use of CMV CP-specific primers RMM351 and 352. The PCR included 3 $\mu$l of the cDNA synthesis reaction described above, 8 $\mu$l of each primer RMM351 and RMM352 (150 $\mu$g/$\mu$l stock), 5 $\mu$l 10× reaction buffer, 4 $\mu$l dNTP's (10 mM), 1.5 $\mu$l $MgCl_2$ (50 mM), and 0.5 $\mu$l, Taq polymerase (BRL-GIBCO). PCR conditions were carried out as follows: 93° 45 sec, 50 ° 45 sec, then 72° 180 sec for 30 cycles, then 72° for 5 min, then hold at 4°. PCR products were visualized by agarose gel electrophoresis and subsequently cloned. PCR product molecules were cloned into the PCRII vector supplied with the TA cloning kit (Invitrogen Corp.) Four clones were identified and restriction mapped, however, none were sequenced for further analysis.

Alternatively, an aliquot of the CMV-A35 PCR product was digested with NcoI and ligated it into the NcoI site of pUC19B2 cpexpress to give the plasmid CMV35Acpexp33. The CP insert of this plasmid was sequenced with the use of the Sequenase II Kit supplied by USBiochemical (FIG. 8). Sequence analysis reveals that CMV-A35 CP sequence differs from the CP sequences of CMV C, V27, V33, V34, and WL (FIGS. 9 and 10). For example, A35 differs from other CMV-C strains at amino acid position #26 (FIG. 9). Examination of the nucleotide sequence comparisons differs from other CMV CP genes characterized (FIG. 10).

A BamHI/BI1II fragment was excised from A35cpexp33 and installed into the unique BglII site pGA482G. The plasmid pUC19B2cpexp provides a BamHI site at the 5' end of the cpexp cassette and a BglII site at the 3' end of the expression cassette. Upon insertion into a BglII site, the unique BglII site of the binary plasmid pGA482 is maintained for subsequent insertions of gene cassettes. Binary plasmids that include the CMV-A35 expression cassette are being transformed into various Agrobacterium strains (e.g., C58Z707, Mog301, and LBA4404). These Agrobacterium strains are used to transform plants to impart resistance to CMV CARNA5.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. An isolated and purified DNA molecule comprising DNA encoding the coat protein of the V33 strain of cucumber mosaic virus.

2. The isolated and purified DNA molecule of claim 1 wherein the DNA molecule comprises the nucleotide sequence shown in SEQ ID NO:3.

3. A vector comprising a chimeric expression cassette comprising the DNA molecule of claim 1, a promoter and a polyadenylation signal, wherein the promoter is operably linked to the DNA molecule, and the DNA molecule is operably linked to the polyadenylation signal.

4. The vector of claim 3, wherein the promoter is the cauliflower mosaic virus 35S promoter.

5. The vector of claim 4 wherein the polyadenylation signal is the polyadenylation signal of the cauliflower mosaic 35S gene.

6. A bacterial cell comprising the vector of claim 4.

7. The bacterial cell of claim 6 wherein the bacterial cell is selected from the group consisting of an *Agrobacterium tumefaciens* cell and an *Agrobacterium rhizogenes* cell.

8. A transformed plant cell transformed with the vector of claim 4.

9. The transformed plant cell of claim 8 wherein the promoter is cauliflower mosaic virus 35S promoter and the polyadenylation signal is the polyadenylation signal of the cauliflower mosaic 35S gene.

10. A plant selected from the family Cucurbitaceae comprising a plurality of transformed cells of claim 8.

11. A plant selected from the family Solanaceae comprising a plurality of transformed cells of claim 8.

12. A method of preparing a cucumber mosaic viral resistant plant comprising:

(a) transforming plant cells with a chimeric expression cassette comprising a promoter functional in plant cells operably linked to a DNA molecule that encodes a coat protein; wherein the DNA molecule is from the cucumber mosaic virus strain V33;

(b) regenerating the plant cells to provide a differentiated plant; and (c) identifying a transformed plant that expresses the said cucumber mosaic virus coat protein at a level sufficient to render the plant resistant to infection by cucumber mosaic virus strain V33.

13. The method of claim 12 wherein the plant is a dicot.

* * * * *

SEQUENCE LISTING

```
(1) GENERAL INFORMATION:

(iii) NUMBER OF SEQUENCES: 15

(2) INFORMATION FOR SEQ ID NO: 1:

(i) SEQUENCE CHARACTERISTICS:
          (A) LENGTH: 772 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTI-SENSE: NO (vi) ORIGINAL SOURCE:
          (A) ORGANISM: Cucumber Mosaic Virus
          (C) INDIVIDUAL ISOLATE: V-27

(ix) FEATURE:
          (A) NAME/KEY: CDS
          (B) LOCATION: 3..660

(xi) SEQUENCE DESCRIPTION: SEQ ID NO: 1:

CC ATG GAC AAA TCT GAA TCA ACC AGT GCT GGT CGT AAC CGT CGG CGT        47
   Met Asp Lys Ser Glu Ser Thr Ser Ala Gly Arg Asn Arg Arg Arg
     1               5                  10                  15
```

```
CGT CCG CGT CGT GGT TCC CGC TCC GCC TCC TCC TCC TCG GAT GCT AAC      95
Arg Pro Arg Arg Gly Ser Arg Ser Ala Ser Ser Ser Ser Asp Ala Asn
             20                  25                  30

TTT AGA GTC TTG TCG CAG CAG CTT TCG CGA CTT AAC AAG ACG TTA GCA     143
Phe Arg Val Leu Ser Gln Gln Leu Ser Arg Leu Asn Lys Thr Leu Ala
         35                  40                  45

GCT GGT CGT CCA ACT ATT AAC CAC CCA ACC TTT GTA GGG AGT GAA CGC     191
Ala Gly Arg Pro Thr Ile Asn His Pro Thr Phe Val Gly Ser Glu Arg
             50                  55                  60

TGT AAA CCT GGG TAC ACG TTC ACA TCT ATT ACC CTA AAG CCA CCA AAA     239
Cys Lys Pro Gly Tyr Thr Phe Thr Ser Ile Thr Leu Lys Pro Pro Lys
         65                  70                  75

ATA GAC CGT GGG TCT TAT TAC GGT AAA AGG TTG TTA TTA CCT GAT TCA     287
Ile Asp Arg Gly Ser Tyr Tyr Gly Lys Arg Leu Leu Leu Pro Asp Ser
 80                  85                  90                  95

GTC ACG GAA TAT GAT AAG AAG CTT GTT TCG CGC ATT CAA ATT CGA GTT     335
Val Thr Glu Tyr Asp Lys Lys Leu Val Ser Arg Ile Gln Ile Arg Val
             100                 105                 110

AAT CCT TTG CCG AAA TTT GAT TCT ACC GTG TGG GTA ACA GTC CGT AAA     383
Asn Pro Leu Pro Lys Phe Asp Ser Thr Val Trp Val Thr Val Arg Lys
             115                 120                 125

GTT CCT GCC TCC TCG GAC TTA TCC GTT GCC GCC ATC TCT GCT ATG TTC     431
Val Pro Ala Ser Ser Asp Leu Ser Val Ala Ala Ile Ser Ala Met Phe
             130                 135                 140

GCG GAC GGA GCC TCA CCG GTA CTG GTT TAT CAG TAT GCT GCA TCT GGA     479
Ala Asp Gly Ala Ser Pro Val Leu Val Tyr Gln Tyr Ala Ala Ser Gly
             145                 150                 155

GTC CAA GCT AAC AAC AAA TTG TTG TAT GAT CTT TCG GCG ATG CGC GCT     527
Val Gln Ala Asn Asn Lys Leu Leu Tyr Asp Leu Ser Ala Met Arg Ala
160                 165                 170                 175

GAT ATA GGT GAC ATG AGA AAG TAC GCC GTC CTC GTG TAT TCA AAA GAC     575
Asp Ile Gly Asp Met Arg Lys Tyr Ala Val Leu Val Tyr Ser Lys Asp
             180                 185                 190

GAT GCG CTC GAG ACG GAC GAG CTA GTA CTT CAT GTT GAC ATC GAG CAC     623
Asp Ala Leu Glu Thr Asp Glu Leu Val Leu His Val Asp Ile Glu His
             195                 200                 205

CAA CGT ATT CCC ACG TCT GGG ATG CTC CCA GTC TGA T TCCGTGTTCC        670
Gln Arg Ile Pro Thr Ser Gly Met Leu Pro Val  *
             210                 215

CAGAACCCTC CCTCCGATTT CTGTGGCGGG AGCTGAGTTG GCAGTTCTGC TATAAACTGT   730

CTGAAGTCAC TAAACGTTTC ACGGTGAACG GGTTGTCCAT GG                      772

(2) INFORMATION FOR SEQ ID NO: 2:

(i) SEQUENCE CHARACTERISTICS:
        (A) LENGTH: 218 amino acids
        (B) TYPE: amino acid
        (D) TOPOLOGY: linear (ii) MOLECULE TYPE: protein (xi) SEQUENCE DESCRIPTION: SEQ ID NO: 2:

Met Asp Lys Ser Glu Ser Thr Ser Ala Gly Arg Asn Arg Arg Arg
 1               5                  10                  15

Pro Arg Gly Ser Arg Ser Ala Ser Ser Ser Asp Ala Asn Phe
             20                  25                  30

Arg Val Leu Ser Gln Gln Leu Ser Arg Leu Asn Lys Thr Leu Ala Ala
         35                  40                  45

Gly Arg Pro Thr Ile Asn His Pro Thr Phe Val Gly Ser Glu Arg Cys
```

```
                    50                    55                    60
Lys Pro Gly Tyr Thr Phe Thr Ser Ile Thr Leu Lys Pro Pro Lys Ile
 65                    70                    75                    80

Asp Arg Gly Ser Tyr Tyr Gly Lys Arg Leu Leu Pro Asp Ser Val
                85                    90                    95

Thr Glu Tyr Asp Lys Lys Leu Val Ser Arg Ile Gln Ile Arg Val Asn
                  100                   105                   110

Pro Leu Pro Lys Phe Asp Ser Thr Val Trp Val Thr Val Arg Lys Val
            115                   120                   125

Pro Ala Ser Ser Asp Leu Ser Val Ala Ala Ile Ser Ala Met Phe Ala
        130                   135                   140

Asp Gly Ala Ser Pro Val Leu Val Tyr Gln Tyr Ala Ala Ser Gly Val
145                   150                   155                   160

Gln Ala Asn Asn Lys Leu Leu Tyr Asp Leu Ser Ala Met Arg Ala Asp
                  165                   170                   175

Ile Gly Asp Met Arg Lys Tyr Ala Val Leu Val Tyr Ser Lys Asp Asp
                  180                   185                   190

Ala Leu Glu Thr Asp Glu Leu Val Leu His Val Asp Ile Glu His Gln
            195                   200                   205

Arg Ile Pro Thr Ser Gly Met Leu Pro Val
        210                   215

(2) INFORMATION FOR SEQ ID NO: 3:

(i) SEQUENCE CHARACTERISTICS:
        (A) LENGTH: 792 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: CUCUMBER MOSAIC VIRUS
        (B) STRAIN: v-33

(ix) FEATURE:
        (A) NAME/KEY: CDS
        (B) LOCATION: 3..660

(xi) SEQUENCE DESCRIPTION: SEQ ID NO: 3:

CC ATG GAC AAA TCT GAA TCA ACC AGT GCT GGT CGT AAC CGT CGA CGT         47
   Met Asp Lys Ser Glu Ser Thr Ser Ala Gly Arg Asn Arg Arg Arg
   220                   225                   230

CGT CCG CGT CGT GGT TCC CGC TCC GCC CCC TCC TCC GCG GAT GCC AAC        95
Arg Pro Arg Arg Gly Ser Arg Ser Ala Pro Ser Ser Ala Asp Ala Asn
235                   240                   245                   250

TTT AGA GTC TTG TCG CAG CAG CTT TCG CGA CTT AAT AAG ACG TTG TCA       143
Phe Arg Val Leu Ser Gln Gln Leu Ser Arg Leu Asn Lys Thr Leu Ser
                  255                   260                   265

GCT GGT CGT CCA ACT ATT AAC CAC CCA ACC TTT GTA GGG AGT GAG CGT       191
Ala Gly Arg Pro Thr Ile Asn His Pro Thr Phe Val Gly Ser Glu Arg
            270                   275                   280

TGT AAA TCT GGG TAC ACG TTC ACA TCT ATT ACC CTA AAG CCG CCG AAA       239
Cys Lys Ser Gly Tyr Thr Phe Thr Ser Ile Thr Leu Lys Pro Pro Lys
            285                   290                   295

ATA GAC CGT GGG TCT TAT TAT GGT AAA AGG TTG TTA TTA CCT GAT TCA       287
Ile Asp Arg Gly Ser Tyr Tyr Gly Lys Arg Leu Leu Leu Pro Asp Ser
```

```
                300                 305                 310
GTC ACA GAA TAT GAT AAG AAA CTT GTT TCG CGC ATT CAA ATT CGA GTT      335
Val Thr Glu Tyr Asp Lys Lys Leu Val Ser Arg Ile Gln Ile Arg Val
315                 320                 325                 330

AAT CCC TTG CCG AAA TTT GAT TCT ACC GTG TGG GTG ACA GTC CGT AAA      383
Asn Pro Leu Pro Lys Phe Asp Ser Thr Val Trp Val Thr Val Arg Lys
                335                 340                 345

GTT CCT GCC TCC TCG GAC TTA TCC GTT GCC GCC ATC TCT GCT ATG TTT      431
Val Pro Ala Ser Ser Asp Leu Ser Val Ala Ala Ile Ser Ala Met Phe
                350                 355                 360

GCG GAC GGA GCC TCA CCG GTA CTG GTT TAT CAG TAC GCT GCA TCT GGA      479
Ala Asp Gly Ala Ser Pro Val Leu Val Tyr Gln Tyr Ala Ala Ser Gly
                365                 370                 375

GTC CAA GCT AAC AAC AAA TTG TTG TAT GAT CTT TCG GCG ATG CGC GCT      527
Val Gln Ala Asn Asn Lys Leu Leu Tyr Asp Leu Ser Ala Met Arg Ala
380                 385                 390

GAT ATA GGC GAC ATG AGA AAG TAC GCC GTC CTC GTG TAT TCA AAA GAC      575
Asp Ile Gly Asp Met Arg Lys Tyr Ala Val Leu Val Tyr Ser Lys Asp
395                 400                 405                 410

GAT GCA CTC GAG ACG GAC GAG CTA GTA CTT CAT GTT GAC GTC GAG CAC      623
Asp Ala Leu Glu Thr Asp Glu Leu Val Leu His Val Asp Val Glu His
                415                 420                 425

CAA CGC ATT CCC ACG TCT GGG GTG CTC CCA GTA TAA T TCTGTGCTTT         670
Gln Arg Ile Pro Thr Ser Gly Val Leu Pro Val  *
                430                 435

CCAGAACCCT CCCTCCGATT CTGTGGCGG GAGCTGAGTT GGCAGTTCTG CTGTAAACTG     730

TCTGAAGTCA CTAAACGTTT TACGGTGAAC GGGTTGTCCA TGGGTTTCGG TTTTTTTGTT    790

AA                                                                   792
```

(2) INFORMATION FOR SEQ ID NO: 4:

(i) SEQUENCE CHARACTERISTICS:
        (A) LENGTH: 218 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Asp Lys Ser Glu Ser Thr Ser Ala Gly Arg Asn Arg Arg Arg Arg
1               5                   10                  15

Pro Arg Arg Gly Ser Arg Ser Ala Pro Ser Ser Ala Asp Ala Asn Phe
                20                  25                  30

Arg Val Leu Ser Gln Gln Leu Ser Arg Leu Asn Lys Thr Leu Ser Ala
                35                  40                  45

Gly Arg Pro Thr Ile Asn His Pro Thr Phe Val Gly Ser Glu Arg Cys
        50                  55                  60

Lys Ser Gly Tyr Thr Phe Thr Ser Ile Thr Leu Lys Pro Pro Lys Ile
65                  70                  75                  80

Asp Arg Gly Ser Tyr Tyr Gly Leu Arg Leu Leu Leu Pro Asp Ser Val
                85                  90                  95

Thr Glu Tyr Asp Lys Lys Leu Val Ser Arg Ile Gln Ile Arg Val Asn
                100                 105                 110

Pro Leu Pro Lys Phe Asp Ser Thr Val Trp Val Thr Val Arg Lys Val
        115                 120                 125

Pro Ala Ser Ser Asp Leu Ser Val Ala Ala Ile Ser Ala Met Phe Ala
        130                 135                 140
```

```
Asp Gly Ala Ser Pro Val Leu Val Tyr Gln Tyr Ala Ser Gly Val
145                 150                 155                 160

Gln Ala Asn Asn Lys Leu Leu Tyr Asp Leu Ser Ala Met Arg Ala Asp
                165                 170                 175

Ile Gly Asp Met Arg Lys Tyr Ala Val Leu Val Tyr Ser Lys Asp Asp
            180                 185                 190

Ala Leu Glu Thr Asp Glu Leu Val Leu His Val Asp Val Glu His Gln
        195                 200                 205

Arg Ile Pro Thr Ser Gly Val Leu Pro Val
    210                 215
```

(2) INFORMATION FOR SEQ ID NO: 5:

(i) SEQUENCE CHARACTERISTICS:
        (A) LENGTH: 771 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (A) ORGANISM: Cucumber mosaic virus
        (B) STRAIN: V-34

(ix) FEATURE:
        (A) NAME/KEY: CDS
        (B) LOCATION: 3..660
        (D) OTHER INFORMATION: /codon_start= 3
            /function= "ENCAPSIDATES VIRUS RNA"
            /product= "COAT PROTEIN"
            /gene= "CP"
            /number= 1
            /standard_name= "COAT PROTEIN"

(xi) SEQUENCE DESCRIPTION: SEQ ID NO: 5:

```
CC ATG GAC AAA TCT GAA TCA ACC AGT GCT GGT CGT AAC CGT CGA CGT        47
   Met Asp Lys Ser Glu Ser Thr Ser Ala Gly Arg Asn Arg Arg Arg
   220                 225                 230

CGT CCG CGT CGT GGT TCC CGC TCC GCT TCC TCC TCT TCG GAT GCT AAC        95
Arg Pro Arg Arg Gly Ser Arg Ser Ala Ser Ser Ser Ser Asp Ala Asn
235                 240                 245                 250

TTT AGA GTC TTG TCG CAG CAG CTT TCG CGA CTT AAC AAG ACG TTA GCA       143
Phe Arg Val Leu Ser Gln Gln Leu Ser Arg Leu Asn Lys Thr Leu Ala
                255                 260                 265

GCT GGT CGT CCA ACT ATT AAC CAC CCA ACC TTT GTA GGG AGT GAA CGC       191
Ala Gly Arg Pro Thr Ile Asn His Pro Thr Phe Val Gly Ser Glu Arg
            270                 275                 280

TGT AGA CCT GGG TAC ACG TTC ACA TCT ATT ACC CTA AAG CCA CCA AAA       239
Cys Arg Pro Gly Tyr Thr Phe Thr Ser Ile Thr Leu Lys Pro Pro Lys
        285                 290                 295

ATA GAC CGC GGG TCT TAC TAC GGT AAA AGG TTG TTA CTA CCT GAT TCA       287
Ile Asp Arg Gly Ser Tyr Tyr Gly Lys Arg Leu Leu Leu Pro Asp Ser
    300                 305                 310

GTC ACG GAA TAT GAT AAG AAG CTT GTT TCG CGC ATT CAA ATT CGA GTT       335
Val Thr Glu Tyr Asp Lys Lys Leu Val Ser Arg Ile Gln Ile Arg Val
315                 320                 325                 330

AAT CCT TTG CCG AAA TTT GAT TCT ACC GTG TGG GTG ACA GTT CGT AAA       383
Asn Pro Leu Pro Lys Phe Asp Ser Thr Val Trp Val Thr Val Arg Lys
                335                 340                 345

GTT CCT GCC TCC TCG GAC TTA TCC GTT GCC GCC ATC TCT GCT ATG TTC       431
Val Pro Ala Ser Ser Asp Leu Ser Val Ala Ala Ile Ser Ala Met Phe
            350                 355                 360
```

-continued

```
GCG GAC GGA GCC TCA CCG GTA CTG GTT TAT CAG TAT GCT GCA TCT GGA        479
Ala Asp Gly Ala Ser Pro Val Leu Val Tyr Gln Tyr Ala Ala Ser Gly
        365                 370                 375

GTT CAA GCT AAC AAC AAA TTG TTG TAT GAT CTT TCG GCG ATG CGC GCT        527
Val Gln Ala Asn Asn Lys Leu Leu Tyr Asp Leu Ser Ala Met Arg Ala
        380                 385                 390

GAT ATA GGT GAC ATG AGA AAG TAC GCC GTC CTC GTG TAT TCA AAA GAC        575
Asp Ile Gly Asp Met Arg Lys Tyr Ala Val Leu Val Tyr Ser Lys Asp
395                 400                 405                 410

GAT GCA CTC GAG ACG GAC GAG CTA GTA CTT CAT GTT GAC ATC GAG CAC        623
Asp Ala Leu Glu Thr Asp Glu Leu Val Leu His Val Asp Ile Glu His
                415                 420                 425

CAA CGC ATT CCC ACG TCT GGG GTG CTC CCA GTT TGA T TCCGTGTTCC           670
Gln Arg Ile Pro Thr Ser Gly Val Leu Pro Val  *
                430                 435

AGAACCCTCC CTCCGATTTC TGTGGCGGGA GCTGAGTTGG CAGTTCTGCT ATAAACTGTC      730

TGAAGTCACT AAACGTTTTA CGGTGAACGG GTTGTCCATG G                          771
```

(2) INFORMATION FOR SEQ ID NO: 6:

(i) SEQUENCE CHARACTERISTICS:
        (A) LENGTH: 218 amino acids
        (B) TYPE: amino acid
        (D) TOPOLOGY: linear (ii) MOLECULE TYPE: protein (xi) SEQUENCE DESCRIPTION: SEQ ID NO: 6:

```
Met Asp Lys Ser Glu Ser Thr Ser Ala Gly Arg Asn Arg Arg Arg Arg
1               5                   10                  15

Pro Arg Arg Gly Ser Arg Ser Ala Ser Ser Ser Asp Ala Asn Phe
                20                  25                  30

Arg Val Leu Ser Gln Gln Leu Ser Arg Leu Asn Lys Thr Leu Ala Ala
            35                  40                  45

Gly Arg Pro Thr Ile Asn His Pro Thr Phe Val Gly Ser Glu Arg Cys
    50                  55                  60

Arg Pro Gly Tyr Thr Phe Thr Ser Ile Thr Leu Lys Pro Pro Lys Ile
65                  70                  75                  80

Asp Arg Gly Ser Tyr Tyr Gly Lys Arg Leu Leu Leu Pro Asp Ser Val
                85                  90                  95

Thr Glu Tyr Asp Lys Lys Leu Val Ser Arg Ile Gln Ile Arg Val Asn
            100                 105                 110

Pro Leu Pro Lys Phe Asp Ser Thr Val Trp Val Thr Arg Lys Val
        115                 120                 125

Pro Ala Ser Ser Asp Leu Ser Val Ala Ala Ile Ser Ala Met Phe Ala
    130                 135                 140

Asp Gly Ala Ser Pro Val Leu Val Tyr Gln Tyr Ala Ala Ser Gly Val
145                 150                 155                 160

Gln Ala Asn Asn Lys Leu Leu Tyr Asp Leu Ser Ala Met Arg Ala Asp
                165                 170                 175

Ile Gly Asp Met Arg Lys Tyr Ala Val Leu Val Tyr Ser Lys Asp Asp
            180                 185                 190

Ala Leu Glu Thr Asp Glu Leu Val Leu His Val Asp Ile Glu His Gln
        195                 200                 205

Arg Ile Pro Thr Ser Gly Val Leu Pro Val
    210                 215
```

(2) INFORMATION FOR SEQ ID NO: 7:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide Primer RMM (iii) HYPOTHETICAL: NO (iv) ANTI-SENSE: NO (xi) SEQUENCE DESCRIPTION: SEQ ID NO: 7:

```
CGTAGAATTC AGTCGAGCCA TGGAC                                           25
```

(2) INFORMATION FOR SEQ ID NO: 8:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide Primer (iii) HYPOTHETICAL: NO (iv) ANTI-SENSE: NO (xi) SEQUENCE DESCRIPTION: SEQ ID NO: 8:

```
GACCACTCGA GCCGTAAGCT CCATGGAC                                        28
```

(2) INFORMATION FOR SEQ ID NO: 9:

(i) SEQUENCE CHARACTERISTICS:
        (A) LENGTH: 960 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: CUCUMBER MOSAIC VIRUS
        (B) STRAIN: STRAIN C (ix) FEATURE:
        (A) NAME/KEY: CDS
        (B) LOCATION: 1..658

(xi) SEQUENCE DESCRIPTION: SEQ ID NO: 9:

```
ATG GAC AAA TCT GAA TCA ACC AGT GCT GGT CGT AAC CAT CGA CGT CGT        48
Met Asp Lys Ser Glu Ser Thr Ser Ala Gly Arg Asn His Arg Arg Arg
220             225                 230                 235

CCG CGT CGT GGT TCC CGC TCC GCC CCC TCC TCC GCG GAT GCT AAC TTT        96
Pro Arg Arg Gly Ser Arg Ser Ala Pro Ser Ser Ala Asp Ala Asn Phe
                240                 245                 250

AGA GTC TTG TCG CAG CAG CTT TCG CGA CTT AAT AAG ACG TTA GCA GCT       144
Arg Val Leu Ser Gln Gln Leu Ser Arg Leu Asn Lys Thr Leu Ala Ala
            255                 260                 265

GGT CGT CCA ACT ATT AAC CAC CCA ACC TTT GTA GGG AGT GAA CGC TGT       192
Gly Arg Pro Thr Ile Asn His Pro Thr Phe Val Gly Ser Glu Arg Cys
```

-continued

```
                270                 275                 280
AGA CCT GGG TAC ACG TTC ACA TCT ATT ACC CTA AAG CCA CCA AAA ATA       240
Arg Pro Gly Tyr Thr Phe Thr Ser Ile Thr Leu Lys Pro Pro Lys Ile
    285                 290                 295

GAC CGT GAG TCT TAT TAC GGT AAA AGG TTG TTA CTA CCT GAT TCA GTC       288
Asp Arg Glu Ser Tyr Tyr Gly Lys Arg Leu Leu Leu Pro Asp Ser Val
300                 305                 310                 315

ACG GAA TAT GAT AAG AAG CTT GTT TCG CGC ATT CAA ATT CGA GTT AAT       336
Thr Glu Tyr Asp Lys Lys Leu Val Ser Arg Ile Gln Ile Arg Val Asn
                320                 325                 330

CCT TTG CCG AAA TTT GAT TCT ACC GTG TGG GTG ACA GTC CGT AAA GTT       384
Pro Leu Pro Lys Phe Asp Ser Thr Val Trp Val Thr Val Arg Lys Val
            335                 340                 345

CCT GCC TCC TCG GAC TTA TCC GTT GCC GCC ATC TCT GCT ATG TTC GCG       432
Pro Ala Ser Ser Asp Leu Ser Val Ala Ala Ile Ser Ala Met Phe Ala
        350                 355                 360

GAC GGA GCC TCA CCG GTA CTG GTT TAT CAG TAT GCC GCA TCT GGA GTC       480
Asp Gly Ala Ser Pro Val Leu Val Tyr Gln Tyr Ala Ala Ser Gly Val
    365                 370                 375

CAA GCC AAC AAC AAA CTG TTG TTT GAT CTT TCG GCG ATG CGC GCT GAT       528
Gln Ala Asn Asn Lys Leu Leu Phe Asp Leu Ser Ala Met Arg Ala Asp
380                 385                 390                 395

ATA GGT GAC ATG AGA AAG TAC GCC GTC CTC GTG TAT TCA AAA GAC GAT       576
Ile Gly Asp Met Arg Lys Tyr Ala Val Leu Val Tyr Ser Lys Asp Asp
                400                 405                 410

GCG CTC GAG ACG GAC GAG CTA GTA CTT CAT GTT GAC ATC GAG CAC CAA       624
Ala Leu Glu Thr Asp Glu Leu Val Leu His Val Asp Ile Glu His Gln
            415                 420                 425

CGC ATT CCC ACA TCT GGA GTG CTC CCA GTC TGA T TCCGTGTTCC              668
Arg Ile Pro Thr Ser Gly Val Leu Pro Val  *
        430                 435

CAGAACCCTC CCTCCGATCT CTGTGGCGGG AGCTGAGTTG GCAGTTCTAC TACAAACTGT     728

CTGGAGTCAC TAAACGTTTT ACGGTGAACG GGTTGTCCAT CCAGCTTACG GCTAAAATGG     788

TCAGTCGTGG AGAAATCCAC GCCAGCAGAT TTACAAATCT CTGAGGCGCC TTTGAAACCA     848

TCTCCTAGGT TTCTTCGGAA GGGCTTCGGT CCGTGTACCT CTAGCGCAAC GTGCTAGTTT     908

CAGGGTACGG GTGCCCCCCC ACTTTCGTGG GGGCCTCCAA AAGGAGACCA AA             960
```

(2) INFORMATION FOR SEQ ID NO: 10:

(i) SEQUENCE CHARACTERISTICS:
        (A) LENGTH: 218 amino acids
        (B) TYPE: amino acid
        (D) TOPOLOGY: linear (ii) MOLECULE TYPE: protein (xi) SEQUENCE DESCRIPTION: SEQ ID NO: 10:

```
Met Asp Lys Ser Glu Ser Thr Ser Ala Gly Arg Asn His Arg Arg Arg
1               5                   10                  15

Pro Arg Arg Gly Ser Arg Ser Ala Pro Ser Ser Ala Asp Ala Asn Phe
            20                  25                  30

Arg Val Leu Ser Gln Gln Leu Ser Arg Leu Asn Lys Thr Leu Ala Ala
        35                  40                  45

Gly Arg Pro Thr Ile Asn His Pro Thr Phe Val Gly Ser Glu Arg Cys
    50                  55                  60

Arg Pro Gly Tyr Thr Phe Thr Ser Ile Thr Leu Lys Pro Pro Lys Ile
65                  70                  75                  80
```

-continued

```
Asp Arg Glu Ser Tyr Tyr Gly Lys Arg Leu Leu Pro Asp Ser Val
                 85                  90                  95

Thr Glu Tyr Asp Lys Lys Leu Val Ser Arg Ile Gln Ile Arg Val Asn
                100                 105                 110

Pro Leu Pro Lys Phe Asp Ser Thr Val Trp Val Thr Val Arg Lys Val
            115                 120                 125

Pro Ala Ser Ser Asp Leu Ser Val Ala Ala Ile Ser Ala Met Phe Ala
        130                 135                 140

Asp Gly Ala Ser Pro Val Leu Val Tyr Gln Tyr Ala Ala Ser Gly Val
145                 150                 155                 160

Gln Ala Asn Asn Lys Leu Leu Phe Asp Leu Ser Ala Met Arg Ala Asp
                165                 170                 175

Ile Gly Asp Met Arg Lys Tyr Ala Val Leu Val Tyr Ser Lys Asp Asp
                180                 185                 190

Ala Leu Glu Thr Asp Glu Leu Val Leu His Val Asp Ile Glu His Gln
            195                 200                 205

Arg Ile Pro Thr Ser Gly Val Leu Pro Val
        210                 215
```

(2) INFORMATION FOR SEQ ID NO: 11:

(i) SEQUENCE CHARACTERISTICS:
        (A) LENGTH: 983 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: CUCUMBER MOSAIC VIRUS
        (B) STRAIN: WHITE LEAF (ix) FEATURE:
        (A) NAME/KEY: CDS
        (B) LOCATION: 1..657

(x) PUBLICATION INFORMATION:
        (A) AUTHORS: Quemada, H
            Kearney, C
            Gonsalves, D
            Slightom, J
        (B) TITLE: Nucleotide Sequences of the Coat Protein
            Genes and Flanking Regions of Cucumber Mosaic
            Virus Strains C and WL RNA 3
        (C) JOURNAL: J. Gen. Virol.
        (D) VOLUME: 70
        (F) PAGES: 1065-1073
        (G) DATE: 1989

(xi) SEQUENCE DESCRIPTION: SEQ ID NO: 11:

```
ATG GAC AAA TCT GGA TCT CCC AAT GCT AGT AGA ACC TCC CGG CGT CGT      48
Met Asp Lys Ser Gly Ser Pro Asn Ala Ser Arg Thr Ser Arg Arg Arg
220                 225                 230                 235

CGC CCG CGT AGA GGT TCT CGG TCC GCT TCT GGT GCG GAT GCA GGG TTG      96
Arg Pro Arg Arg Gly Ser Arg Ser Ala Ser Gly Ala Asp Ala Gly Leu
                240                 245                 250

CGT GCT TTG ACT CAG CAG ATG CTG AAA CTC AAT AGA ACC CTC GCC ATT     144
Arg Ala Leu Thr Gln Gln Met Leu Lys Leu Asn Arg Thr Leu Ala Ile
                255                 260                 265

GGT CGT CCC ACT CTT AAC CAC CCA ACC TTC GTG GGT AGT GAA AGC TGT     192
Gly Arg Pro Thr Leu Asn His Pro Thr Phe Val Gly Ser Glu Ser Cys
```

-continued

```
                   270                     275                      280
AAA CCC GGT TAC ACT TTC ACA TCT ATT ACC CTG AAA CCG CCT GAA ATT        240
Lys Pro Gly Tyr Thr Phe Thr Ser Ile Thr Leu Lys Pro Pro Glu Ile
        285                     290                     295

GAG AAA GGT TCA TAT TTT GGT AGA AGG TTG TCT TTG CCA GAT TCA GTC        288
Glu Lys Gly Ser Tyr Phe Gly Arg Arg Leu Ser Leu Pro Asp Ser Val
300                     305                     310                     315

ACG GAC TAT GAT AAG AAG CTT GTT TCG CGC ATT CAA ATC AGG GTT AAT        336
Thr Asp Tyr Asp Lys Lys Leu Val Ser Arg Ile Gln Ile Arg Val Asn
                320                     325                     330

CCT TTG CCG AAA TTT GAT TCT ACC GTG TGG GTT ACA GTT CGG AAA GTA        384
Pro Leu Pro Lys Phe Asp Ser Thr Val Trp Val Thr Val Arg Lys Val
        335                     340                     345

CCT TCA TCA TCC GAT CTT TCC GTC GCC GCC ATC TCT GCT ATG TTT GGC        432
Pro Ser Ser Ser Asp Leu Ser Val Ala Ala Ile Ser Ala Met Phe Gly
        350                     355                     360

GAT GGT AAT TCA CCG GTT TTG GTT TAT CAG TAT GCT GCG TCC GGA GTT        480
Asp Gly Asn Ser Pro Val Leu Val Tyr Gln Tyr Ala Ala Ser Gly Val
        365                     370                     375

CAG GCC AAC AAT AAG TTA CTT TAT GAC CTG TCC GAG ATG CGT GCT GAT        528
Gln Ala Asn Asn Lys Leu Leu Tyr Asp Leu Ser Glu Met Arg Ala Asp
380                     385                     390                     395

ATC GGC GAC ATG CGT AAG TAC GCC GTC CTG GTT TAC TCG AAA GAC GAT        576
Ile Gly Asp Met Arg Lys Tyr Ala Val Leu Val Tyr Ser Lys Asp Asp
                400                     405                     410

AAA CTA GAG AAG GAC GAG ATT GCA CTT CAT GTC GAC GTC GAG CAT CAA        624
Lys Leu Glu Lys Asp Glu Ile Ala Leu His Val Asp Val Glu His Gln
        415                     420                     425

CGA ATT CCT ATC TCA CGG ATG CTC CCG ACT TAG TCCGTGTGTT TACCGGCGTC      677
Arg Ile Pro Ile Ser Arg Met Leu Pro Thr  *
        430                     435

CGAGAACGTT AAACTACACT CTCAATCGCG AGTGCTGACT TGGTAGTATT GCTTCAAACT      737

GCCTGAAGTC CCTAAACGTG TTGTTGCGCG GGGAACGGGT GTCCATCCAG CTTACGGCTA      797

AAATGGTCGT GTCTTTCACA CGCCGATGTC TTACAAGATG TCGAGATACC CTTGAAATCA      857

TCTCCTAGAT TTCTTCGGAA GGGCTTCGTG AGAAGCTCGT GCACGGTAAT ACACTTGATA      917

TTACCAAGAG TGCGGGTATC GCCTGTGGTT TTCCACAGGT TCTCCAGGTT CTCCATAAGG      977

AGACCA                                                                  983
```

(2) INFORMATION FOR SEQ ID NO: 12:

(i) SEQUENCE CHARACTERISTICS:
        (A) LENGTH: 218 amino acids
        (B) TYPE: amino acid
        (D) TOPOLOGY: linear (ii) MOLECULE TYPE: protein (xi) SEQUENCE DESCRIPTION: SEQ ID NO: 12:

```
Met Asp Lys Ser Gly Ser Pro Asn Ala Ser Arg Thr Ser Arg Arg Arg
1               5                   10                  15

Arg Pro Arg Arg Gly Ser Arg Ser Ala Ser Gly Ala Asp Ala Gly Leu
            20                  25                  30

Arg Ala Leu Thr Gln Gln Met Leu Lys Leu Asn Arg Thr Leu Ala Ile
        35                  40                  45

Gly Arg Pro Thr Leu Asn His Pro Thr Phe Val Gly Ser Glu Ser Cys
    50                  55                  60

Lys Pro Gly Tyr Thr Phe Thr Ser Ile Thr Leu Lys Pro Pro Glu Ile
```

```
            65                  70                  75                  80
Glu Lys Gly Ser Tyr Phe Gly Arg Arg Leu Ser Leu Pro Asp Ser Val
                    85                  90                  95
Thr Asp Tyr Asp Lys Lys Leu Val Ser Arg Ile Gln Ile Arg Val Asn
                100                 105                 110
Pro Leu Pro Lys Phe Asp Ser Thr Val Trp Val Thr Val Arg Lys Val
            115                 120                 125
Pro Ser Ser Ser Asp Leu Ser Val Ala Ala Ile Ser Ala Met Phe Gly
        130                 135                 140
Asp Gly Asn Ser Pro Val Leu Val Tyr Gln Tyr Ala Ala Ser Gly Val
145                 150                 155                 160
Gln Ala Asn Asn Lys Leu Leu Tyr Asp Leu Ser Glu Met Arg Ala Asp
                165                 170                 175
Ile Gly Asp Met Arg Lys Tyr Ala Val Leu Val Tyr Ser Lys Asp Asp
                180                 185                 190
Lys Leu Glu Lys Asp Glu Ile Ala Leu His Val Asp Val Glu His Gln
            195                 200                 205
Arg Ile Pro Ile Ser Arg Met Leu Pro Thr
    210                 215
```

(2) INFORMATION FOR SEQ ID NO: 13:

(i) SEQUENCE CHARACTERISTICS:
        (A) LENGTH: 218 amino acids
        (B) TYPE: amino acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: CUCUMBER MOSAIC VIRUS
        (B) STRAIN: Q3

(x) PUBLICATION INFORMATION:
        (A) AUTHORS: Gould, AR
            Symons, RH
        (B) TITLE: Cucumber Mosaic Virus RNA 3: Determination
            of the nucleotide sequence provides the amino acid
            sequences of protein 3a and viral coat protein
        (C) JOURNAL: Eur. J. Biochem
        (D) VOLUME: 126
        (F) PAGES: 217-226
        (G) DATE: 1982

(xi) SEQUENCE DESCRIPTION: SEQ ID NO: 13:

```
Met Asp Lys Ser Gly Ser Pro Asn Ala Ser Arg Thr Ser Arg Arg Arg
1                   5                  10                  15
Arg Pro Arg Arg Gly Ser Arg Ser Ala Ser Gly Ala Asp Ala Gly Leu
                20                  25                  30
Arg Ala Leu Thr Gln Gln Met Leu Arg Leu Asn Lys Thr Leu Ala Ile
            35                  40                  45
Gly Arg Pro Thr Leu Asn His Pro Thr Phe Val Gly Ser Glu Ser Cys
        50                  55                  60
Lys Pro Gly Tyr Thr Phe Thr Ser Ile Thr Leu Lys Pro Pro Glu Ile
65                  70                  75                  80
Glu Lys Gly Ser Tyr Phe Gly Arg Arg Leu Ser Leu Pro Asp Ser Val
                    85                  90                  95
```

```
Thr Asp Tyr Asp Lys Leu Val Ser Arg Ile Gln Ile Arg Ile Asn
            100                 105                 110

Pro Leu Pro Lys Phe Asp Ser Thr Val Trp Val Thr Val Arg Lys Val
            115                 120                 125

Pro Ser Ser Asp Leu Ser Val Ala Ala Ile Ser Ala Met Phe Gly
130                 135                 140

Asp Gly Asn Ser Pro Val Leu Val Tyr Gln Tyr Ala Ala Ser Gly Val
145                 150                 155                 160

Gln Ala Asn Asn Lys Leu Leu Tyr Asp Leu Ser Glu Met Arg Ala Asp
                165                 170                 175

Ile Gly Asp Met Arg Lys Tyr Ala Val Leu Val Tyr Ser Lys Asp Asp
            180                 185                 190

Lys Leu Glu Lys Asp Glu Ile Val Leu His Val Asp Val Glu His Gln
            195                 200                 205

Arg Ile Pro Ile Ser Arg Met Leu Pro Thr
        210                 215

(2) INFORMATION FOR SEQ ID NO: 14:

(i) SEQUENCE CHARACTERISTICS:
        (A) LENGTH: 772 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Cucumber Mosaic Virus
        (C) INDIVIDUAL ISOLATE: A35

(ix) FEATURE:
        (A) NAME/KEY: CDS
        (B) LOCATION: 3..660

(xi) SEQUENCE DESCRIPTION: SEQ ID NO: 14:

CC ATG GAC AAA TCT GAA TCA ACC AGT GCT GGT CGT AAC CGT CGA CGT        47
   Met Asp Lys Ser Glu Ser Thr Ser Ala Gly Arg Asn Arg Arg Arg
   220                 225                 230

CGT CCG CGT CGT GGT TCC CGC TCC GCC CTC TCC TCC GCG GAT GCT AAC       95
Arg Pro Arg Arg Gly Ser Arg Ser Ala Leu Ser Ser Ala Asp Ala Asn
235                 240                 245                 250

TTT AGA GTC CTG TCG CAG CAG CTT TCG CGA CTT AAT AAG ACG TTA GCA      143
Phe Arg Val Leu Ser Gln Gln Leu Ser Arg Leu Asn Lys Thr Leu Ala
                255                 260                 265

GCT GGT CGT CCA ACT ATT AAC CAC CCA ACC TTT GTA GGG AGT GAA CGC      191
Ala Gly Arg Pro Thr Ile Asn His Pro Thr Phe Val Gly Ser Glu Arg
            270                 275                 280

TGT AGA CCT GGG TAC ACG TTC ACA TCT ATT ACC CTA AAG CCA CCA AAA      239
Cys Arg Pro Gly Tyr Thr Phe Thr Ser Ile Thr Leu Lys Pro Pro Lys
            285                 290                 295

ATA GAC CGT GGG TCT TAT TAC GGT AAA AGG TTG TTA CTA CCT GAT TCA      287
Ile Asp Arg Gly Ser Tyr Tyr Gly Lys Arg Leu Leu Leu Pro Asp Ser
300                 305                 310

GTC ACA GAA TAT GAT AAG AAG CTT GTT TCG CGC ATT CAA ATT CGA GTT      335
Val Thr Glu Tyr Asp Lys Lys Leu Val Ser Arg Ile Gln Ile Arg Val
315                 320                 325                 330

AAT CCT TTG CCG AAA TTT GAT TCT ACC GTG TGG GTG ACA GTC CGT AAA      383
Asn Pro Leu Pro Lys Phe Asp Ser Thr Val Trp Val Thr Val Arg Lys
```

-continued

```
                    335                 340                 345
GTT CCT GCC TCC TCG GAC TTA TCC GTT GCC GCC ATC TCT GCT ATG TTC      431
Val Pro Ala Ser Ser Asp Leu Ser Val Ala Ala Ile Ser Ala Met Phe
            350                 355                 360

GCG GAC GGA GCC TCA CCG GTA CTG GTT TAT CAG TAT GCC GCA TCT GGA      479
Ala Asp Gly Ala Ser Pro Val Leu Val Tyr Gln Tyr Ala Ala Ser Gly
            365                 370                 375

GTC CAA GCC AAC AAC AAA CTG TTG TAT GAT CTT TCG GCG ATG CGC GCT      527
Val Gln Ala Asn Asn Lys Leu Leu Tyr Asp Leu Ser Ala Met Arg Ala
        380                 385                 390

GAT ATA GGT GAC ATG AGA AAG TAC GCC GTC CTC GTG TAT TCA AAA GAC      575
Asp Ile Gly Asp Met Arg Lys Tyr Ala Val Leu Val Tyr Ser Lys Asp
395                 400                 405                 410

GAT GCG CTC GAG ACG GAC GAG CTA GTA CTT CAT GTT GAC ATC GAG CAC      623
Asp Ala Leu Glu Thr Asp Glu Leu Val Leu His Val Asp Ile Glu His
                415                 420                 425

CAA CGC ATT CCC ACG TCT GGA GTG CTC CCA GTC TGA T TCTGTGTTCC         670
Gln Arg Ile Pro Thr Ser Gly Val Leu Pro Val  *
            430                 435

CAGAACCCTC CCTCCGATCT CTGTGGCGGG AGCTGAGTTG GCAGTTCTGC TGTAAACTGT    730

CTGAAGTCAC TAAACGTTTT ACGGTGAACG GGTTGTCCAT GG                       772
```

(2) INFORMATION FOR SEQ ID NO: 15:

(i) SEQUENCE CHARACTERISTICS:
        (A) LENGTH: 218 amino acids
        (B) TYPE: amino acid
        (D) TOPOLOGY: linear (ii) MOLECULE TYPE: protein (xi) SEQUENCE DESCRIPTION: SEQ ID NO: 15:

```
Met Asp Lys Ser Glu Ser Thr Ser Ala Gly Arg Asn Arg Arg Arg
 1               5                  10                  15

Pro Arg Arg Gly Ser Arg Ser Ala Leu Ser Ser Ala Asp Ala Asn Phe
                20                  25                  30

Arg Val Leu Ser Gln Gln Leu Ser Arg Leu Asn Lys Thr Leu Ala Ala
            35                  40                  45

Gly Arg Pro Thr Ile Asn His Pro Thr Phe Val Gly Ser Glu Arg Cys
        50                  55                  60

Arg Pro Gly Tyr Thr Phe Thr Ser Ile Thr Leu Lys Pro Pro Lys Ile
65                  70                  75                  80

Asp Arg Gly Ser Tyr Tyr Gly Lys Arg Leu Leu Leu Pro Asp Ser Val
                85                  90                  95

Thr Glu Tyr Asp Lys Lys Leu Val Ser Arg Ile Gln Ile Arg Val Asn
                100                 105                 110

Pro Leu Pro Lys Phe Asp Ser Thr Val Trp Val Thr Val Arg Lys Val
            115                 120                 125

Pro Ala Ser Ser Asp Leu Ser Val Ala Ala Ile Ser Ala Met Phe Ala
        130                 135                 140

Asp Gly Ala Ser Pro Val Leu Val Tyr Gln Tyr Ala Ala Ser Gly Val
145                 150                 155                 160

Gln Ala Asn Asn Lys Leu Leu Tyr Asp Leu Ser Ala Met Arg Ala Asp
                165                 170                 175

Ile Gly Asp Met Arg Lys Tyr Ala Val Leu Val Tyr Ser Lys Asp Asp
            180                 185                 190

Ala Leu Glu Thr Asp Glu Leu Val Leu His Val Asp Ile Glu His Gln
```

-continued

```
        195                 200                 205

Arg Ile Pro Thr Ser Gly Val Leu Pro Val
    210                 215
```